United States Patent [19]

Piller et al.

[11] 4,026,709

[45] May 31, 1977

[54] COLOR PHOTOGRAPHIC RECORDING MATERIAL

[75] Inventors: Bernhard Piller; Paul Tschopp; Thomas Stauner; Walter Heierli, all of Marly, Switzerland

[73] Assignee: Ciba-Geigy AG, Basel, Switzerland

[22] Filed: Apr. 19, 1976

[21] Appl. No.: 677,942

Related U.S. Application Data

[62] Division of Ser. No. 446,248, Feb. 27, 1974, Pat. No. 3,984,432.

[52] U.S. Cl. .................................. 96/100; 96/55; 96/56.5
[51] Int. Cl.$^2$ .................................. G03C 1/40
[58] Field of Search ........................ 96/100

[56] References Cited

UNITED STATES PATENTS

| 3,482,971 | 12/1969 | Bloom et al. | 96/100 |
| 3,607,289 | 9/1971 | Keberle et al. | 96/114.4 |
| 3,984,432 | 10/1976 | Piller et al. | 96/100 |

*Primary Examiner*—J. Travis Brown
*Attorney, Agent, or Firm*—Karl F. Jorda; Joseph G. Kolodny; Edward McC. Roberts

[57] ABSTRACT

The present invention relates to new compounds having an active methylene group or phenolic hydroxyl group and therefore capable of being used as photographic color couplers. The new compounds contain at least one radical of a phosphoric acid diester, phosphonic acid diester, phosphoric acid diamide, phosphonic acid diamide, phosphoric acid ester-amide or phosphonic acid ester-amide.

22 Claims, No Drawings

COLOR PHOTOGRAPHIC RECORDING MATERIAL

This is a divisional of application Ser. No. 446,248, filed Feb. 27, 1974, now U.S. Pat. No. 3,984,432

A large number of photographic colour coupling agents with an active methylene group or phenolic hydroxyl group are known, for example from the following publications: German Offenlegungsschriften (or Auslegeschriften) 1,236,332, 1,522,414, 1,547,831 1,547,867, 1,547,868, 1,804,167, 2,018,562, 2,039,970, 2,043,271, 2,123,448, 2,128,830, 2,133,655, 2,152,336, 2,156,913, 2,160,167 and 2,216,578 (compare also 1,113,138), U.S. Pat. Nos. 2,289,804, 2,600,788, 2,801,171, 2,895,826, 2,908,573, 3,265,506 and 3,658,544 and British Pat. No. 1,290,423.

The invention relates to new compounds which can be used as photographic colour coupling agents for the chromogen process and which possess particularly good resistance to diffusion in photographic materials and excellent solubility in the organic solvents known as solvents for coupling agents. These new compounds with an active methylene group or phenolic hydroxyl group contain at least one radical of a phosphoric acid diester, phosphonic acid diester, phosphoric acid diamide, phosphonic acid diamide, phosphoric acid ester-amide or phosphonic acid ester-amide. As a radical with an active methylene group, these compounds contain, for example, the radical of an acylacetylamine or of a 5-pyrazolone, whilst as a radical with a phenolic hydroxyl group they contain, for example, the radical of a phenol or naphthol. Preferred compounds are those which contain the radical of a pivaloyl- or benzoylacetylamine, of a 1-phenyl-5-pyrazolone, of a phenol or of a 1-naphthol-2-carboxylic acid amide. On the other hand, preferred compounds of this nature are those which contain at least one radical of a phosphonic acid diester, that is to say the atom grouping

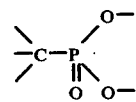

As can be seen from the further comments, the new compounds can not only be 4-equivalent coupling agents but also socalled two-equivalent coupling agents, which possess, in the coupling position, a radical which can be split off during the colour coupling reaction.

Particularly preferred compounds are those of the formulae (1) to (23) which follow:

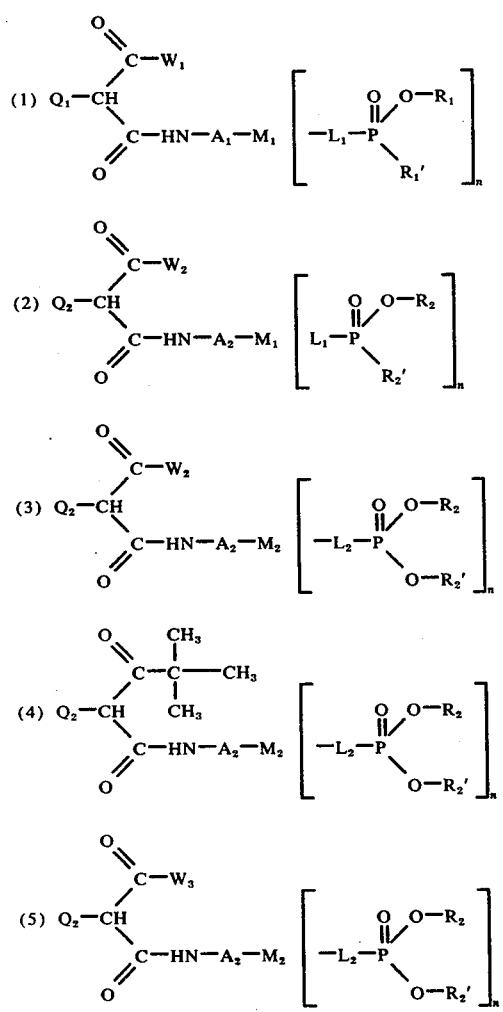

-continued
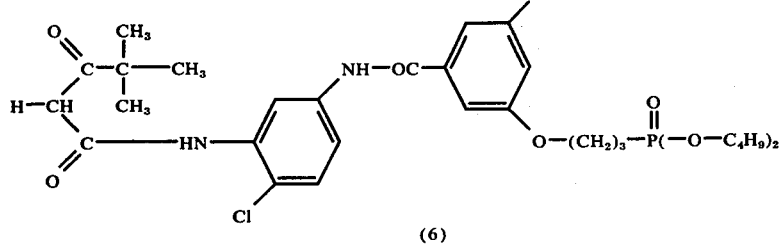
(6)
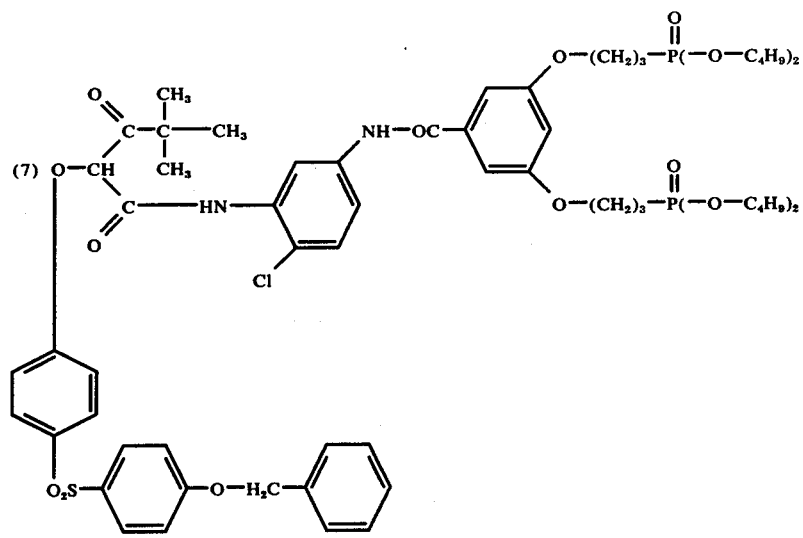
(7)
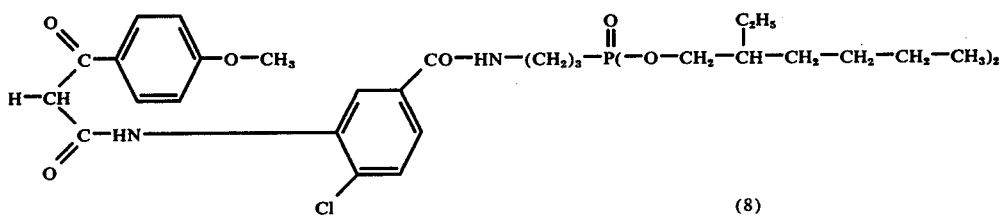
(8)
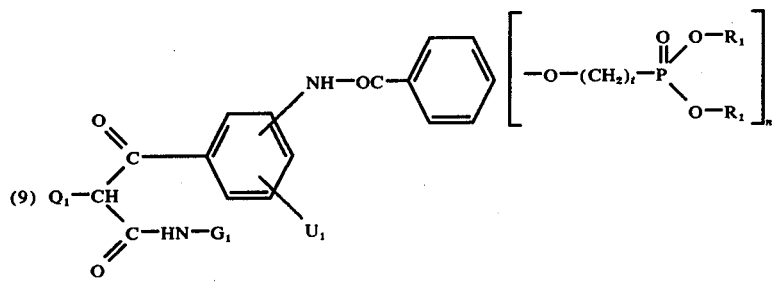
(9)
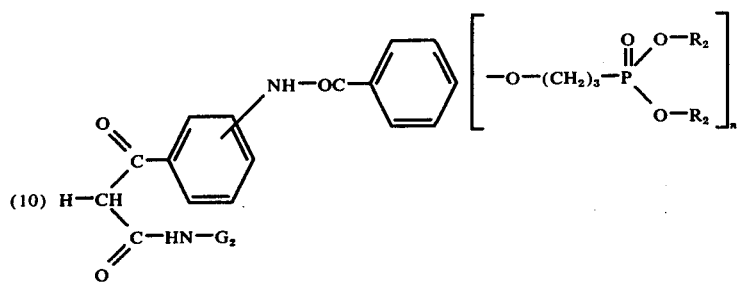
(10)

-continued
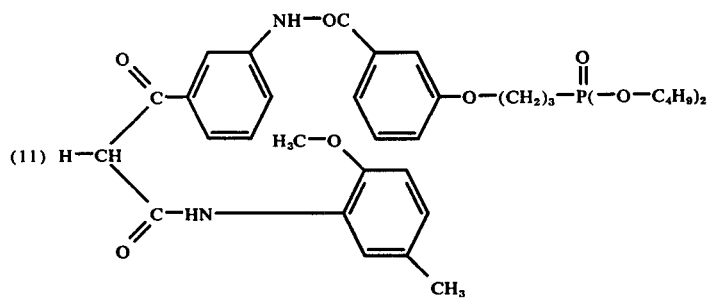
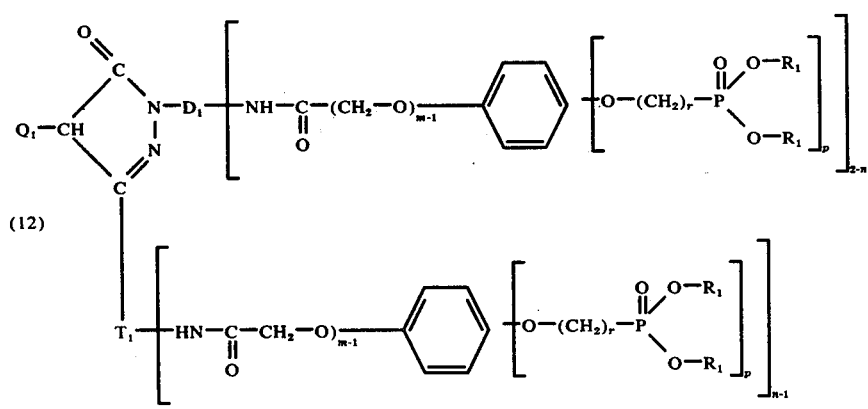
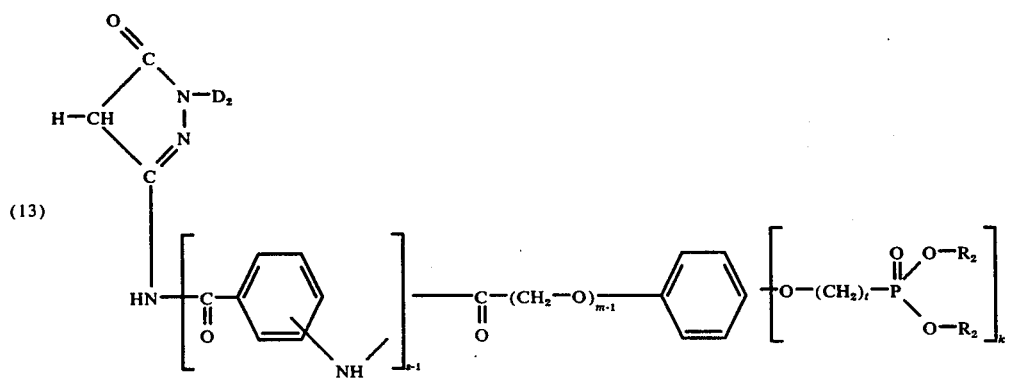
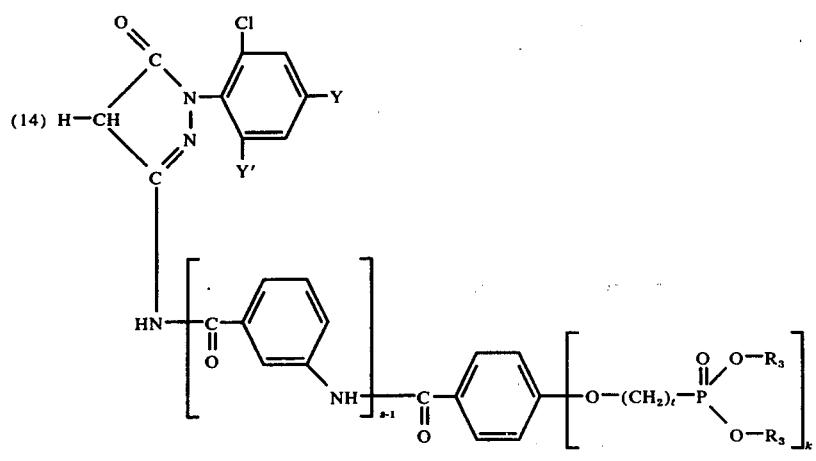

-continued
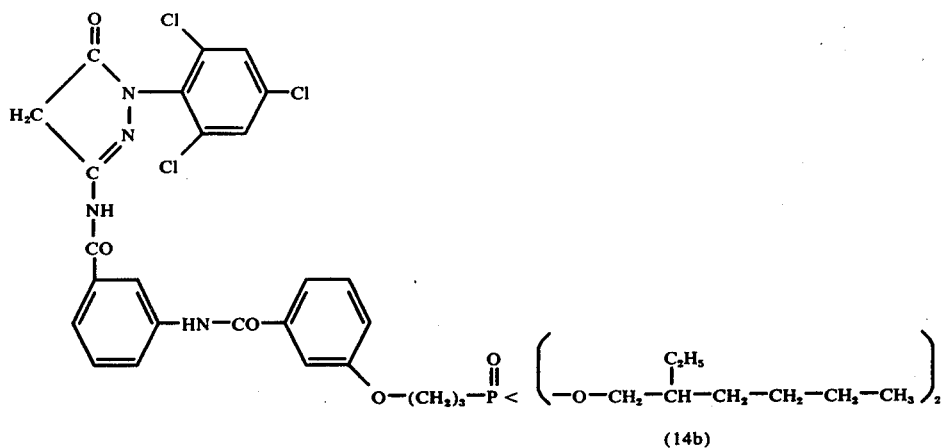
(14b)
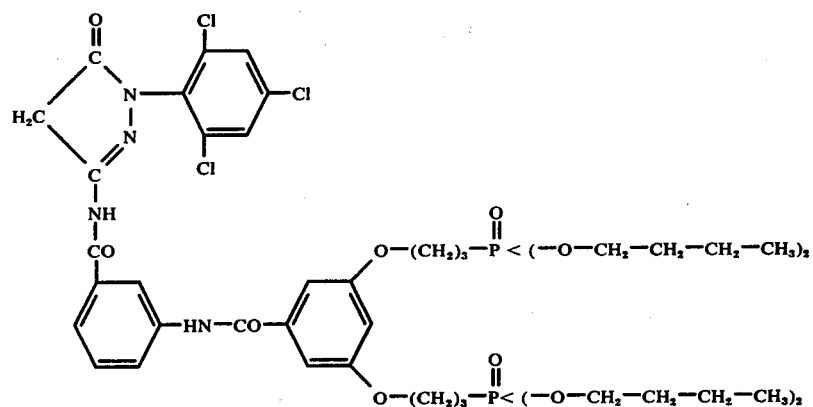
(14c)
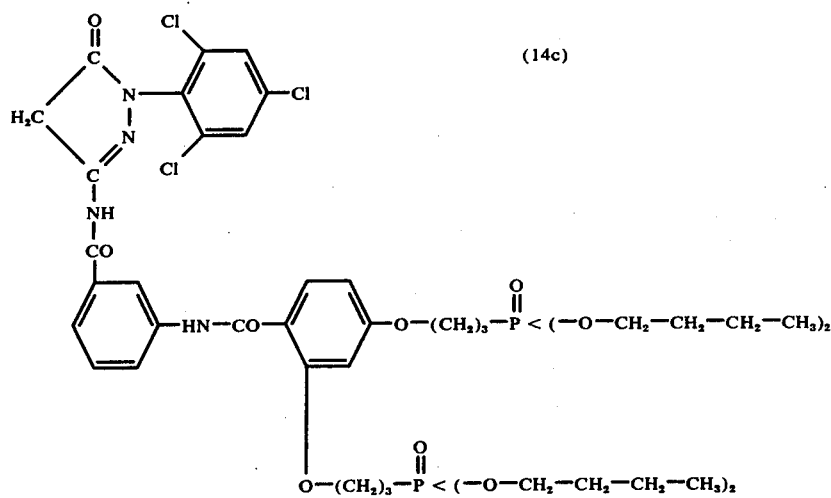

-continued
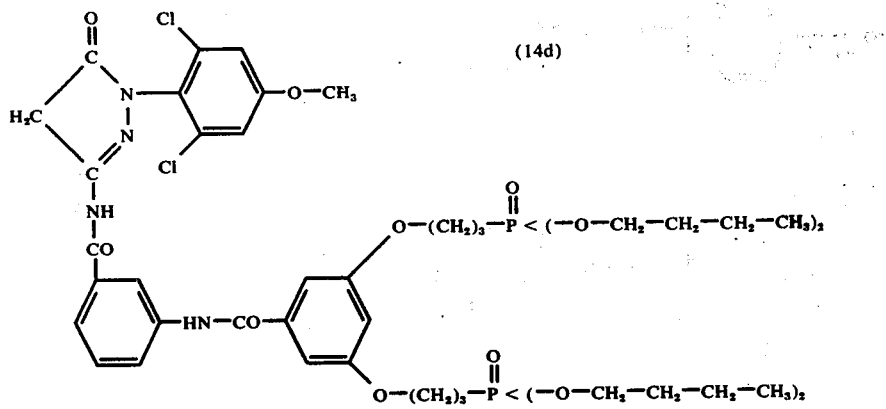
(14d)
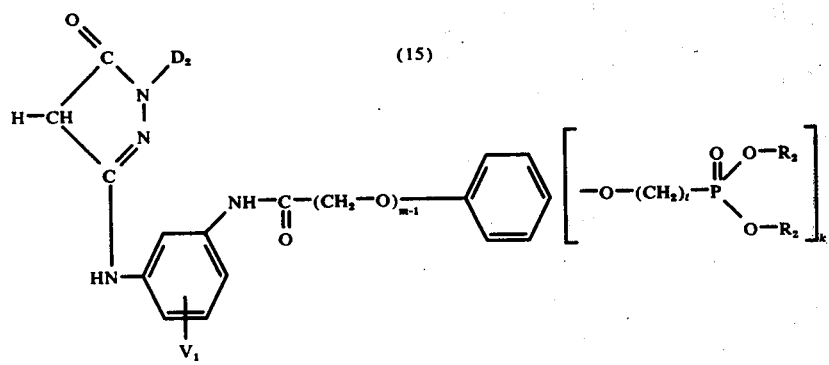
(15)
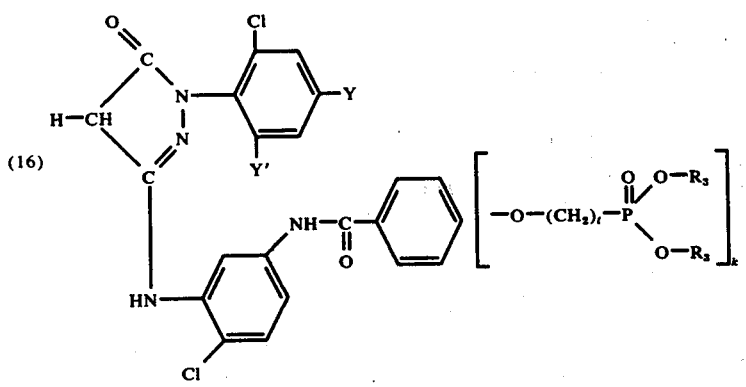
(16)
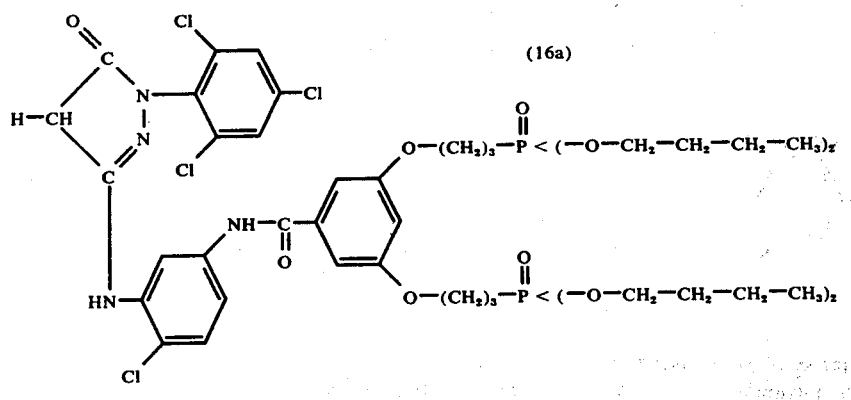
(16a)

-continued
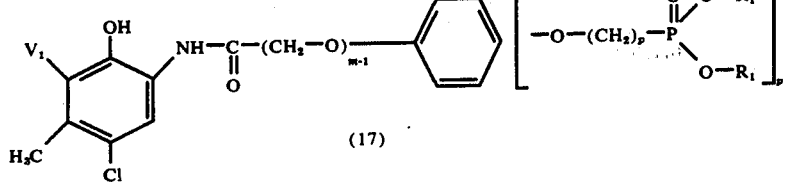
(17)
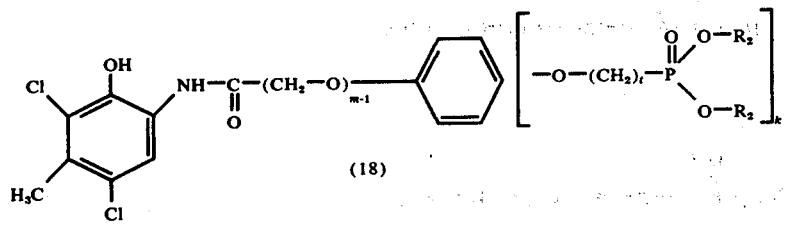
(18)
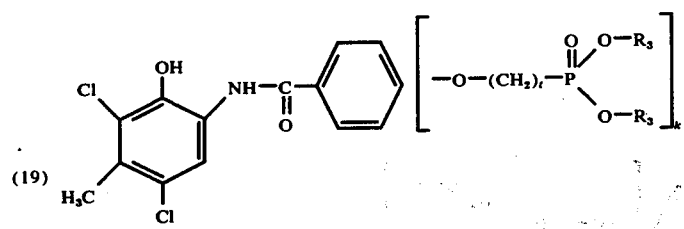
(19)
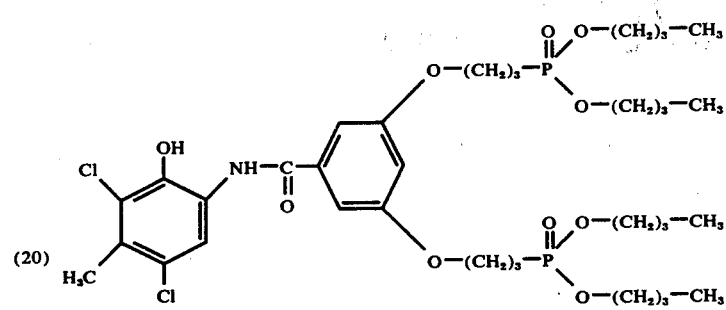
(20)
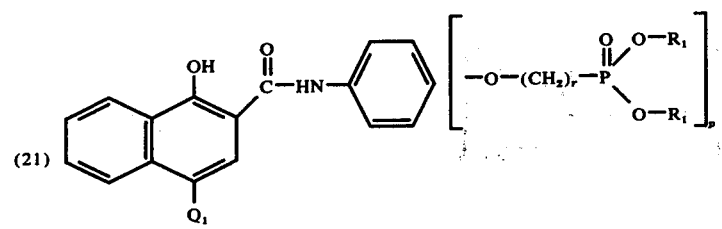
(21)
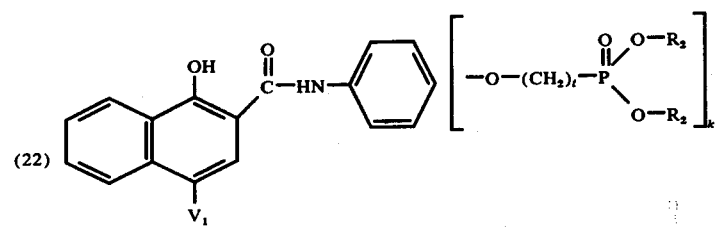
(22)
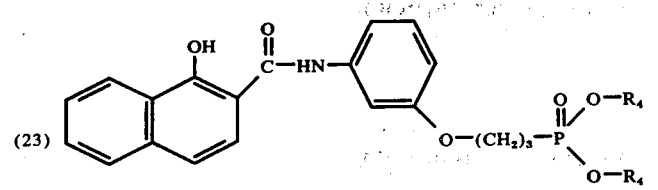
(23)
In the formulae, the individual symbols throughout have the same meaning, and in particular denote the following: $A_1$ denotes a benzene radical which can contain further substituents; $A_2$ denotes a benzene radical which is not substituted further or a benzene radical which is substituted further by at least one of the following substituents: a methyl group, a methoxy group, a phenoxy group or a chlorine atom; $D_1$ denotes a benzene radical which is not substituted further or is substituted further by at least one of the following substituents: a halogen atom such as bromine or preferably chlorine, nitrile, a lower alkyl group (which can carry further substituents, such as a chlorine atom or a methoxy group), a lower alkoxy group, such as ethoxy or methoxy, a lower alkylsulphonyl group, such as a methylsulphonyl group, or an acylamino group with 1 to 28 carbon atoms (lower groups are to be understood as groups with 1 to 4 carbon atoms); $D_2$ denotes a benzene radical which is optionally substituted further by one or more chlorine atoms, methyl groups or methoxy groups and/or a nitrile group; $G_1$ denotes a benzene radical which can contain further substituents; $G_2$ denotes a benzene radical which is not substituted further or is substituted further by at least one of the following substituents: chlorine, methyl, methoxy or phenoxy; $L_1$ denotes an oxygen atom, an alkylene group, a cyclohexane radical, a benzene radical or an aralkylene radical, such as

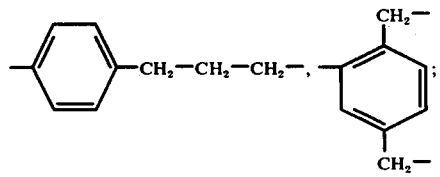

$L_2$ denotes an oxygen atom, an alkylene group with 1 to 3 carbon atoms, a benzene radical or an aralkylene radical; $M_1$ denotes a direct bond, an oxygen atom or one of the following atom groupings:

(wherein the alkyl group contains at most 4 carbon atoms), $-CO-HN-$, $-NH-OC-$, $-CO-O-$, $-CO-HN-$benzene radical or $-NH-OC-$benzene radical; $M_2$ denotes a direct bond, an oxygen atom or one of the atom groupings $-CO-HN-$, $-NH-OC-$, $-CO-HN-$benzene radical and $-NH-OC-$benzene radical; (with regard $M_2-L_2$] it should be noted that M cannot represent oxygen, $-CONH-$ or $-NH-CO$ if L represents an oxygen atom, and n in the formula (3) can be 1 or 2 if $M_2$ is a $-CO-HN-$benzene radical or $-NH-OC-$benzene radical, but must be 1 if $M_2$ represents a direct bond, an oxygen atom, a $-CO-HN-$group or $-NH-OC-$ group; in the $-CO-NH-$benzene radicals and the $-NH-OC-$benzene radicals, if n is 2, the two $-L-$ should be in the 2,4— or 3,5—position to $-CO-HN-$ or $-NH-OC-$); $Q_1$ denotes a radical which can be split off during the colour coupling reaction; $Q_2$ denotes one of the radicals of the formulae $-H$, $-Cl$,

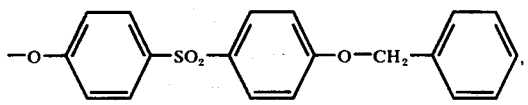

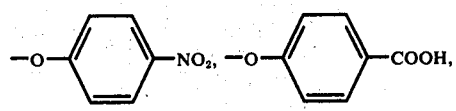

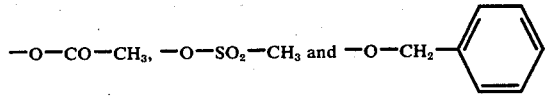

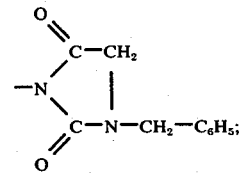

$R_1$ denotes an alkyl group with 2 to 18 carbon atoms; $R'_1$ denotes an alkyl group with 2 to 8 carbon atoms or an alkoxy group with 2 to 18 carbon atoms (the alkoxy groups can also form an $-O-$alkylene group conjointly with $R_1$); $R_2$ denotes an alkyl group with 2 to 8 carbon atoms; $R'_2$ denotes an alkyl group with 2 to 8 carbon atoms or an alkoxy group with 2 to 8 carbon atoms; $R_3$ denotes one of the groups

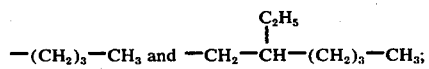

$R_4$ denotes one of the groups $-C_2H_5$ and $-(CH_2)_3-CH_3$; $T_1$ denotes an acylamino group, the nitrogen atom being bonded to the pyrazolone ring, especially a group which consists of a $-NH-CO-$benzene radical, a phenylureido group or a phenylamino group which is not substituted further or is substituted further by at least one of the following substituents: a halogen atom such as bromine or preferably chlorine, a lower alkyl group such as ethyl or methyl, a lower alkoxy group such as ethoxy or methoxy, and an acylamino group with 1 to 28 carbon atoms (lower groups are again to be understood as groups with at most 4 carbon atoms); if $n = 2$, $T_1$ can also denote a direct bond; $U_1$ denotes a hydrogen atom, a chlorine atom, an alkyl group with at most 4 carbon atoms or an alkoxy group with at most 3 carbon atoms; $V_1$ denotes a hydrogen atom or a chlorine atom; $W_1$ denotes an alkyl radical, preferably a radical with 1 to 32 carbon atoms, or a benzene radical, which can also carry substituents; $W_2$ denotes a tertiary butyl radical, a benzene radical which is not substituted further or a benzene radical which is substituted further by at least one of the following substituents: an alkyl group with at most 4 carbon atoms, a methoxy group, an ethoxy group, a chlorine atom or a benzoylamino group; $W_3$ denotes a benzene radical which is not substituted further or is substituted further as indicated for $W_2$; $Y$ denotes a chlorine atom, a methyl group or a methoxy group; $Y'$ denotes a chlorine atom or a methyl group; $k$ denotes one of the numbers 1 and 2; $m$ denotes one of the numbers 1 and 2; $n$ denotes one of the numbers 1 and 2; $p$ denotes one of the numbers 1, 2 and 3; $r$ denotes an integer having a value of at least 1 and at most 18; $s$ denotes one of the numbers 1 and 2; $t$ denotes one of the numbers 3 and 5.

The new colour coupling agents of the initially mentioned composition can be manufactured according to methods which are in themselves known. The following may be mentioned as special manufacturing processes for which patent protection is claimed.

1. An aminoaryl compound containing phosphorus is condensed with an acylacetic acid ester to give the acylacetic acid arylamide. The aminoarylphosphorus compound which serves as the starting material is suitably manufactured by reacting a halogeno-nitro-aryl compound by the Michaelis-Arbuzov reaction with a trialkyl phosphite or triaryl phosphite and then reducing the nitro group of the reaction product to the amino group.

2. Colour coupling agents which contain at least one primary amino group are condensed with carboxylic acid chlorides containing phosphorus.

3. A compound of this nature which contains a pyrazolone (5) ring is synthesised with the aid of an aminobenzene containing phosphorus or a phenylhydrazine containing phosphorus.

The methods of manufacture will still be explained in more detail later.

The known Michaelis-Arbuzov and Perkov reactions are particularly suitable for introducing the phosphoric and phosphinic acid ester radicals or acid ester-amide radicals. See, for example, also the following publications: Methoden der organischen Chemie (Methods of Organic Chemistry) (Houben-Weyl), volumes 12/1 and 12/2, Georg-Thieme Verlag, Stuttgart 1963 and 1964; Symposium on Organo-Phosphorus Compounds held in Heidelberg, Germany, 20-22 May 1964; London, Butterworths 1964, pages 307-369, and literature mentioned therein; Organic Reactions, volume VI, John Wiley & Sons, Inc., New York 1951, pages 273-338, and literature mentioned therein; Organophosphorus Chemistry, volumes 1-3, The Chemical Society, London; Topics in Phosphorus Chemistry, volumes 1-4, Interscience Publishers, London-New York- Sydney.

In particular, coupling agents or suitable intermediate products can be obtained by the Michaelis-Arbuzov method by reaction of halogen derivatives, alcohols, aldehydes, unsaturated aldehydes or unsaturated carboxylic acids with trialkyl phosphites or triaryl phosphites. If the radical containing phosphorus is introduced into an intermediate product, the latter can, if necessary after suitable modification, be introduced into the molecule which is to be coupled or be reacted to give a coupling agent.

A first method, in which the phosphonic acid ester radical is directly introduced into the coupling agent molecule, consists, for example, of reacting a compound of the formula A—Hal wherein A denotes the radical of a colour coupling agent and Hal denotes a halogen atom, preferably a bromine or iodine atom, with a trialkyl phosphite or triaryl phosphite by a Michaelis–Arbusow reaction.

A further method for the direct introduction of the phosphonic acid ester into the coupling agent molecule consists of the addition reaction of a dialkyl phosphite or trialkyl phosphite, or of a diaryl phosphite or triaryl phosphite, with a double bond system present in a compound of the formula

A—H

A third method, in which a phosphonic acid ester radical is initially introduced into a reactive intermediate product, which is subsequently linked to the coupling agent molecule, consists, for example, of reacting a trialkyl phosphite or triaryl phosphite, by a Michaelis–Arbuzov reaction, with a compound of the formula Zw—Hal wherein Zw represents an alkylene or arylene radical which is substituted by a reactive atom, for example a further halogen atom, or by a reactive group, for example an activated ester group or an amino group. The compound thus obtained can then be reacted with a coupling agent, for example of the formula
A—NH$_2$, A—OH, A—COCl or A—NCO, for example according to known methods.

A variant of this method is to modify the phosphorus containing reactive intermediate product yet further before the reaction with a suitable coupling agent molecule, for example by means of the following known reactions at substituents which are present:

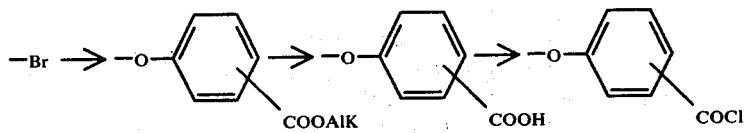

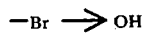

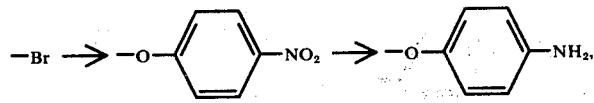

-continued

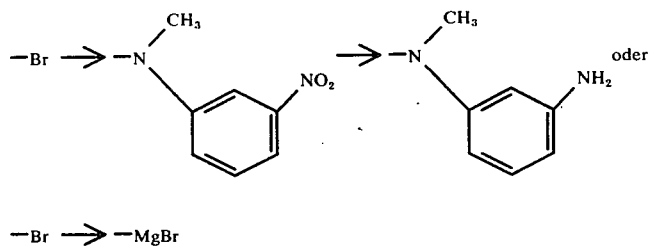

—Br ⟶ —MgBr

A fourth method for the preparation of coupling agents according to the invention is to use an intermediate product obtained, for example, by a Michaelis–Arbuzov reaction between a trialkyl phosphite or triaryl phosphite and a compound of the formula Zw′-Hal, wherein Zw′ has the meaning of Zw, directly or after suitable modification, for the synthesis of the actual coupling agent molecule, for example also of an acylacetanilide or of a pyrazolone ring. Such syntheses are described, inter alia, in: German Auslegeschriften 1,101,429, 1,237,580 and 1,547,867, German Offenlegungschriften 1,670,601, 1,797,083, 2,042,920, 2,042,921, 2,042,922, 2,128,830, 2,156,913 and 2,162,899, or in J. Am. Chem. Soc 71, 983 (1949).

A particular embodiment of this method consists of reacting a nitroaryl compound containing halogen, for example a compound of the formula

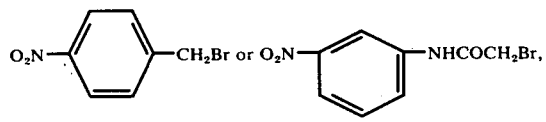

in a Michaelis–Arbuzov reaction with a trialkyl phosphite or triaryl phosphite, reducing the nitro group in the usual manner to the amino group and condensing the phosphorus-containing amino compound thus obtained with an acylacetic acid ester to give an acylacetic acid anilide.

It has hitherto been considered that the Michaelis Arbusow reaction was not generally applicable to a halogen compound containing nitro groups. On this topic see, for example, Accounts of Chemical Research 5, 300 (1972) and Proc. chem. Soc. 1962, 361, Isvest. Akad. Nauk, S.S.S.R., Otdel Chim. Nauk, 1950, 56 and Doklady Akad. Nauk, S.S.S.R., 59, 1301 (1948).

The phosphonic acid ester radical can also be introduced by reaction of a coupling agent, for example of the formula A— NH$_2$ or A — OH with a phostonate.

One method for introducing a phosphoric acid ester radical is characterised, for example, by reacting a phosphoric acid halide of the formula

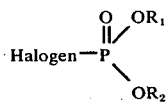

with a coupling agent molecule containing hydroxyl, mercapto or amino groups, or with an intermediate product or salts thereof. In an analogous manner it is also possible to introduce, for example, diaminophosphoryl radicals.

A further method for introducing the phosphoric acid ester radical consists, for example, of reacting an acid of the formula

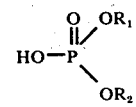

or a salt thereof with a coupling agent molecule containing a reactive halogen atom or an aziridine grouping, or with a suitable intermediate product.

The so-called Perkov reaction of α-halogenocarbonyl compounds or their vinyl homologues or of α-halogenonitro compounds with phosphites, is also particularly suitable for the introduction of the phosphoric acid ester radical.

Reaction of phosphorus oxychloride with coupling agent molecule(s), or intermediate products, containing hydroxyl groups gives dichlorophosphates which subsequently lead directly or via the corresponding acid to diphosphoric acid esters or triphosphoric acid esters, diphosphoric acid amides or ester-amides. On this topic see, for example, J. Chem. Soc., Perkin Trans., 11972, 4, 583–86. Coupling agents, or intermediate products, containing hydroxyl groups can also be condensed with an orthophosphoric or polyphosphoric acid, with elimination of water, after which the resulting phosphoric acid derivative can be esterified.

There now follows a list of compounds from which the colour coupling agents of the composition mentioned initially can be derived by one or more of the abovementioned methods.

The parts of the molecule of the compounds according to the invention which contain the phosphoric acid radicals or phosphonic acid radicals are derived, for example, from compounds of the following formulae:

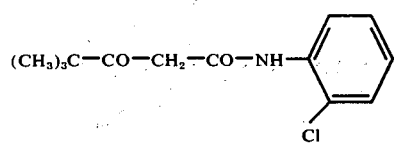

-continued
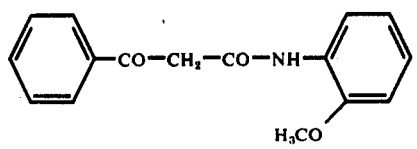
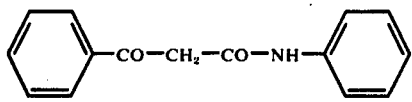
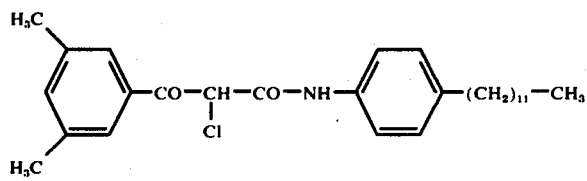
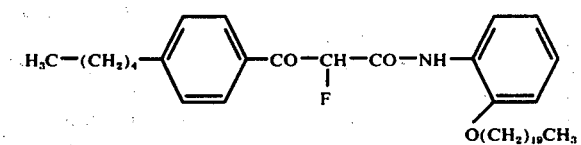
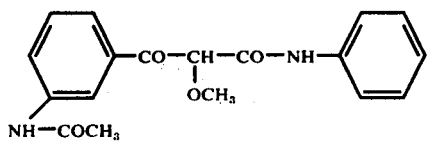
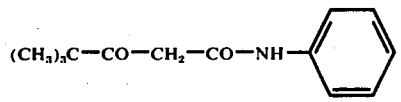
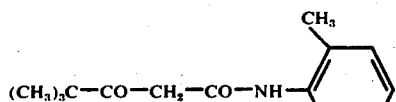
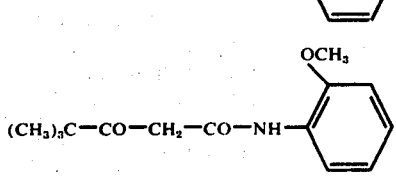
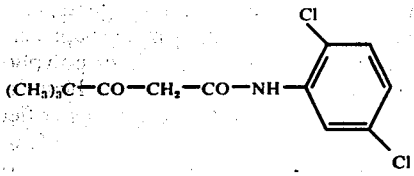
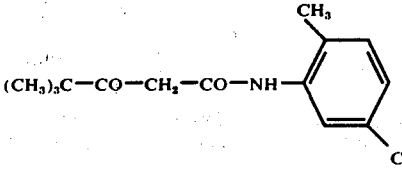
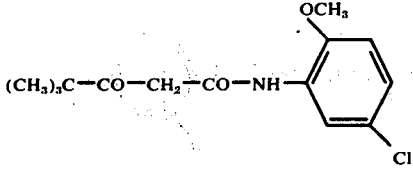

-continued
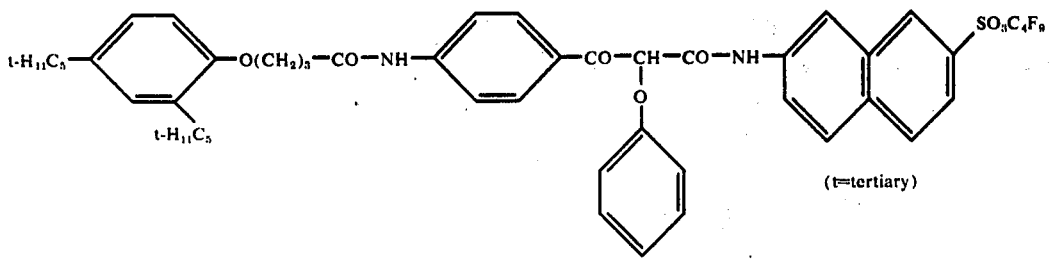
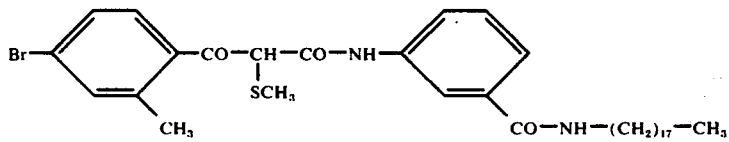
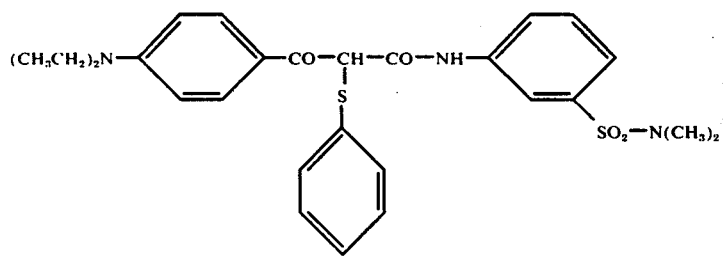
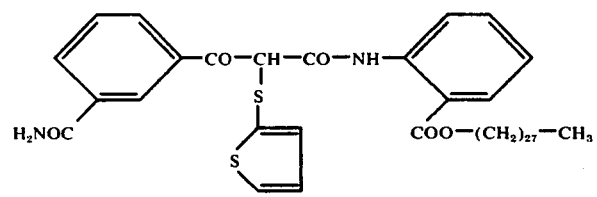
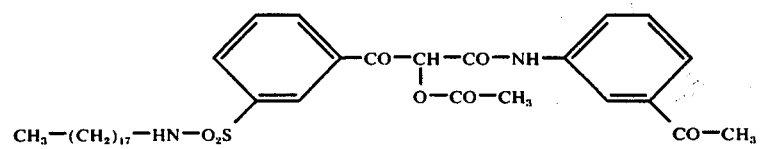
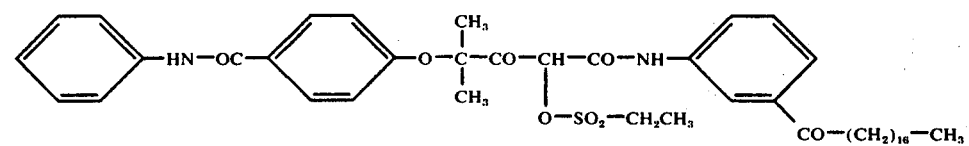
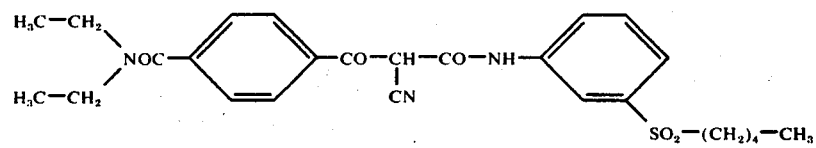
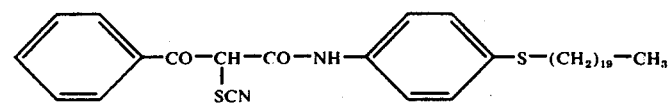

-continued
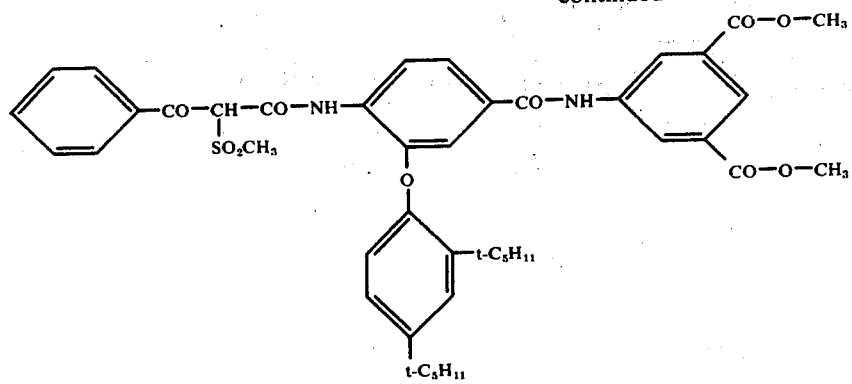
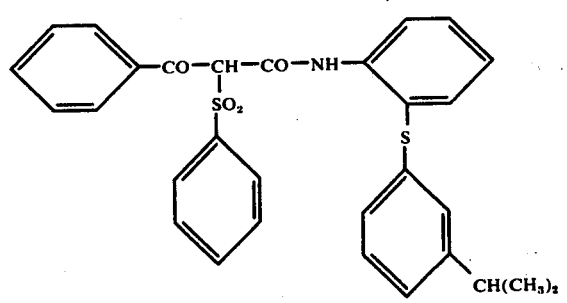
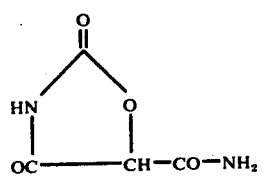
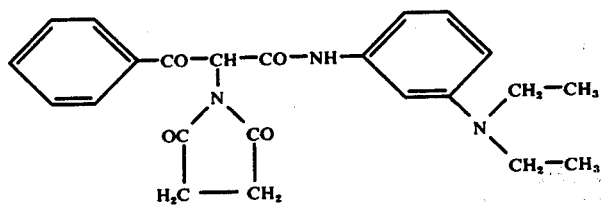
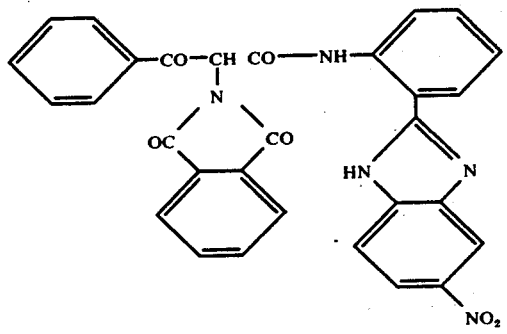
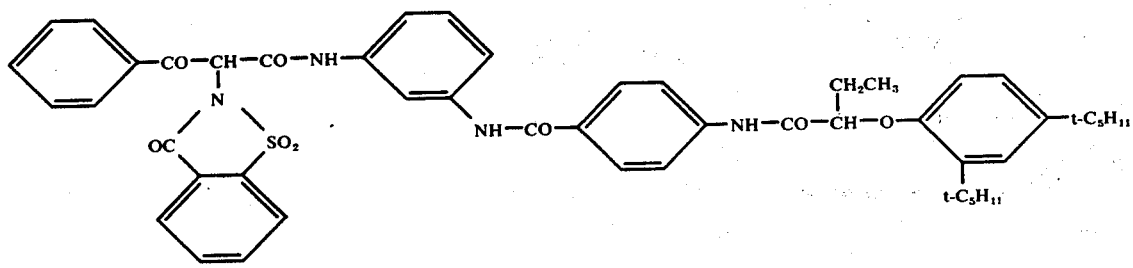

-continued
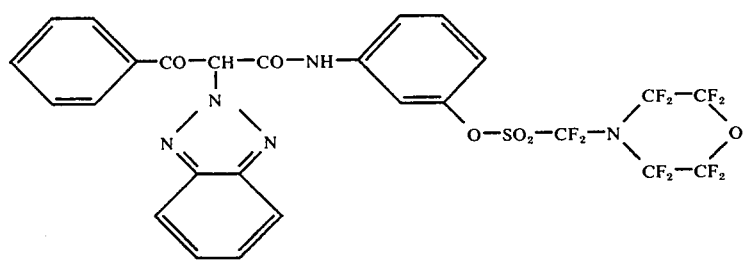
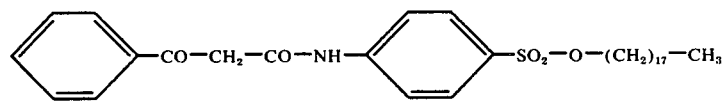
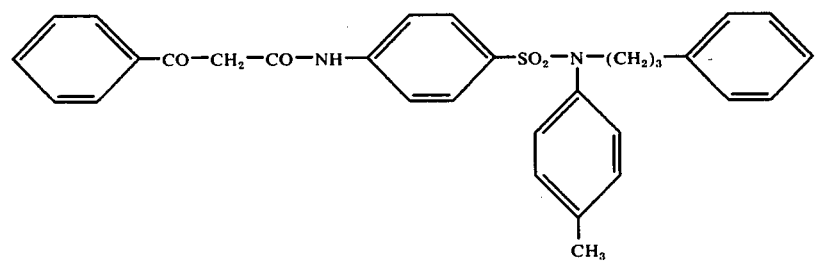
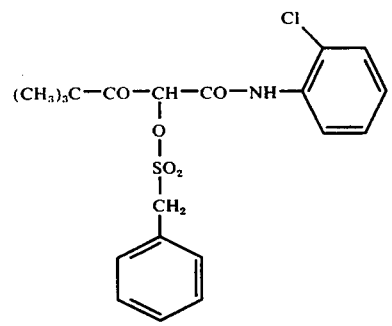
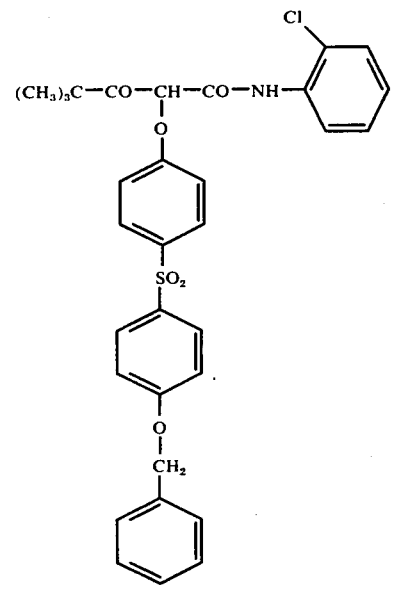

-continued
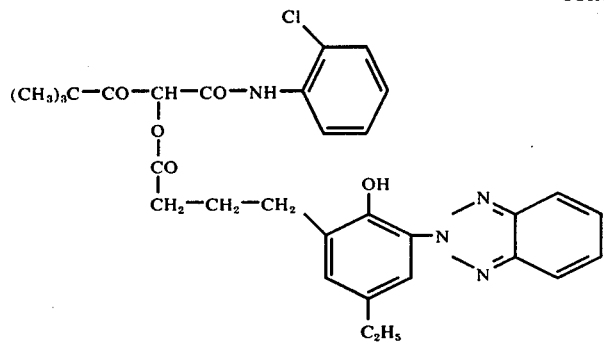
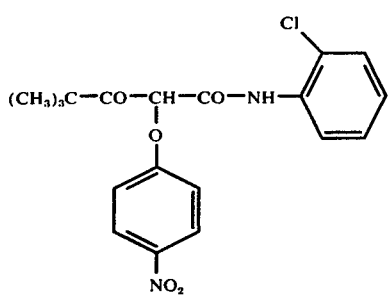
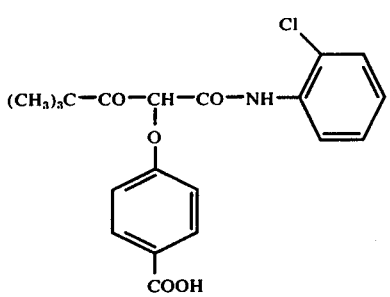
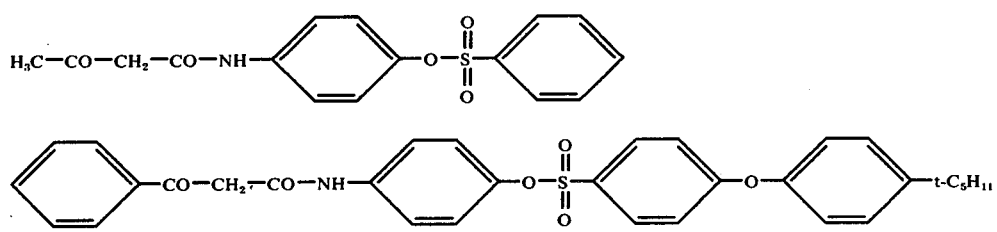
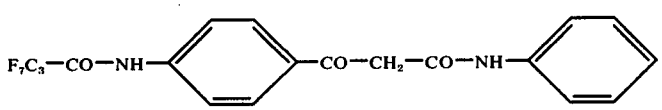
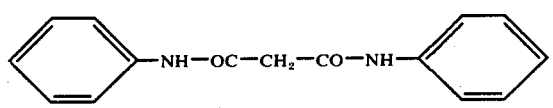
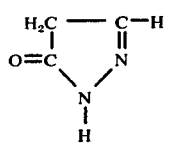
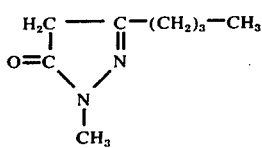

-continued
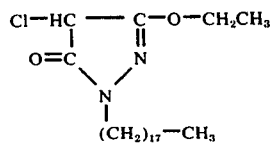
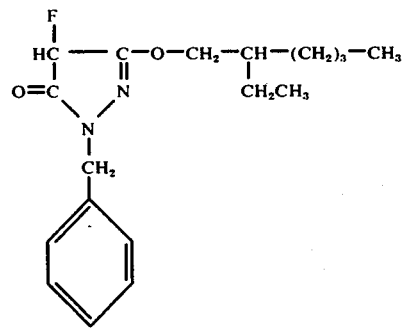
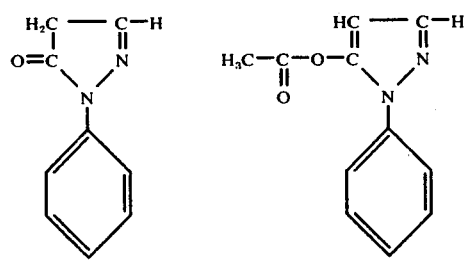
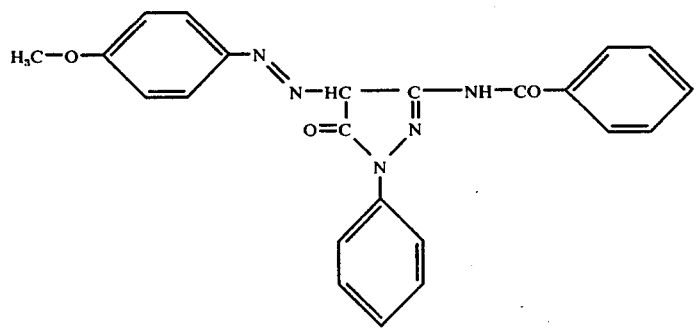
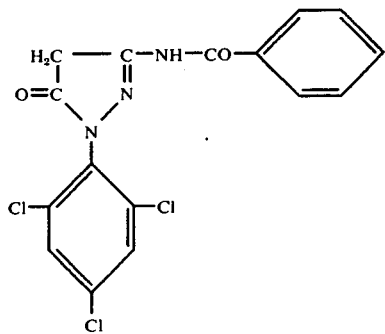

-continued
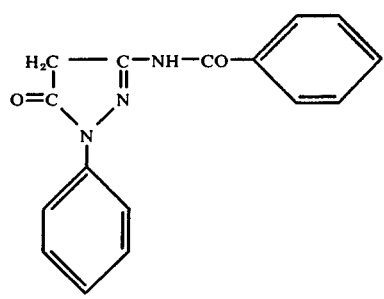
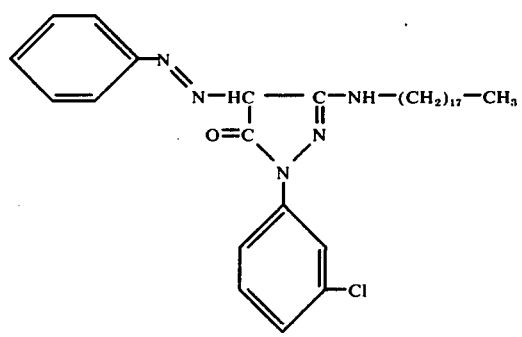
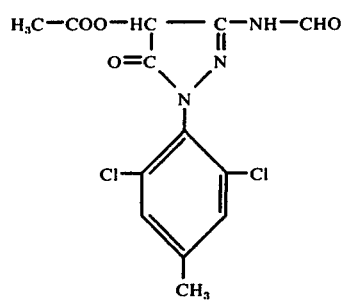
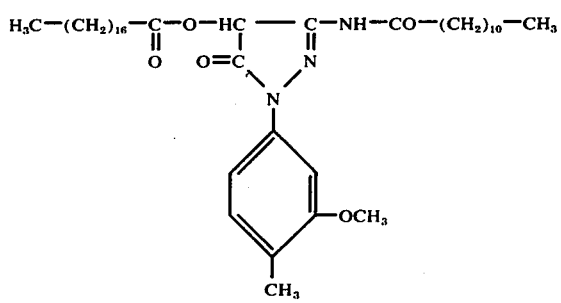
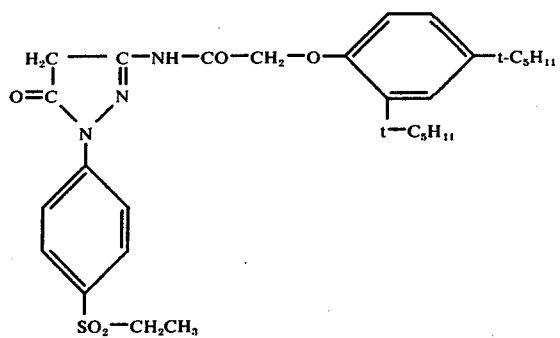

-continued
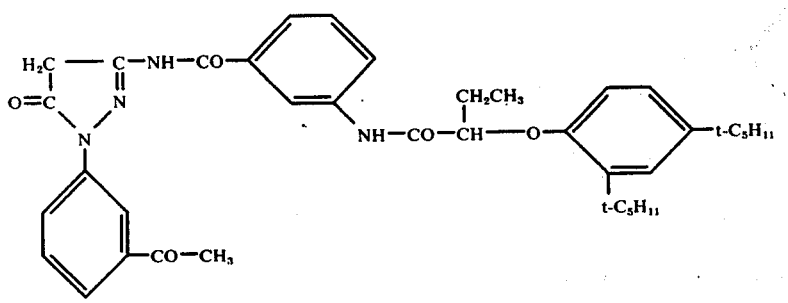
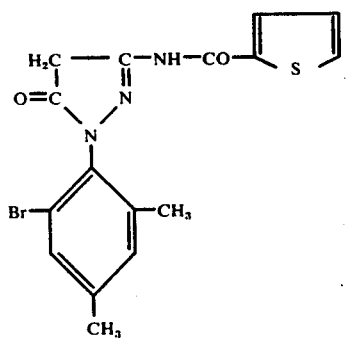
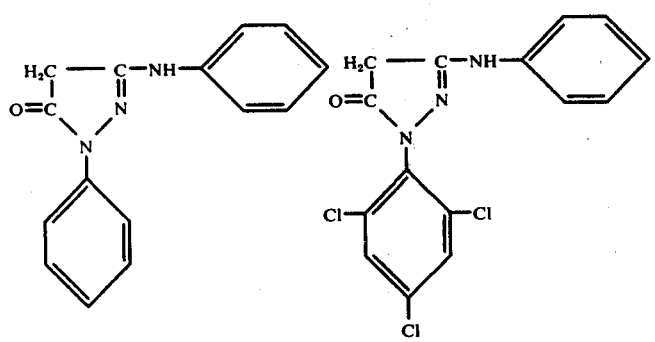
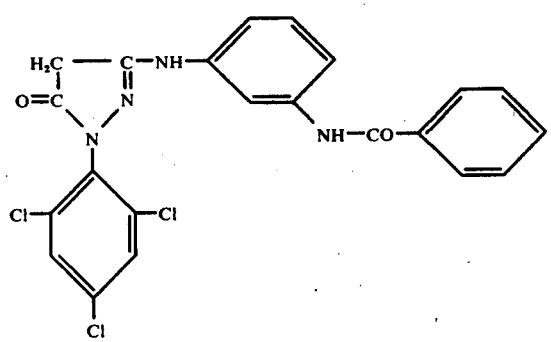
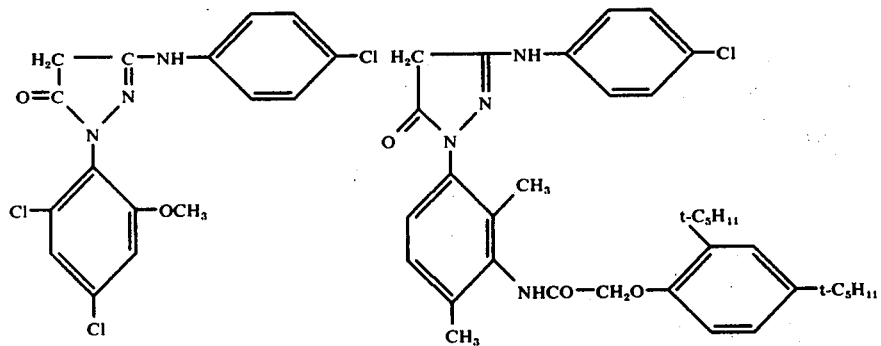

-continued
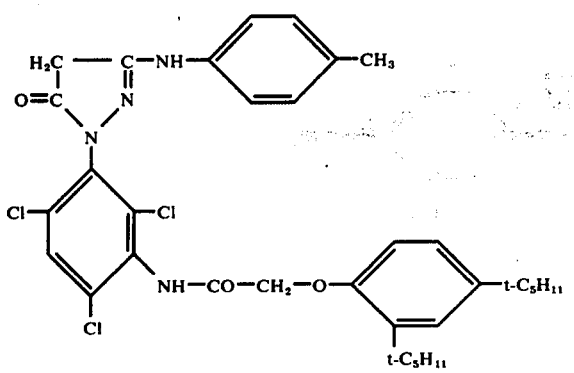
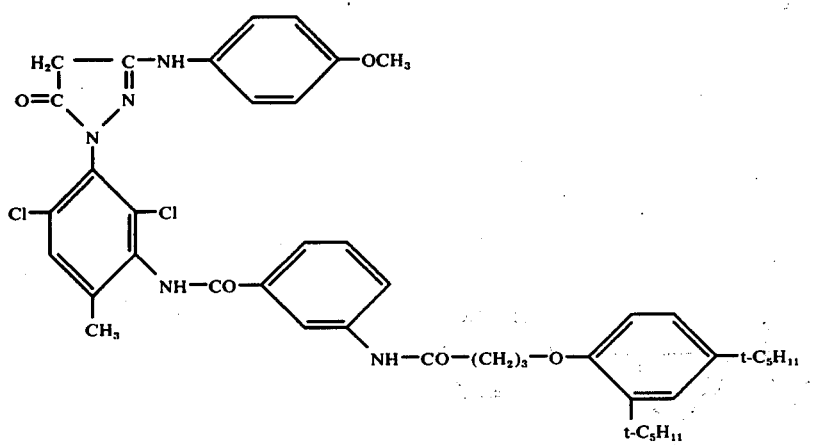
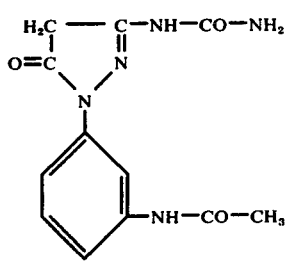
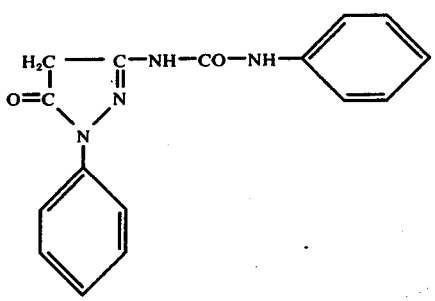
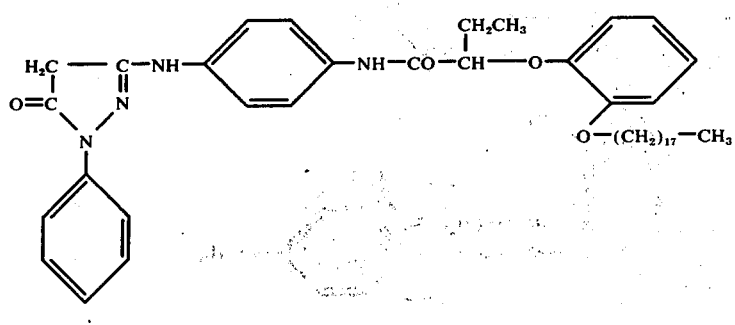

-continued
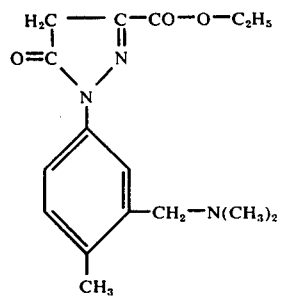
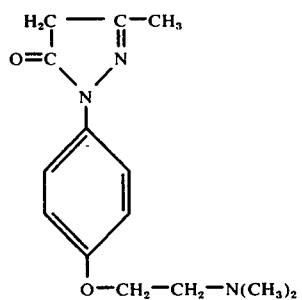
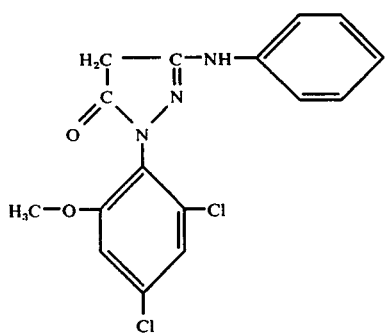
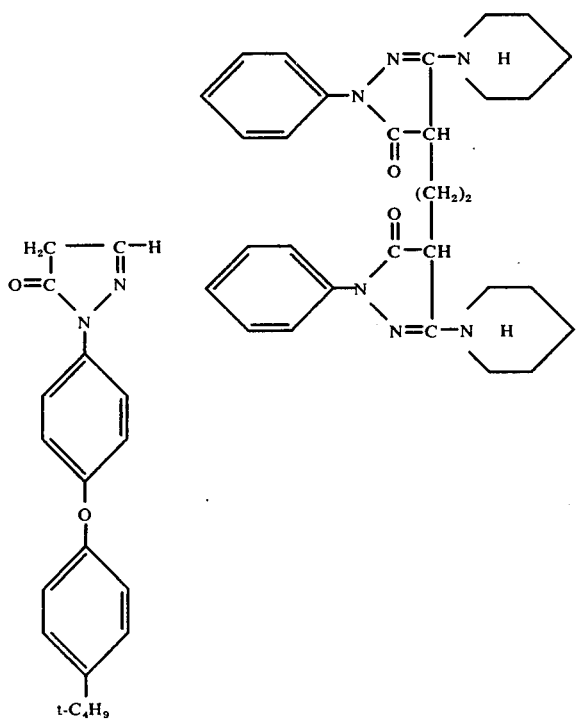

-continued
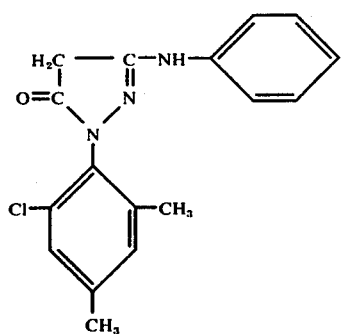
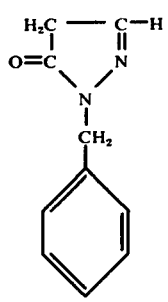
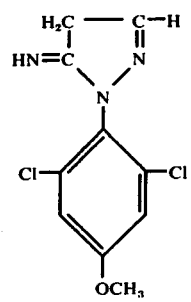
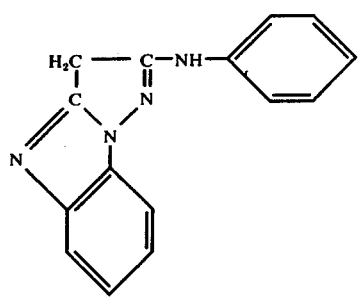
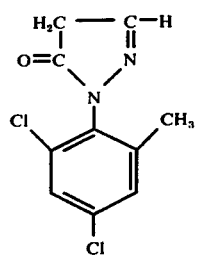
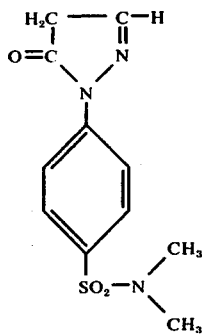

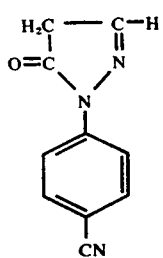
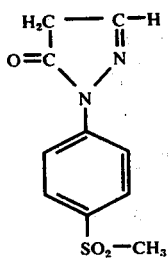
-continued
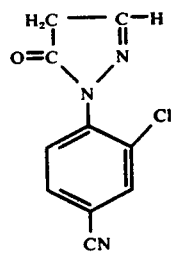
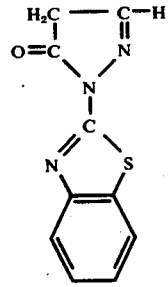
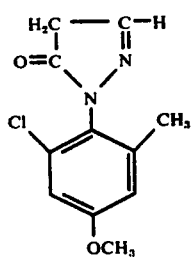
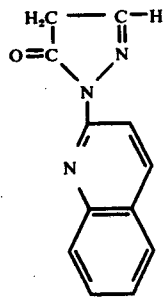
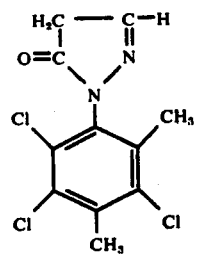
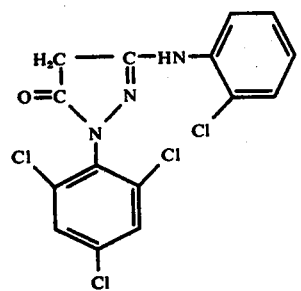
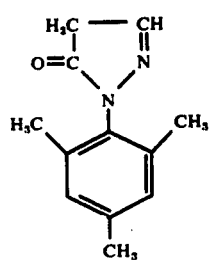
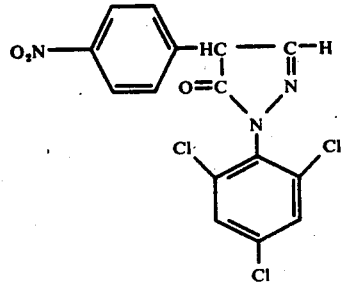
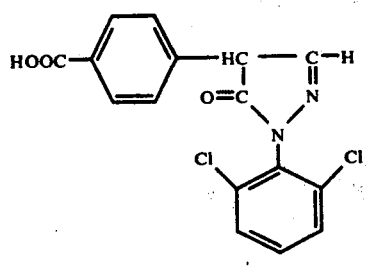

-continued
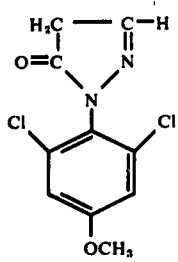 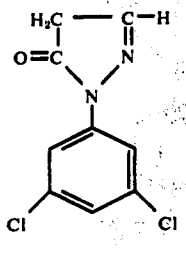
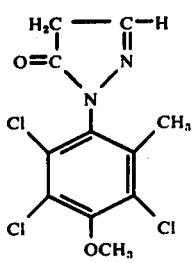 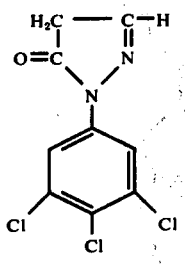
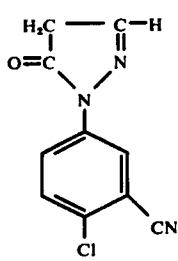 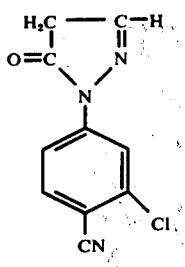
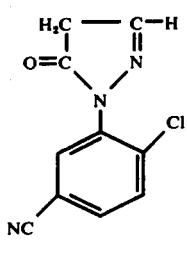 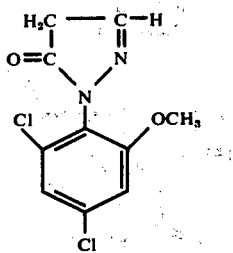
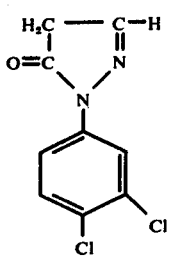 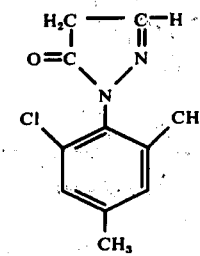
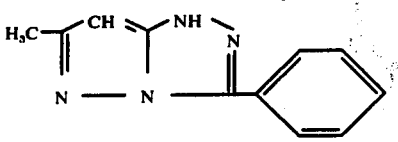
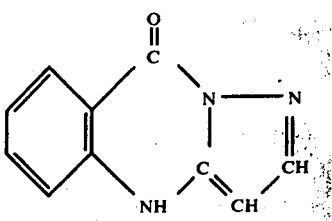

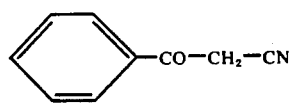
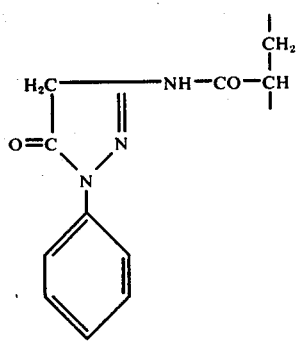
Polymer with units of the formula
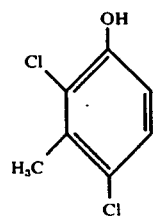 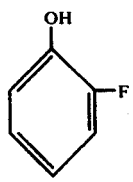 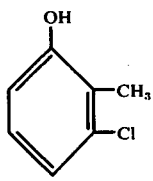
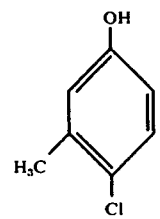
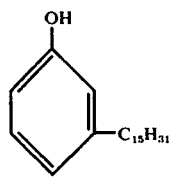  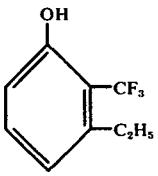
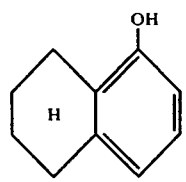
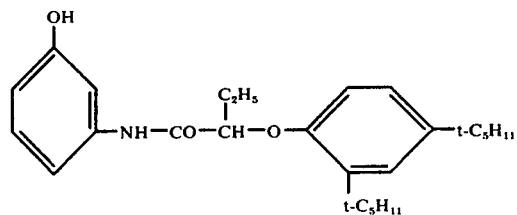
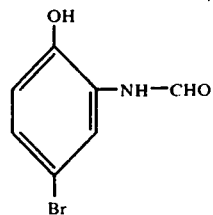

-continued
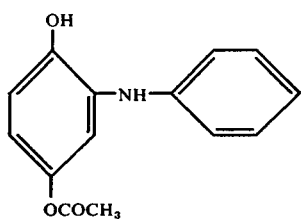
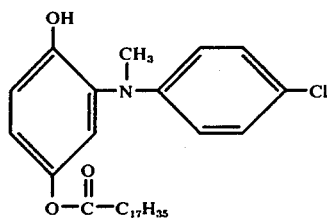
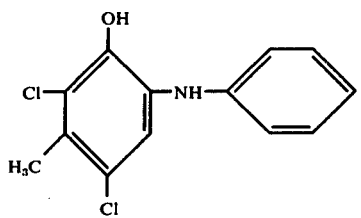
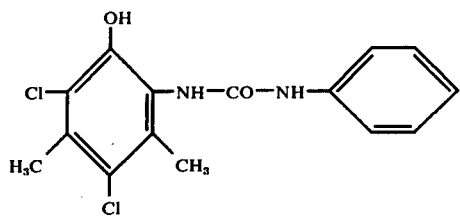
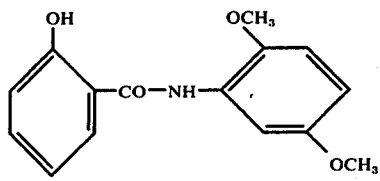
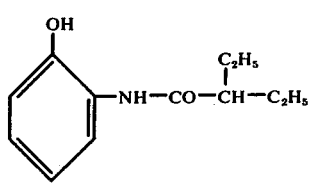
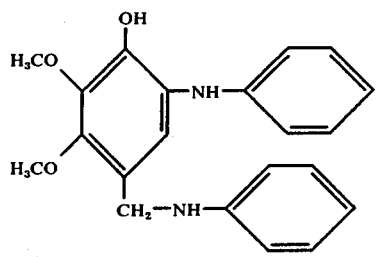

-continued
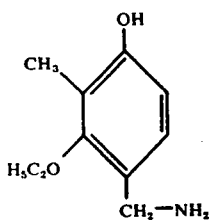
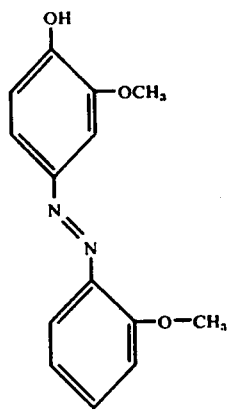
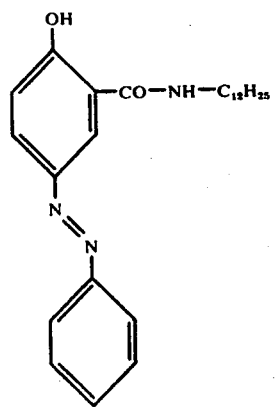
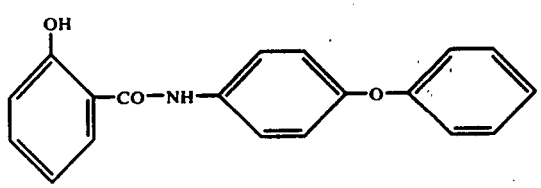
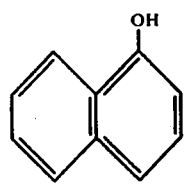

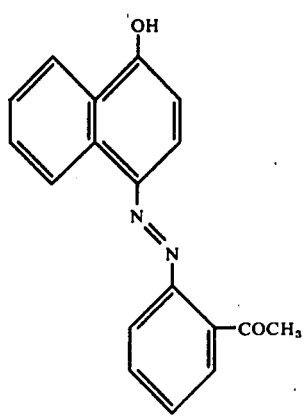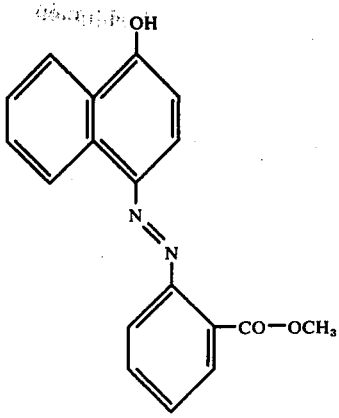
-continued
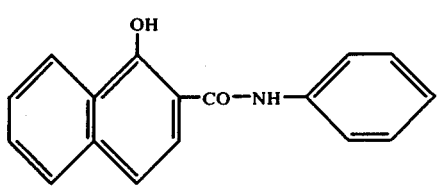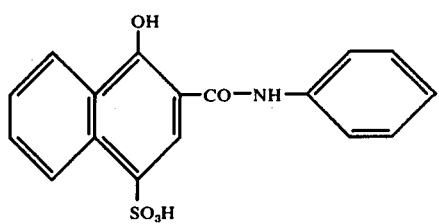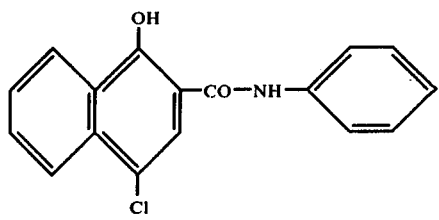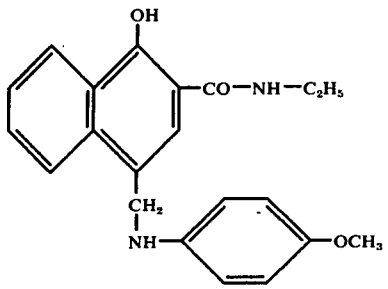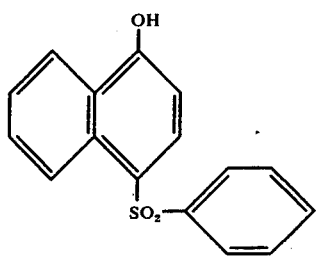

-continued
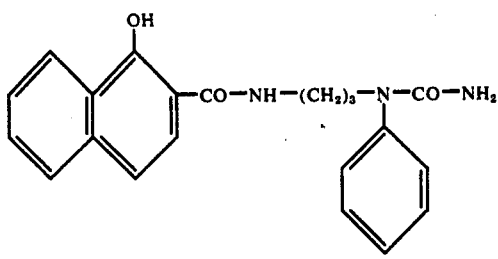
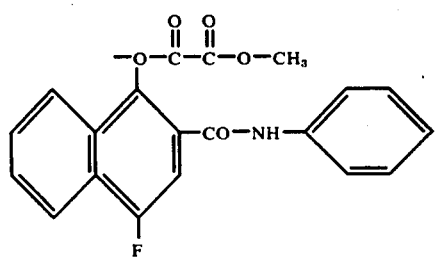
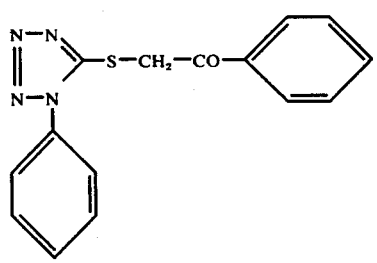
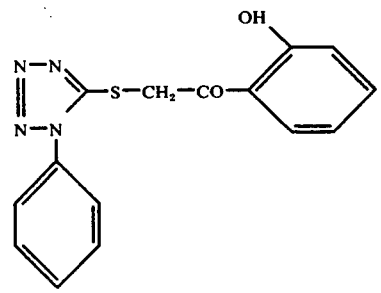
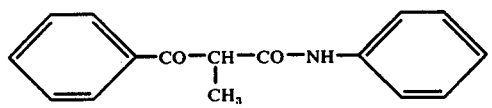
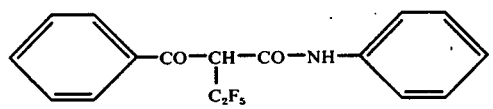
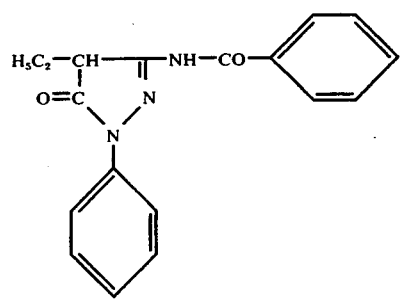

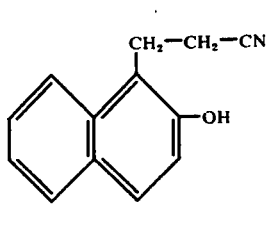
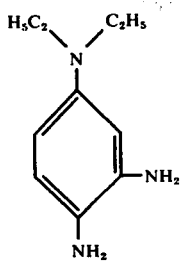
The phosphonic acid radicals and phosphoric acid radicals of the compounds according to the invention are derived, for example, from compounds of the following formulae:
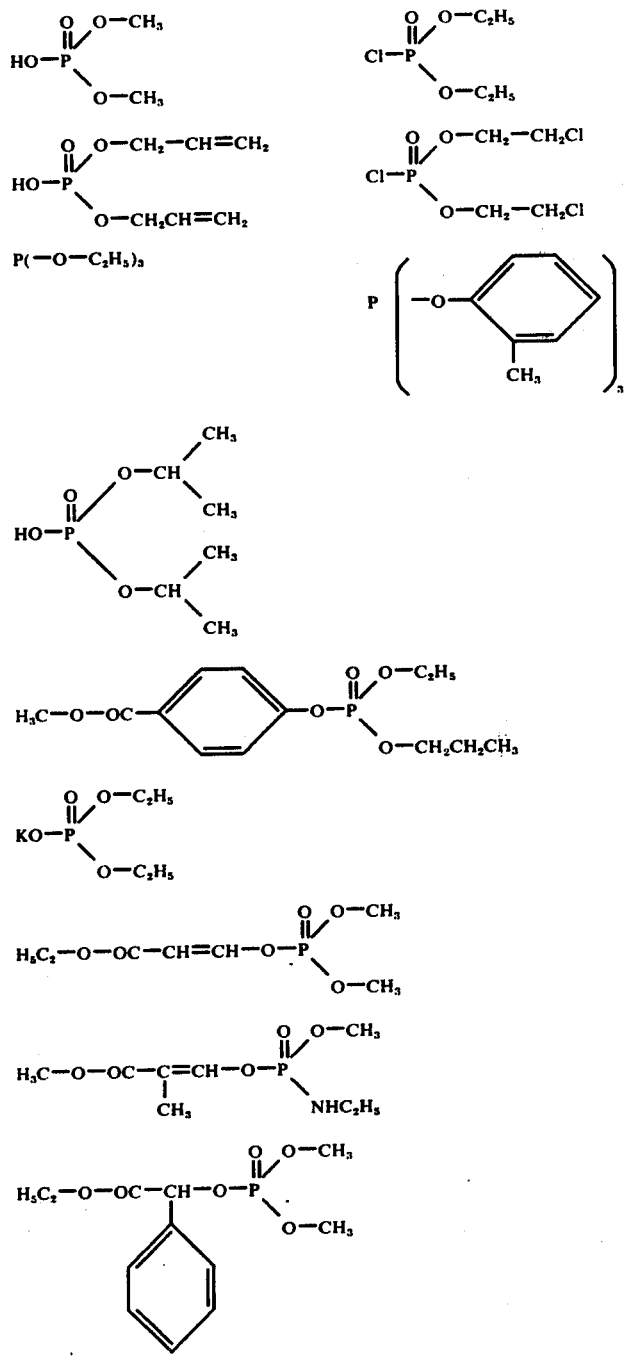

-continued
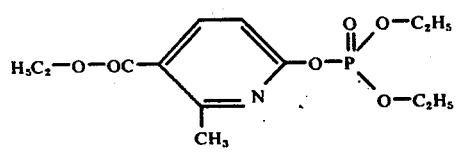
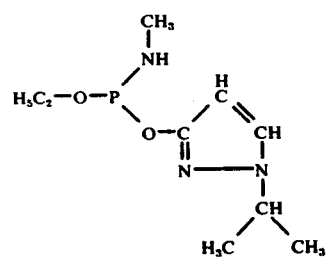
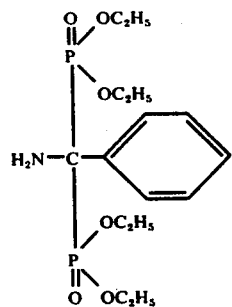
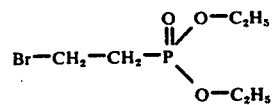
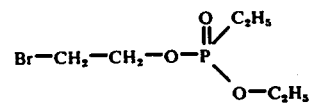
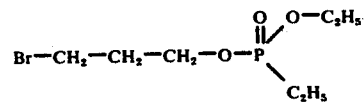
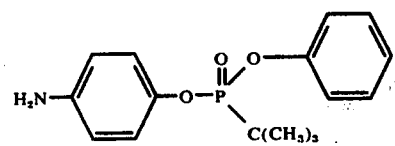
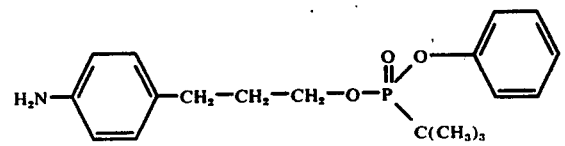
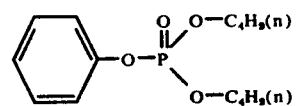
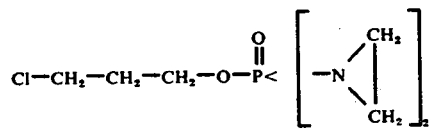

-continued
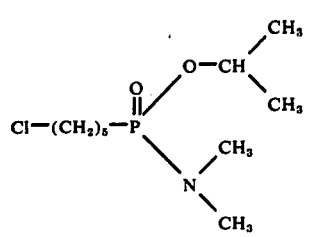
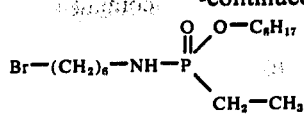
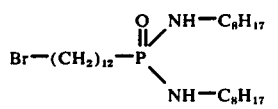
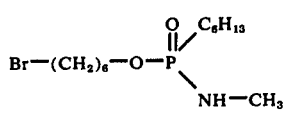
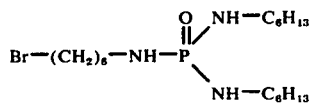
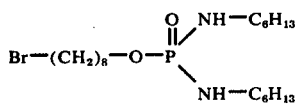
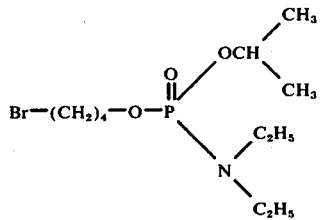
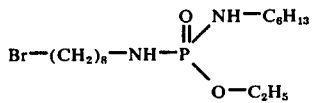
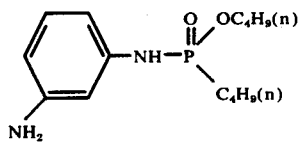
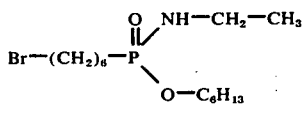
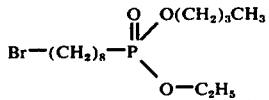
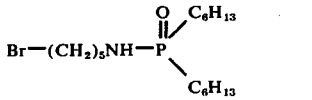
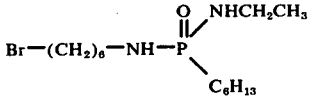
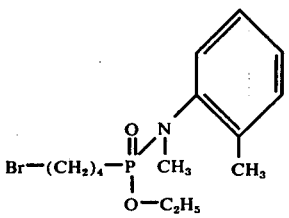
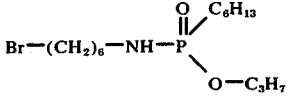
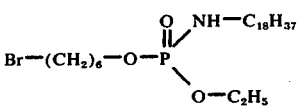
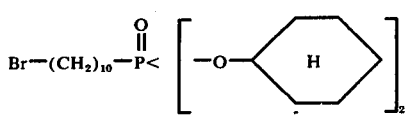
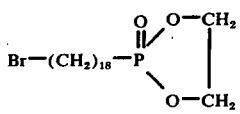

-continued
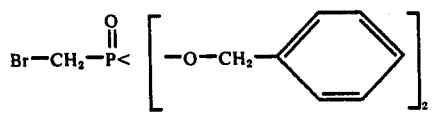
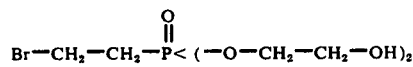
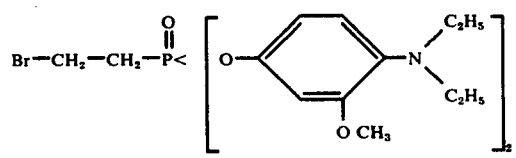
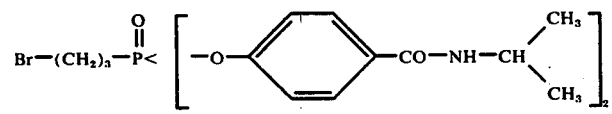
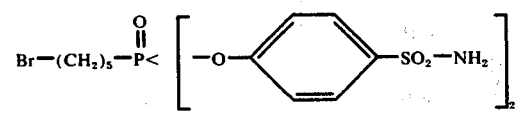
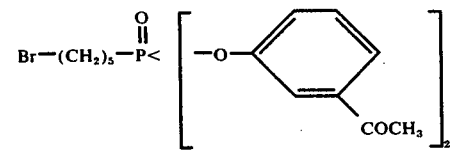
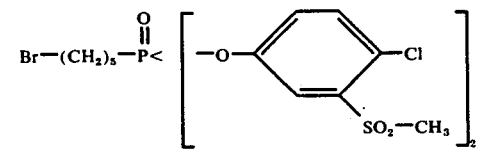
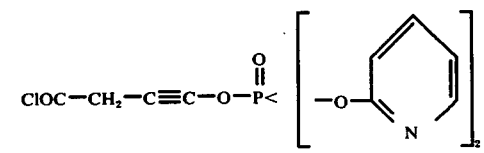
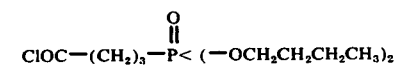
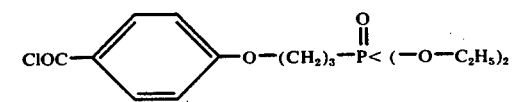
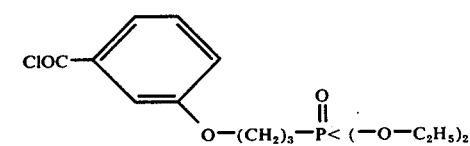
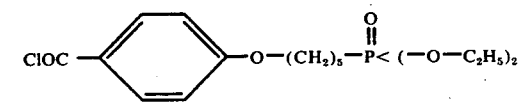

-continued
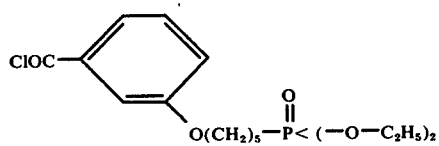
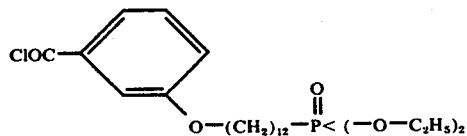
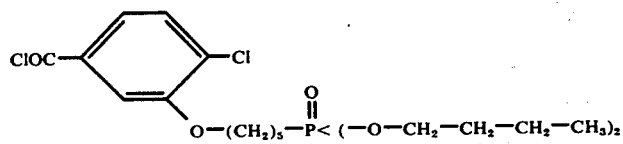
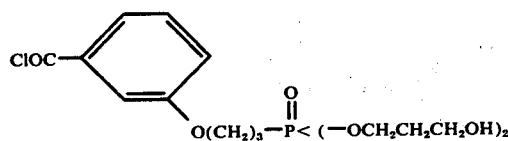
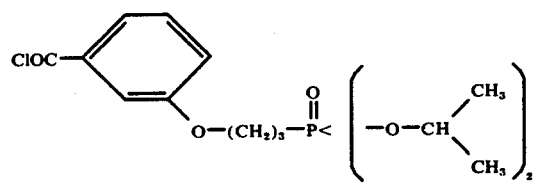
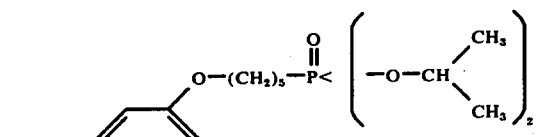
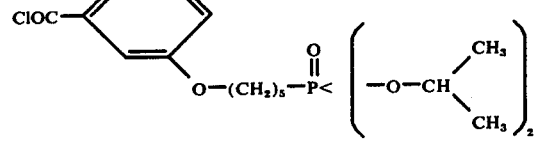
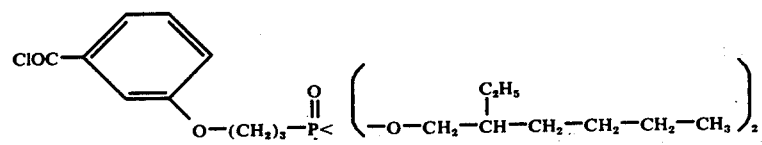
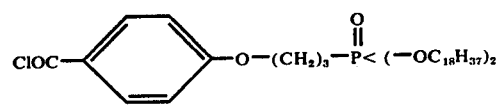
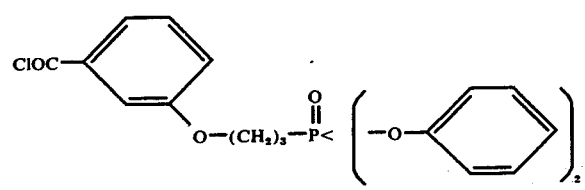

-continued
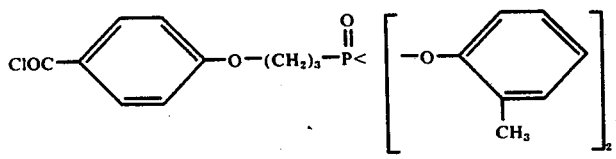
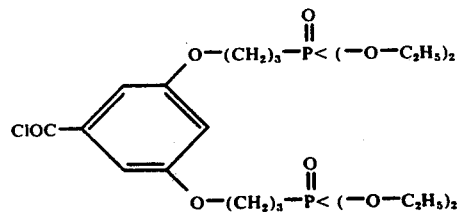
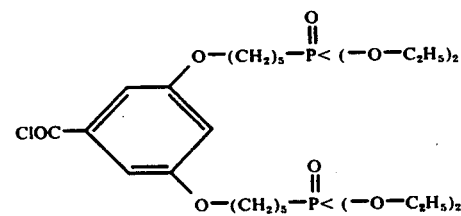
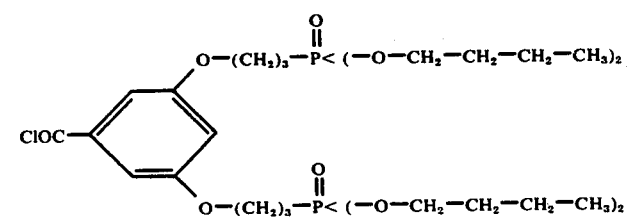
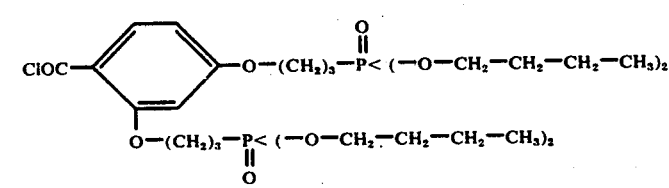
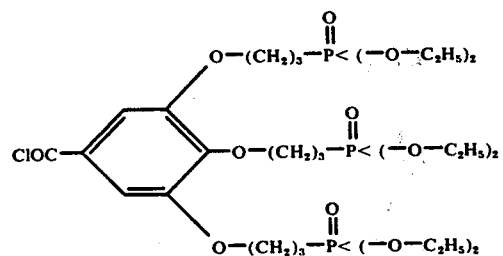
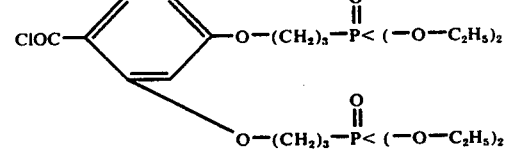
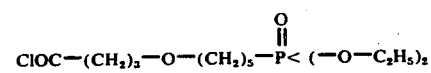
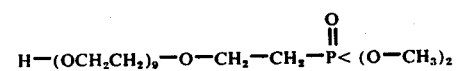

-continued
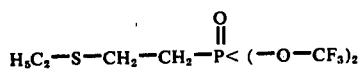
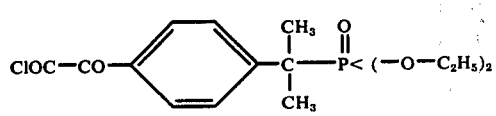
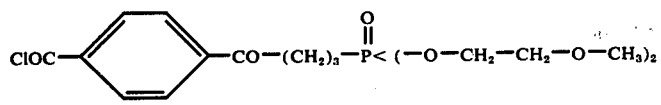
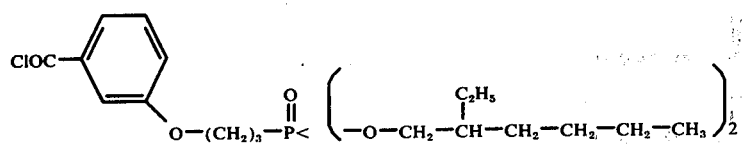
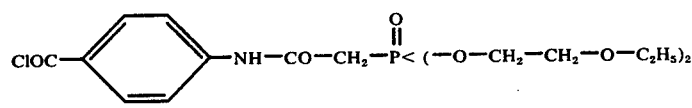
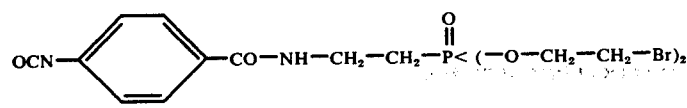
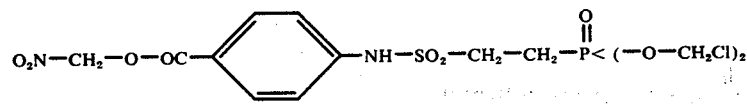
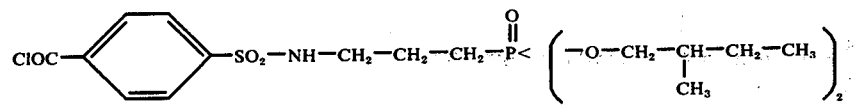
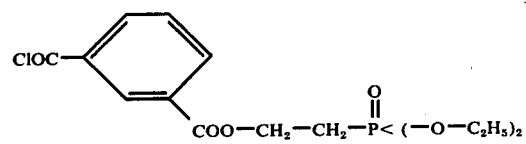
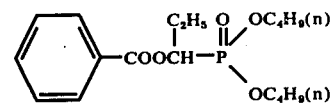
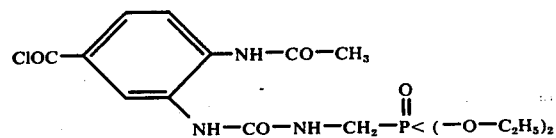
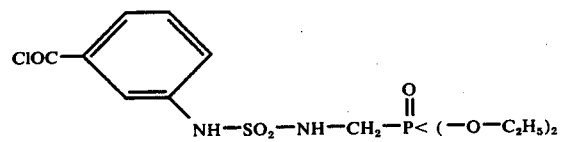
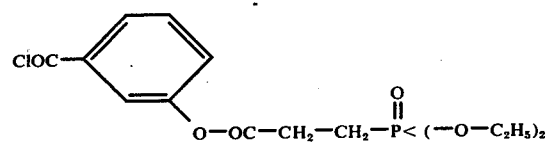

-continued
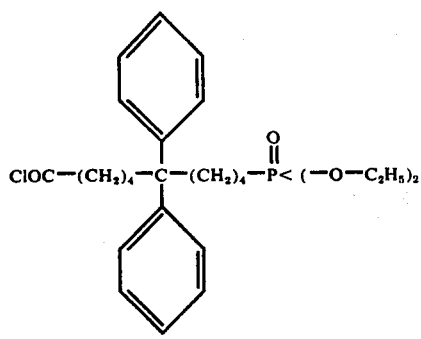
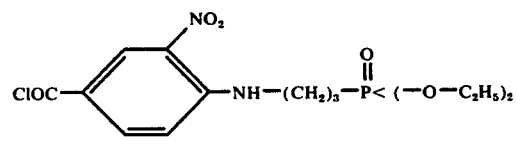
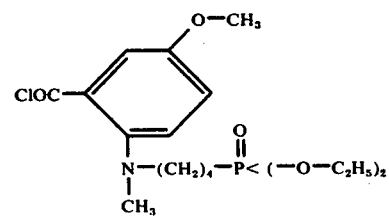
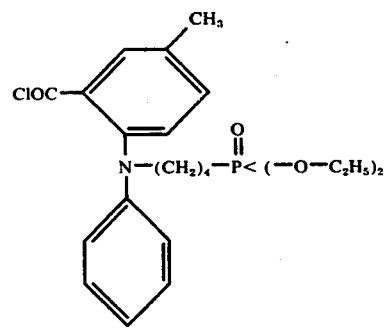
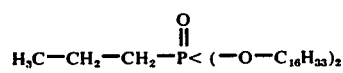
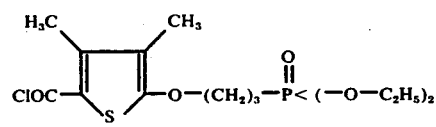
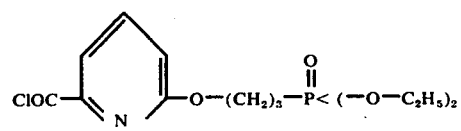
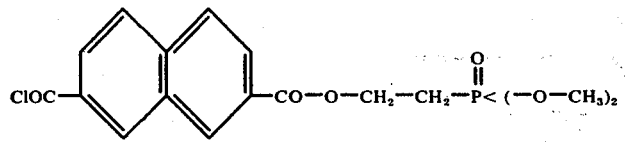

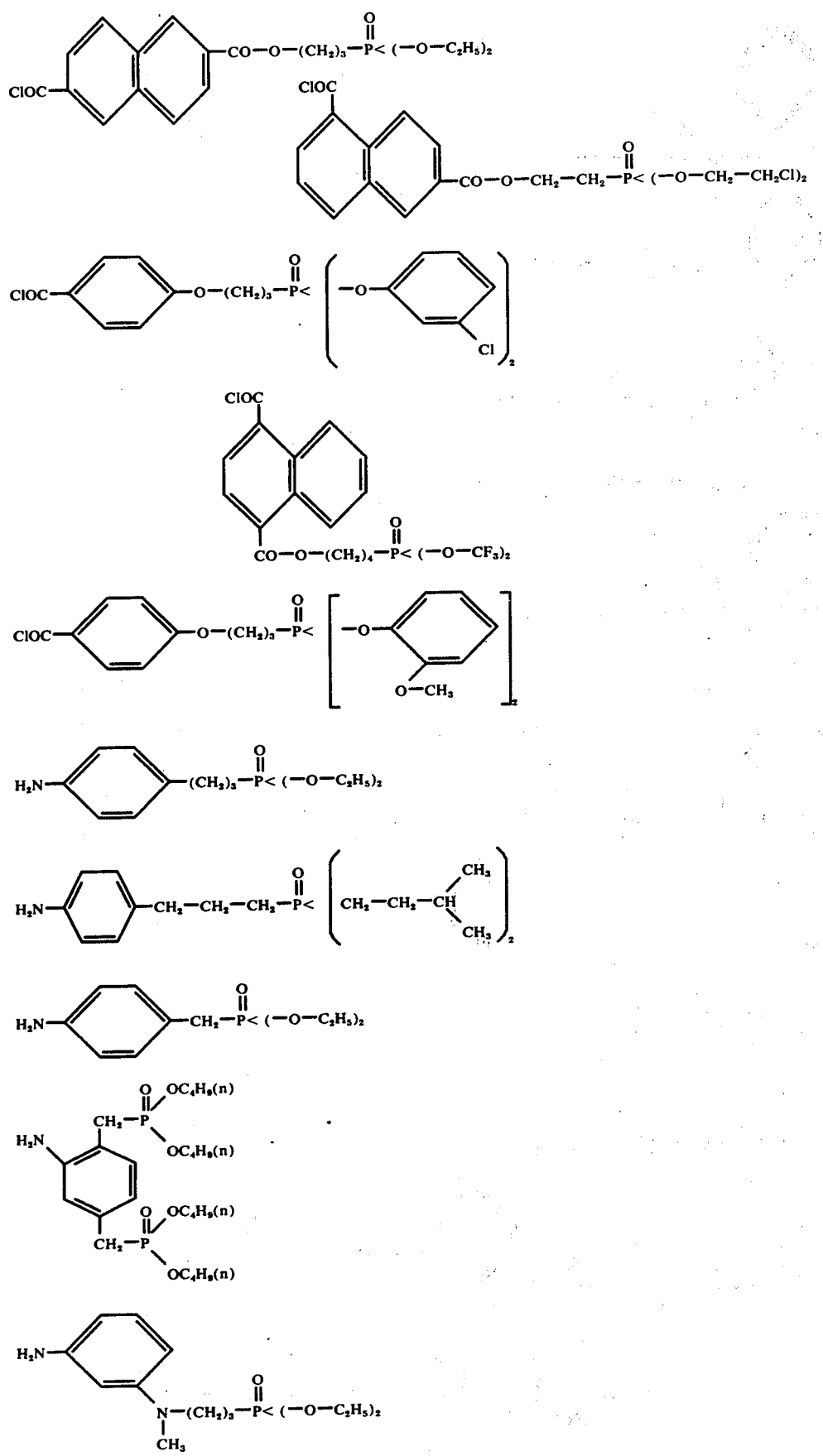

-continued
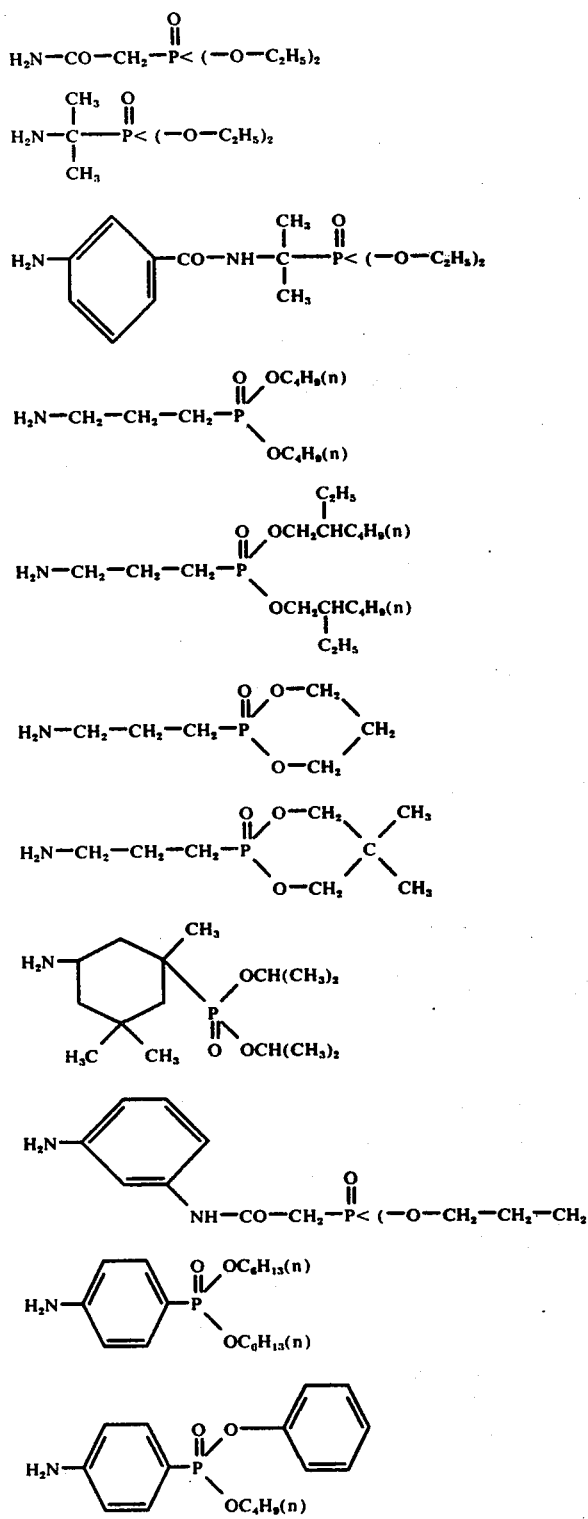
The phosphonic acid radicals of the compounds according to the invention are preferably derived from compounds of the following formulae:

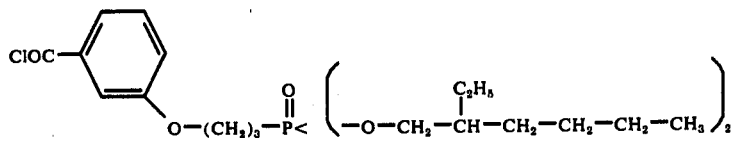

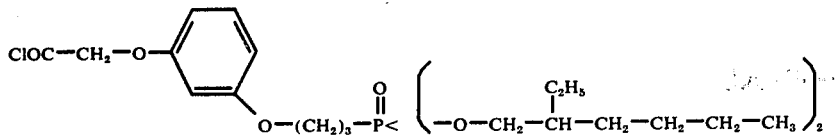

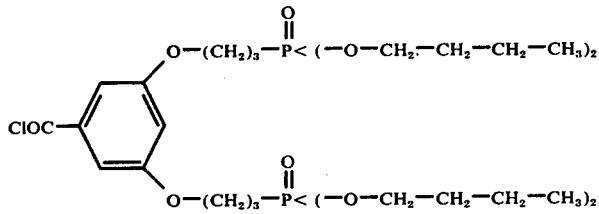

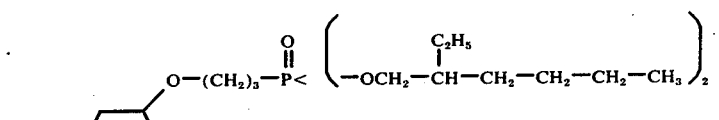

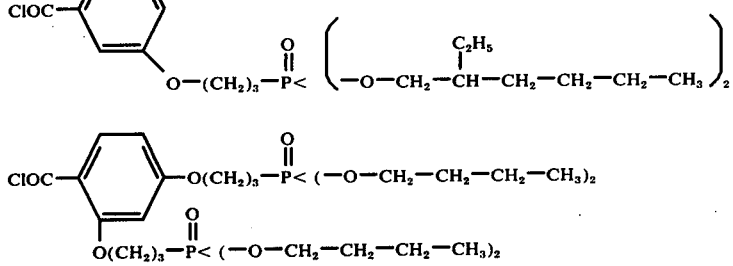

The alkoxy groups —O—R$_1$ and —R$'_1$ and further radicals which are possible in place of these alkoxy groups are derived, for example, from the following hydroxy compounds: methanol, 1-propanol, 1-hexanol, 1-decanol, 1-tetradecanol, 1-octadecanol, 2-propanol, 2-octanol, 2-methyl-2-propanol, 3-chloro-1-propanol, 3-methoxy-1-butanol, benzyl alcohol, 2-phenylethanol, oleyl alcohol, 3-fluorophenol, 2-chlorophenol, 4-methoxyphenol, 2-amino-4-iodophenol, 2,4,5-trimethyl-phenol, 4-tert.-butoxyphenol, ethanol, 1-butanol, 1-octanol, 1-dodecanol, 1-hexadecanol, 1-hexaeicosanol, 2-butanol, 3-octanol, 2-ethyl-1-hexanol, 3-bromo-1-propanol, cyclohexanol, 1-phenylethanol, allyl alcohol, α-3,7-dimethyl-1,6-octadien-3-ol, 2-methylphenol, 3-methylphenol, 4-methylphenol, 4-bromo-2-nitrophenol, 3-dimethylaminophenol, 3-acetylaminophenol, ethylene glycol, ethylene glycol monoisopropyl ether, ethylene glycol monophenyl ether, ethylene glycol monomethyl ether, ethylene glycol mono-4-chlorophenyl ether, 1,2-propanediol, 1,3-propanediol, 1,3-butanedial, 1,4-butanediol and 2-mercaptoethanol.

The compounds according to the invention are outstandingly suitable for use in light-sensitive silver halide emulsion layers of single-layer or multi-layer materials for colour photograph. However, it is not essential that the coupling agents should be incorporated into the light-sensitive silver halide emulsion layers; rather, it is also possible to accommodate them in a light-insensitive or light-sensitive binder layer which adjoins a light-sensitive silver halide emulsion layer.

The coupling agents according to the invention can be incorporated into a silver halide emulsion or into another binder mixture according to one of the known methods. Appropriately, the following procedures are used for this purpose:

a. Dissolving the coupling agent in a sparingly water-soluble organic solvent of low volatility (boiling point, for example, above 200° C) and dispersing the coupling agent solution directly in a photographic emulsion or dispersing the coupling agent solution beforehand in an aqueous medium and subsequently adding the dispersion to a photographic emulsion. Di-n-butyl phthalate, tricresyl phosphate, N,N-diethylcaproic acid amide, lauric acid dimethylamide, dibutylsulphone or N,N-dibutylurea are examples of such organic solvents.

On this topic see, for example, U.S. Patent Specifications 2,304,939, 2,304,940 and 2,322,027.

b. Dispersing the couping agent according to the invention in solvents of the so-called natural resin type, that is to say, for example, in solvents of the nature known from U.S. Pat. Spec. No. 2,284,879.

c. A relatively water-insoluble low-boiling solvent is used as in the case of (a) but is intended to be removed during one of the last stages. Ethyl acetate, methylene chloride, chloroform and cyclohexanone are used as such solvents.

d. A water-miscible organic solvent is used, which can be removed during one of the last states or can remain in the photographic material. Examples of such organic solvents are dimethylformamide, dimethylsulphoxide, N-methylpyrrolidone, methanol and ethanol.

With regard to (c) and (d) see, for example, U.S. Pat. Spec. Nos. 2,801,170, 2,801,171 and 2,749,360.

e. Heating and fusing the coupling agent without using an organic solvent and dispersing the fused coupling agent directly in a photographic emulsion or in an aqueous medium. This procedure is suitable for coupling agents melting below 85° C.

In some cases, the organic solvents mentioned under (a), (b), (c) and (d) can be mixed in order to obtain a good dispersion of the coupling agent.

f. Finally, the coupling agents can also be dissolved in solutions of polymerisable monomers, after which the monomers are polymerised, for example in the presence of gelatine, giving dispersions of the colour coupling agents in the polymers. On this matter, reference may be made, for example, to the process known from U.S. Patent Spec. No. 2,825,382.

To prepare a photographic emulsion layer it is furthermore also possible to use one or more coupling agents of the formula (1) together with a known coupling agent. Suitable light-sensitive emulsions are emulsions of silver halides such as silver chloride, silver bromide or mixtures thereof, optionally containing a small amount - up to 10 mol % - of silver iodide, in one of the customary hydrophilic binders such as a protein, especially gelatine, polyvinyl alcohol, polyvinylpyrrolidone, cellulose derivatives, such as carboxyalkylcellulose, especially carboxymethylcellulose, or derivatives of alginic acid. The nature of the photographic silver halides is immaterial in relation to the invention.

The emulsions can also be chemically sensitised, for example by addition of compounds containing sulphur, for example allyl isothiocyanate, allyl thiourea, sodium thiosulphate and the like, during the chemical ripening. Other chemical sensitisers which can be used are reducing agents, for example the tin compounds described in Belgian Patent Specs. Nos. 493,464 or 568,687, and also polyamines such as diethylenetriamine, or aminomethanesulphinic acid derivatives, for example according to Belgian Pat. Spec. No. 547,323.

Further suitable chemical sensitisers are noble metals or noble metal compounds such as gold, platinum, palladium, iridium, ruthenium or rhodium. This method of chemical sensitisation is described in the article by R. Koslowsky, Z. Wiss. Phot. 46, 65–72, (1951).

It is, furthermore, possible to sensitise the emulsions with polyalkyleneoxy derivatives, for example with a polyethylene oxide of molecular weight between 1,000 and 20,000, or with condensation products of alkylene oxides and aliphatic alcohols, glycols, cyclic dehydration products of hexitols, alkyl-substituted phenols, aliphatic carboxylic acids, aliphatic amines, aliphatic diamines and amides. The condensation products have a molecular weight of at least 700, and preferably of more than 1,000. To achieve special effects, these sensitisers can of course also be used in combination, as described in Belgian Pat. No. Spec. 537,278 and in British Pat. Spec. No. 727,982.

The emulsions containing colour coupling agents can furthermore contain spectral sensitisers, for example the customary monomethine or polymethine dyestuffs, such as cyanines, hemicyanines, streptocyanines, merocyanines, oxonols, hemioxonols, styryl dyestuffs or others, and also trinuclear or polynuclear methine dyestuffs, for example rhodacyanines or neocyanines. Such sensitisers are described, for example, in the work by P.M. Hamer "The Cyanine Dyes and Related Compounds", Interscience Publishers John Wiley and Sons, 1964.

However, the invention is not restricted only to colour-photographic materials with several different spectrally sensitised silver halide emulsions but also relates to colour-photographic materials which contain mixed grain emulsions.

The emulsions can contain the customary stabilisers, such as, for example, homopolar or salt-like compounds of mercury with aromatic or heterocyclic rings, such as mercaptotriazoles, simple mercury salts, sulphonium-mercury double salts and other mercury compounds. Further suitable stabilisers are azaindenes, preferably tetraazaindenes or pentaazaindenes, especially those substituted by hydroxyl or amino groups. Such compounds are described in the article by Pirr, Z. Wiss. Phot. 47, 2-58 (1952). Further suitable stabilisers are, inter alia, heterocyclic mercapto compounds, for example phenylmercaptotetrazole, quaternary benzthiazole derivatives, benztriazole and the like.

The silver halide emulsions can also contain yet further photographic auxiliaries, for example coating auxiliaries, such as lubricants and wetting agents, or antistatic agents.

The emulsions can be hardened in the usual manner, for example by means of metal salts such as zirconyl sulphate or chromium triacetate, or by means of organic compounds such as formaldehyde, halogen-substituted aldehydes which contain a carboxyl group, such as mucobromic acid, diketones, dialdehydes, methanesulphonic acid esters, epoxides, heterocyclic compounds, especially azines, such as triazines, or pyrimidines with suitable removable groups, such as halogen atoms, alkoxy groups, alkylsulphonyl groups or groups with a quaternary nitrogen atom, aziridine compounds or compounds which contain a double bond activated by a —CO— or —SO$_2$— group, such as bis-acrylamides and the like.

The new coupling agents react very well with the oxidation product of all customary developers of the type of p-phenylenediamine such as, for example, N,N-diethyl-p-phenylenediamine, N,N-diethyl-3-methyl-p-phenylenediamine, 4-amino-3-methyl-N-ethyl-N-$\beta$(-methanesulphenamide)ethyl aniline, N-ethyl-N($\beta$-hydroxyethyl)-p-phenylenediamine, N-ethyl-N-$\beta$-hydroxyethyl-3-methyl-p-phenylenediamine and N-butyl-N-$\delta$-sulphobutyl-p-phenylenediamine. Further usable colour developers are described, for example, in J. Am. Chem. Soc. 73, 3000-3025 [1951].

The same also applies to the case of the new coupling agents being used in the form of phenylazo derivatives (mask coupling agents for negative materials, see U.S. Patent Spec. No. 2,449,966).

In addition to the said developer compounds, the colour developers used for developing colour-photographic recording materials according to the invention can also contain compounds which control the developing process, such as, for example, citracinic acid and the like. In addition, a durable colour image is obtained with a colour-photographic recording material containing a coupling agent according to the invention if a UV absorber is incorporated into the material, for example a benzophenone compound such as 4-phenyl-2'-hydroxy-4'-octyloxy-benzophenone, a triazole compound, for example 2-(2'-hydroxy-3', 5'-di-tert.-butyl- or -di-tert.-amyl-phenyl)benztriazole, or a resorcinyl-triazine compound, such as 2 -phenyl-4,6-di[2'-hydroxy-4'-(ω-carboethoxy-pentyloxy)]1,3,5-triazine.

The material according to the invention can also contain an optical brightener, for example a stilbene derivative.

It is also possible to employ the colour coupling agents according to the invention as so-called single developer-coupling agents in a colour developing bath, instead of employing them in photographic layers. The colour-photographic material employed in that case then preferably does not contain a built-in colour coupling agent in at least one of the silver halide emulsion layers present. Such processes are described, for example, in the following patent specifications: U.S. Pat. Specs. No. 2,113,329, 2,252,718, 2,343,703 and 3,002,836, Belgian Pat. Spec. No. 672,255, German Auslegeschrift 1,176,478, German Offenlegungsschrift 2,062,350 and British Patent Spec. No. 680,488.

To manufacture the recording materials, it is furthermore possible to use customary known layer carriers, for example films of cellulose nitrate, cellulose acetate, polyvinyl acetal, polystyrene, polyethylene terephthalate, polyethylene and polypropylene, but also layer carriers of paper, glass and the like. The layer carriers can furthermore also consist of paper or some other fibrous material which is provided with a hydrophobic surface which is waterrepellent and neither absorbs nor adsorbs water. Layer carriers with a hydrophobic surface can furthermore carry hydrophobic resin layers which have been subjected to electron irradiation, as is known, for example, from British Pat. Spec. Nos. 971,058 and 1,060,526, and U.S. Pat. Spec. Nos. 2,864,755 and 2,864,756, in order to improve the adhesion of layers of hydrophilic colloid. Such resin layers can optionally also be used in the form of self-supporting layers. Typical layer carriers wih suitable hydrophobic surfaces are, for example, layer carriers of polyethylene terephthalate films, which have been irradiated with electrons in such a way that they have a contact angle of less than 45° (compare U.S. Pat. Spec. No. 3,220,842), or which have an electron-irradiated surface carrying a chromium halide (compare U.S. Pat. Spec. No. 3,117,865), or which are layer carriers of paper possessing a hardened gelatine layer which has been irradiated with electrons, as is known, for example, from Belgian Pat. Spec. No. 671,661.

The layer carriers can optionally contain customary known additives, for example pigments, for example titanium dioxide and/or antistatic compounds, as is known, for example, from U.S. Pat. Spec. No. 3,253,922. Colour-photographic recording materials of particular importance are those which consist of at least 3 superposed emulsion layers of different spectral sensitisation. To manufacture such recording materials, the layer carrier can first be coated with, for example, a layer sensitive to red, then with a layer sensitive to green and finally with a layer sensitive to blue, with or without a Carey-Lea filter layer between the layer sensitive to blue and the layer sensitive to green. The three layers of different colour sensitisation can however also be superposed in a different sequence except that the Carey-Lea filter layer must not be located above the layer sensitive to blue. Advantageously, the light-sensitive layers are located on the same side of the layer carrier. The recording material can optionally possess intermediate layer and/or covering layers, in a customary known manner.

The components according to the invention can be employed either in the negative-positive process or in the reversal process.

The coupling agents according to the invention are above all distinguished by excellent solubility and a low tendency to crystallise in organic solvents, especially in water-immiscible solvents of high boiling point such as, for example, tricresyl phosphate isomer mixture or dibutylphthalate.

In addition, they have excellent diffusion resistance in photographic layers, both during the casting process and during photographic processing.

A particular advantage of the ballast groups containing phosphorus is that in comparison to long-chain or branched hydrophobic alkyl radicals, they give substantially improved hydrophilic properties. This expresses itself, inter alia, by a high coupling activity. With regard to the advantages of hydrophilic groups in oil-soluble coupling agents, see also German Offenlegungsschrift 1,958,303.

The combination of excellent solubility in organic solvents and excellent diffusion-resistance, on the one hand, with good compatibility with water, on the other, is a particularly surprising unforeseeable property of the coupling agents according to the invention. A further advantage of the coupling agents according to the invention resides in the fact that they are easy to manufacture and that the requisite phosphorus-containing starting products are readily accessible. In colour development, the new coupling agents give colour images of excellent fastness to light and advantageous spectral absorption, suitable for photographic applications.

The colour-photographic material which is manufactured using such a new coupling agent is therefore characterised by good photographic properties, good colour reproduction, adequate stability before and after the treatments, and ease of manufacture.

As can be seen from Table A which follows, the compounds according to the invention display a substantially greater solubility in oil (at 20° C) than do the known coupling agents.

TABLE A

| Compound | Described in | Solubility in g per g of tricresyl phosphate |
|---|---|---|
| [structure: phenyl-CO-CH₂-CO-NH-phenyl with N(C₄H₉(n))₂ and SO₂-NH-C₁₈H₃₇ substituents] | DT-OS 1,522,414 | 1.2 |
| [structure: o-methylphenyl-CO-CH₂-CO-NH-phenyl-NH-CO-CH₂-CH₂-O-phenyl-OC₁₀H₂₁] | DT-OS 2,039,970 | 1 |
| [structure: t-C₁₂H₂₅-S-CH₂-CONH-phenyl-CO-CH₂-CO-NH-phenyl with COOC₂H₅ and OCH₃ substituents] | DT-OS 1,804,167 | 1 |
| [structure: pivaloyl-CH(O-CO-(CH₂)₃-[2-(2H-benzotriazol-2-yl)-4-ethyl-6-hydroxyphenyl])-CO-NH-phenyl-NH-CO-C(CH₃)₂-O-phenyl with t-C₅H₁₁ and OC₅H₁₁ substituents] | DT-OS 2,216,578 | 2 |
| Table I, No. (109) | The present description | > 5 |
| Table I, No. (128) | The present description | > 5 |
| Table I, No. (135) | The present description | > 5 |
| [structure: 3,5-dichloro-4-methyl-2-hydroxyphenyl-NH-CO-CH(C₂H₅)-O-phenyl with 2-t-C₅H₁₁ and 4-t-C₅H₁₁ substituents] | US-PS 2,801,171 Coupling agent No. (4) | 0.4 |
| [structure: 3,5-dichloro-4-methyl-2-hydroxyphenyl-NH-CO-CH(C₂H₅)-O-phenyl-n-C₁₅H₃₁] | US-PS 2,908,573 Coupling agent of the formula 2 | 0.7 |

TABLE A-continued

| Compound | Described in | Solubility in g per g of tri-cresyl phosphate |
|---|---|---|
| [Structure: 3-chloro-5-chloro-4-methyl-2-hydroxyphenyl-NH-CO-CH(C₂H₅)-O-phenyl-O-n-C₁₂H₂₅] | GB-PS 1,290,423 Coupling agent of the formula (15) | 0.7 |
| Example, formula (701) | The present description | Miscible in all proportions |
| [Structure: pyrazolone with 2,4,6-trichlorophenyl, NH-CO-phenyl-NH-CO-CH₂-O-phenyl with t-C₅H₁₁ groups] | US-PS 2,600,788 Coupling agent of the formula (7) | 0.6 |
| [Structure: pyrazolone with 2,4,6-trichlorophenyl, NH-CO-phenyl-NH-CO-CH(C₂H₅)-O-phenyl-n-C₁₅H₃₁] | US-PS 2,908,573 Coupling agent of the formula (7) | 0.3 |
| [Structure: pyrazolone with 2,4,6-trichlorophenyl, NH-CO-phenyl-NH-CO-CH(C₂H₅)-O-phenyl-O-n-C₁₂H₂₅] | GB-PS 1,290,423 Coupling agent of the formula (9) | 0.4 |
| Table II, No. (231) | The present description | Miscible in all proportions |
| Table II, No. (236) | The present description | Miscible in all proportions |
| Table II, No. (240) | The present description | Miscible in all proportions |
| Table II, No. (243) | The present description | Miscible in all proportions |
| Table II, No. (248) | The present description | Miscible in all proportions |
| Table II, No. (251) | The present description | Miscible in all proportions |
| Table II, No. (266) | The present description | Miscible in all proportions |

MANUFACTURING EXAMPLES

EXAMPLE 1 2.8 g of 3-(p-aminophenyl)-phosphonic acid diethyl ester (manufactured according to JACS, 81, 3026, )and 2.7 g of benzoylacetic acid methyl ester are warmed with 70 mg of sodium ethylate in 15 ml of absolute xylene isomer mixture to 125° C for 3½hours and the methyl alcohol formed is distilled off. After recrystallisation from ethyl acetate and acetone/ether, 0.9 g of pure coupling agent of the formula (101) of Table I is obtained in the form of a white powder of melting point 99 – 101 ° C.

The compounds of the formulae (102), (103), (113), (114), (115), (116), (117), (119),(124 ) and (125) of Table I are manufactured analogously.

EXAMPLE 2

10.4 g of 3-bromo-propane-phosphonic acid diethyl ester (manufactured in a known manner by heating 1,3- dibromopropane with triethyl phosphite and distilling off the ethyl bromide formed) and 15.2 g of N-methyl-3 nitroaniline in 50 ml of methyl ethyl ketone are warmed with 13 g of N-ethyl-diisopropylamine for 20 hours under reflux. After separating the reaction mixture on a chromatography column (silica gel; chloroform as the eluant, 9.9 g of pure 3-(N-methyl-N-3'-nitro-phenylamino) propane-phosphonic acid diethyl ester are obtained in the form of an orange-coloured oil.

9.9 g of this intermediate product, in 100 ml of ethanol, are hydrogenated with 0.5 g of palladium on active charcoal at room temperature and normal pressure in the usual manner, until the absorption of hydrogen has ceased.

After separating off the catalyst, distilling off the ethanol and treating the residue with 2 N sodium hydroxide solution and chloroform, 5.4 g of 3-(N-methyl-N-3'-amino-phenylamino) propane-phosphonic acid diethyl ester are obtained as a light brown oil.

The condensation with benzoylacetic acid methyl ester is carried out as indicated in Example 1.

The compound of the formula (104) is obtained in the form of a light brown resin, in a yield of 32%.

EXAMPLE 3

25.9 g of bromoacetic acid 3-nitrophenylamide and 37.5 g of tributyl phosphite in 150 ml of pure xylene isomer mixture are stirred under nitrogen for 30 minutes at 130° C. The residue obtained after distilling off the xylene and the excess tributyl phosphite at 1 mm Hg gives, after recrystallisation from chloroform/hexane, 29.5 g of pure 3-nitro-phenylcarbamoyl-methane-phosphonic acid dibutyl ester of melting point 80 – 81° C in the form of fine white needles.

Reduction of the nitro group according to Example 2 and condensation with pivaloylacetic acid ethyl ester analogously to Example 1 gives, in good yield, the coupling agent of the formula (105 ) in the form of a colourless, highly viscous oil.

The compounds of the formulae (106) and (109) are obtained analogously.

EXAMPLE 4

83 g of 3-nitrobenzoyl chloride in 150 ml of acetonitrile are added dropwise to a solution of 105 g of 2-aminopropane-2-phosphonic acid diethyl ester and 45 g of triethylamine in 300 ml of acetonitrile at 0° C, with good stirring. After completion of the addition, the mixture is stirred for a further 3 hours at 0° C; it is then filtered and the solvent is distilled off in vacuo. The residue is purified by extraction by shaking with ether and aqueous 2 normal sodium carbonate solution. 99 g of 2-(3'-nitrobenzamido)propane-2-phosphonic acid diethyl ester of melting point 95–96° C are obtained. This product is reduced with hydrogen as indicated in Example 2.

A solution of 5.6 g of 3-nitrobenzoyl chloride in 30 ml of acetonitrile is added dropwise to a mixture of 10.4 g of the amino compound obtained above and 3 g of triethylamine in 100 ml of acetonitrile at 0° C, with good stirring. Thereafter, the mixture is stirred for a further hour at 0° C and after distilling off the acetonitrile, the residue is dissolved in chloroform and purified by successive extraction by shaking with 2 N hydrochloric acid, water and 2 N ammonia. 11.5 g of 2[3'-(3''-nitrobenzamido) benzamido]propane -2 -phosphonic acid diethyl ester of melting point 120°– 121° C are obtained.

After reduction of the nitro group and subsequent condensation with benzoylacetic acid methyl ester according to Example 1, the coupling agent of the formula (107) is obtained in good yield as a yellowish powder of melting point 93°– 95° C. The compounds of the formulae (126 ), (136 ), (137) and (143 ) are manufactured analogously, employing the anilines from Example 1 in place of 2-(3'-aminobenzamido) propane-2phosphonic acid diethyl ester.

If 2-(3'-aminobenzamido)propane-2-phosphonic acid diethyl ester is condensed directly with benzoylacetic acid methyl ester, analogously to Example 1, the compound of the formula (108) is obtained in excellent yield, in the form of a white powder of melting point 158°– 160° C.

The compounds of the formulae (110), (111), (118), (127), (128), (131), (133), (134), (135), (139) and (140) are manufactured analogously.

EXAMPLE 5

1.34 g of 3-amino-benzoylacetic acid 2'-methoxy-5'-methyl-phenylamide, prepared by condensation of 3-nitro-benzoylacetic acid methyl ester with 2-methoxy-5-methylaniline and subsequent reduction of the nitro group, and 1.6 g of the acid chloride from Example 15, in 15 ml of N-methylpyrrolidone, are stirred for 3 hours at room temperature. After evaporation under 1 mm Hg and purification by column chromatography (silica gel), 1.5 g of the compound (112) are obtained in the form of a light yellow resin. The compounds (120) and (121) are prepared analogously.

EXAMPLE 6

3.4 g of the amino compound prepared according to Example 15, 2.1 g of benzoylacetic acid methyl ester and 0.1 ml of sym.-collidine in 30 ml of p-xylene are warmed for ½ hours to 140° C and the methanol formed is distilled off. After purification through a chromatography column, the compound of the formula (122 ) is obtained in the form of a light yellow resin.

The compound of the formula (123 ) is obtained analogously.

EXAMPLE 7

41.9 g of t-butane-phosphonic acid dichloride are dissolved in 300 ml of acetonitrile and a suspension of 33 g of sodium phenolate in 150 ml of acetonitrile is added at −15° C in such a way that the temperature does not exceed −12° C. After completion of the addition, the temperature is allowed to rise slowly to 20° C and after 3 hours a suspension of 46 g of sodium 4-nitrophenolate in 150 ml of acetonitrile is added and the mixture is warmed to 60° C for 2 hours. After distilling off the solvent, the residue is hydrogenated in isopropanol with palladium on charcoal as the catalyst (1 atmosphere). After purifying the crude product by extraction with ether and of the ether extract with hexane, 30 g of t-butanephosphonic acid 4-aminophenyl-(phenyl) ester of melting point 105° C are obtained. Condensation with benzoylacetic acid methyl ester in accordance with the method indicated in Example 6 gives the compound of the formula (129), of melting point 148° C, in excellent yield.

The compound of the formula (130) is prepared analogously.

EXAMPLE 8

31 g of diisoamyl phosphite are slowly added dropwise at 80° C to a suspension of 3.1 g of sodium in 150 ml of absolute toluene. After completion of the reaction, the suspension thus obtained is slowly added to a solution of 30 g of 3-phenyl-propyl bromide at 80° C, whilst stirring well. After 3 hours, the reaction mixture is centrifuged, the supernatant solution is evaporated and the residue is distilled under a vacuum of 0.2 mm Hg. At 158° C, 18 g of pure 3-phenylpropane-phosphonic acid diisoamyl ester pass over. After nitration and reduction (compare Example 1), 15.5 g of 3-(4'-aminophenyl)-propane-phosphonic acid diisoamyl ester are obtained.

The condensation with 4-chloro-benzoylacetic acid methyl ester in accordance with the method indicated in Example 6 gives the coupling agent of the formula (132), of melting point 116° C, in good yield.

EXAMPLE 9

20 g of n-butanephosphonic acid n-butyl ester chloride are added dropwise to a suspension of 14.3 g of sodium 3-nitrophenolate in 170 ml toluene at 20° C. After 4 hours, the mixture is filtered, the filtrate is evaporated and the residue is distilled in vacuo at 0.1 mm Hg. 16 g of n-butanephosphonic acid n-butyl-(3-nitrophenyl) ester are obtained. After reduction with hydrogen and palladium on charcoal, in isopropanol, at 1 atmosphere pressure, 13.8 g of n-butanephosphonic acid n-butyl-(3-aminophenyl) ester are obtained.

A solution of 16 g of 4-nitrophenylacetyl chloride in 30 ml of benzene is added dropwise to a solution of 11.5 g of n-butanephosphonic acid n-butyl-(3-aminophenyl) ester and 6 g of triethylamine in 50 ml of benzene at 20° C. After 40 hours, the mixture is filtered and the filtrate is purified by extraction by shaking with potassium bicarbonate solution and hydrochloric acid. 9.3 g of n-butanephosphonic acid n-butyl-[3-(4'-nitrophenyl-acetamido)phenyl] ester are obtained. This is reduced as indicated in Example 7. After the condensation with 2-chlorobenzoylacetic acid ethyl ester in accordance with the method indicated in Example 6, a crude product is obtained, from which the pure product of the formula (138) is obtained by purification by column chromatography.

EXAMPLE 10

29 g of n-butanephosphonic acid n-butyl ester chloride are added dropwise to a solution of 20 go of 3-nitroaniline and 14.1 g of triethylamine in 300 ml of acetonitrile at 0° C. After 20 hours the mixture is evaporated, the residue is suspended in 300 ml of ether, the mixture is acidified with hydrochloric acid in ether and filtered, and the filtrate is evaporated. 33 g of n-butanephosphonic acid n-butyl ester 3-nitroanilide are obtained in the form of a yellow oil.

After reduction with hydrogen and acylation with 2-chloro-5-nitro-benzoyl chloride in chloroform/triethylamine, and purification by column chromatography, 7 g of n-butane-phosphonic acid n-butyl ester-3-(2'-chloro-5'nitro-benzamido)-anilide are obtained. 4.7 g of this compound are dissolved in 50 ml of glacial acetic acid at 20° C. 1.25 g of iron powder, 0.2 ml of water and a little iron-(II) sulphate are added thereto. The reaction mixture is warmed to 55° C whilst stirring well and is kept at this temperature for 3 hours. After evaporation in vacuao, the vacuo, is partitioned between 80 ml of 1 normal sodium carbonate solution and 300 ml of chloroform. The chloroform phase on evaporation gives 5.5 g of n-butanephosphonic acid n-butyl ester-3-(2'chloro-5'-amino-benzamido)-anilide. After condensation with benzoylacetic acid methyl ester in accordance with Example 6 and purification of the crude product by column chromatography, the compound of the formula (141) is obtained in the form of a dark yellow resin.

EXAMPLE 11

A solution of 15 g of 4-nitro-benzoyl chloride in 100 ml of acetonitrile is added dropwise to a solution of 20 g of α-hydroxy-propanephosphonic acid dibutyl ester and 8 g of pyridine in 20 ml of acetonitrile at 0° C. After 16 hours the mixture is filtered, the filtrate is evaporated and the residue is extracted with 200 ml of diethyl ether. After evaporation, and purification by column chromatography, 13 g of pure α-(4-nitro-benzoyloxy)-propanephosphonic acid dibutyl ester are obtained. This is reduced with hydrogen as indicated in Example 2. 12.5 g of α-(4-amino-benzoyl-oxy)-propanephosphonic acid dibutyl ester are obtained. After condensation with o-methoxybenzoylacetic acid methyl ester according to Example 6, and purification by column chromatography, the compound of the formula (142) is obtained in the form of a yellow resin.

EXAMPLE 12

A solution of 10.3 g of 4-chloro-3-nitro-benzoyl chloride in 40 ml of acetonitrile is added dropwise to a solution of 15 g of 5-amino-1,3,3-trimethyl-cyclo-hexanephosphonic acid diisopropyl ester and 5 g of triethylamine in 250 ml of acetonitrile at −5° C. After 2 hours, the temperature is allowed to rise to 20° C and the mixture is stirred for a further 17 hours at this temperature. It is then stirred for a further 4 hours, at 50° C. After evaporation, the residue is partitioned between 300 ml of chloroform and 50 ml of water and the chloroform phase is successively extracted by shaking with 2 N hydrochloric acid and 2 N sodium carbonate solution. After distilling off the chloroform and recrystallising from ethyl acetate, 14.1 g of 5-(3'-chloro-4'-nitro-benzamido)-1,3,3-trimethylcyclohexanephosphonic acid diisopropyl ester of melting point 174° C are obtained.

11.2 g of this product, in a solution of 1.5 g of sodium and 3.3 g of phenol in 200 ml of isopropanol, are allowed to react for 40 hours at 50° C. After distilling off the isopropanol, the residue is dissolved in chloroform and the chloroform phase is washed with water until neutral. After distilling off the chloroform, 11.7 g of 5-(3'-phenoxy-4'-nitro-benzamido) -1,3,3-trimethyl-cyclohexane-phosphonic acid diisopropyl ester are obtained in the form of a reddish-yellow oil.

This is reduced in isopropanol by means of hydrogen, as indicated in Example 2. 7.7 g of 5-(3'-phenoxy-4'-amino-benzamido) -1,3,3-trimethyl-cyclohexane-phosphonic acid diisopropyl ester are obtained in the form of a dark brown oil.

After condensation with 4-chlorobenzylacetic acid methyl ester in accordance with Example 6 and purification by column chromatography, the compound of the formula (144) is obtained in the form of a light yellow resin.

EXAMPLE 13

A solution of 5.5 g of 3-nitro-benzoyl chloride in 25 ml of acetonitrile is added dropwise to a solution of 11.4 g of 4-amino-benzenephosphonic acid di-n-hexyl ester and 3.7 g of triethylamine in 100 ml of acetonitrile at 0° C. After one and a half hours, the mixture is allowed to warm up to 20° C and is stirred for a further hour at this temperature.

After distilling off the acetonitrile, the residue is extracted with 200 ml of benzene, the benzene phase is successively washed with 50 ml of 2 N sodium carbonate solution, 50 ml of 2 N hydrochloric acid and 50 ml of water and the benzene is distilled off apart from a small residue. After completion of crystallisation, the product is filtered off and recrystallised from diethyl ether. 6.1 g of 4-(3'-nitrobenzamido)-benzenephosphonic acid di-n-hexyl ester of melting point 98° C are obtained. After reduction with hydrogen and condensation with 4-chlorobenzoylacetic acid methyl ester in accordance with the method indicated in Example 6, the coupling agent of the formula (145) is obtained in good yield.

EXAMPLE 14

0.3 g of sulphuryl chloride is added dropwise at 20° C to a solution of 0.8 g of the compound of the formula (130) and 0.14 g of anhydrous sodium acetate in 8 ml of glacial acetic acid. After 50 minutes, the mixture is poured into 70 ml of ice water and the product is filtered off and recrystallised from ethyl acetate. 0.4 g of the compound (146), of melting point 128° C, is obtained.

The compound of the formula (117) is prepared analogously.

The compounds of the formulae which follow are prepared according to methods which are in themselves known, from the corresponding 4-equivalent coupling agents (the corresponding compounds with hydrogen in the position marked with an *, in place of the substituents drawn). With regard to methods of manufacture, compare DT-OS or DT-AS 1,236,332, 2,043,271, 1,547,672 or 1,187,477. Next to the formula, the absorption maximum in nm is specified in each case (see footnote to Table I).

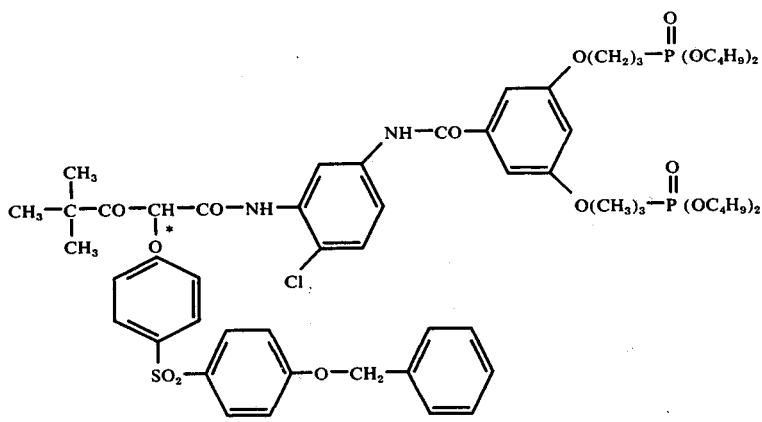

444

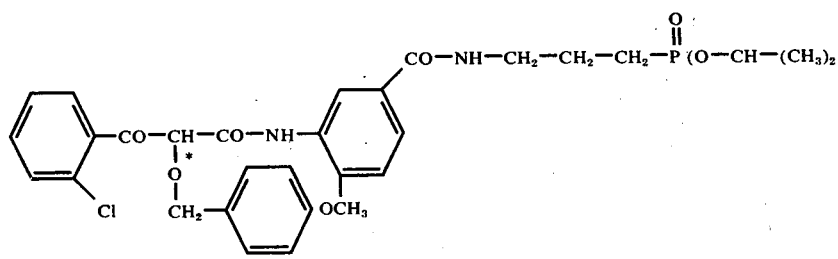

447

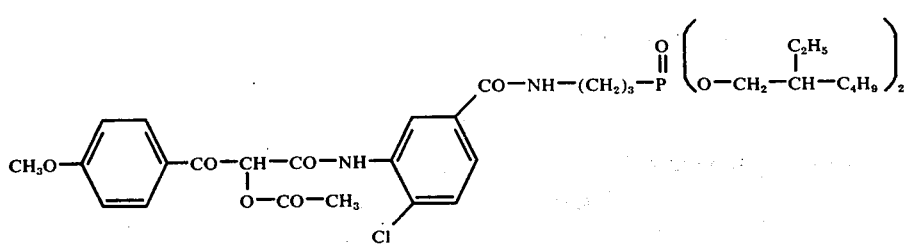

447

-continued
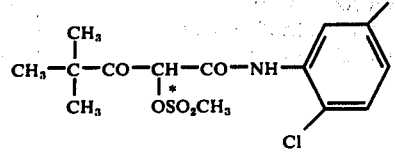
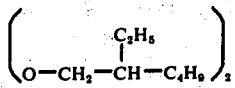
445
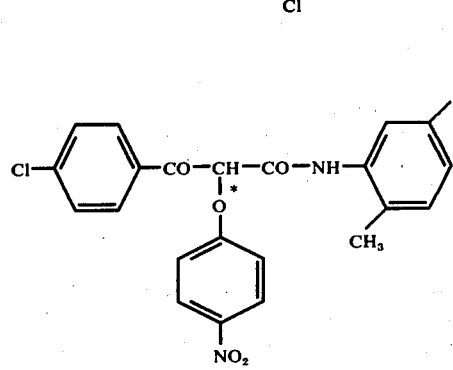
441
444
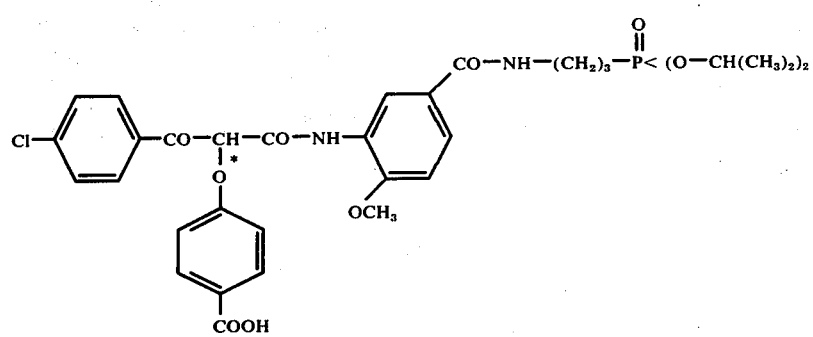
436
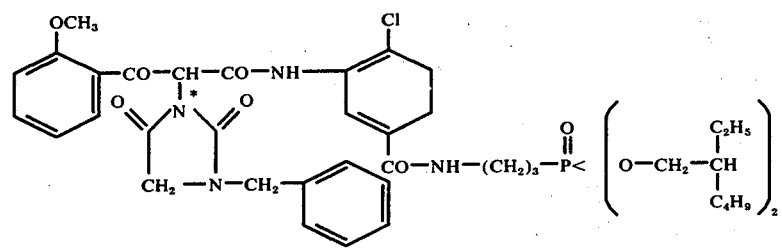
TABLE I
| For-mula No. | Structure | Abs. max. * in [nm] |
|---|---|---|
| (101) | ⌬—CO—CH$_2$—CO—NH—⌬—(CH$_2$)$_3$—P(=O)< (—O—C$_2$H$_5$)$_2$ | 437 |
| (102) | ⌬—CO—CH$_2$—CO—NH—⌬—CH$_2$—P(=O)< (—O—C$_2$H$_5$)$_2$ | 438 |
| (103) | (CH$_3$)$_3$C—CO—CH$_2$—CO—NH—⌬—(CH$_2$)$_3$—P(=O)< (—O—C$_2$H$_5$)$_2$ | 429 |

TABLE I-continued

| Formula No. | Structure | Abs. max. * in [nm] |
|---|---|---|
| (104) | C₆H₅—CO—CH₂—CO—NH—C₆H₄—N(CH₃)—(CH₂)₃—P(=O)(—O—C₂H₅)₂ | 435 |
| (105) | (CH₃)₃C—CO—CH₂—CO—NH—C₆H₄—NH—CO—CH₂—P(=O)(—O—CH₂CH₂CH₂CH₃)₂ | 436 |
| (106) | C₆H₅—CO—CH₂—CO—NH—C₆H₄—NH—CO—CH₂—P(=O)(—O—C₂H₅)₂ | 442 |
| (107) | C₆H₅—CO—CH₂—CO—NH—C₆H₄—CO—NH—C₆H₄—CO—NH—C(CH₃)₂—P(=O)(—O—C₂H₅)₂ | 444 |
| (108) | C₆H₅—CO—CH₂—CO—NH—C₆H₄—CO—NH—C(CH₃)₂—P(=O)(—O—C₂H₅)₂ | 440 |
| (109) | C₆H₅COCH₂CONH—C₆H₄—NHCOCH₂P(=O)(—O—CH₂—CH₂—CH₂—CH₃)₂ | 442 |
| (110) | O₂N—C₆H₄—COCH₂CONH—C₆H₄—CONH—C(CH₃)₂—P(=O)(—O—C₂H₅)₂ | 440 |
| (111) | C₆H₅—COCH₂CONH—C₆H₃—[—CONHC(CH₃)₂—P(=O)(O—C₂H₅)₂]₂ | 440 |
| (112) | (H₅C₂—O)₂>P(=O)—(CH₂)₃—O—C₆H₄—CONH—C₆H₄—COCH₂CONH—C₆H₃(CH₃)(OCH₃) | 440 |

TABLE I-continued

| Formula No. | Structure | Abs. max.* in [nm] |
|---|---|---|
| (113) | C₆H₅—COCH₂CONH—(2,5-dimethylphenyl)—[—CH₂—P(=O)(—O—CH₂—CH₂—CH₂—CH₃)₂]₂ | 434 |
| (114) | (CH₃)₃C—CO—CH₂—CO—NH—C₆H₄—NH—OC—(3,5-disubstituted phenyl with two O—(CH₂)₃—P(=O)(—O—CH₂—CH₂—CH₂—CH₃)₂ groups) | 431 |
| (115) | (CH₃)₃C—CO—CH₂—CO—NH—C₆H₄(meta)—NH—OC—(3,5-disubstituted phenyl with two O—(CH₂)₃—P(=O)(—O—CH₂—CH₂—CH₂—CH₃)₂ groups) | 435 |
| (116) | (CH₃)₃C—CO—CH₂—CO—NH—(2-Cl-phenyl)—NH—OC—(3,5-disubstituted phenyl with two O—(CH₂)₃—P(=O)(—O—CH₂—CH₂—CH₂—CH₃)₂ groups) | 444 |
| (117) | (CH₃)₃C—CO—CH₂—CO—NH—(2-CH₃-phenyl)—NH—OC—(3,5-disubstituted phenyl with two O—(CH₂)₃—P(=O)(—O—CH₂—CH₂—CH₂—CH₃)₂ groups) | 445 |

TABLE I-continued

| Formula No. | Structure | Abs. max.* in [nm] |
|---|---|---|
| (118) | (structure) | 438 |
| (119) | (structure) | 436 |
| (120) | (structure) | 434 |
| (121) | (structure) | 434 |
| (122) | (structure) | 436 |

TABLE I-continued

| Formula No. | Structure | Abs. max. * in [nm] |
|---|---|---|
| (123) | C₆H₅—CO—CH₂—CO—NH—C₆H₄—O—CH₂—CH₂—CH₂—P(=O)(O—CH₂CH₂CH₂CH₃)₂ | 436 |
| (124) | C₆H₅—CO—CH₂—CO—NH—C₆H₄—CH₂—CH₂—CH₂—P(=O)(O—CH₂CH₂CH₂CH₃)₂ | 436 |
| (125) | 4-Cl—C₆H₄—CO—CH₂—CO—NH—C₆H₄—CH₂—CH₂—CH₂—P(=O)(O—CH₂CH₂CH₂CH₃)₂ | 436 |
| (126) | 4-CH₃O—C₆H₄—CO—CH₂—CO—NH—(4-OCH₃, 3-substituted phenyl)—CO—NH—C₆H₄—CH₂CH₂CH₂—P(=O)(O—CH₂CH₂CH₂CH₃)₂ | 448 |
| (127) | 4-Cl—C₆H₄—CO—CH₂—CO—NH—(2-OCH₃, 5-substituted phenyl)—CO—NH—CH₂CH₂CH₂—P(=O)(O—CH(CH₃)₂)₂ | 444 |
| (128) | 2-Cl—C₆H₄—CO—CH₂—CO—NH—(4-OCH₃, 3-substituted phenyl)—CO—NH—CH₂CH₂CH₂—P(=O)(O—CH(CH₃)₂)₂ | 447 |
| (129) | C₆H₅—CO—CH₂—CO—NH—C₆H₄—O—P(=O)(O—C₆H₅)(C(CH₃)₃) | 440 |
| (130) | 4-CH₃O—C₆H₄—CO—CH₂—CO—NH—C₆H₄—O—P(=O)(O—C₆H₅)(C(CH₂)₃) | 437 |

TABLE I-continued
| Formula No. | Structure | Abs. max. * in [nm] |
|---|---|---|
| (131) | 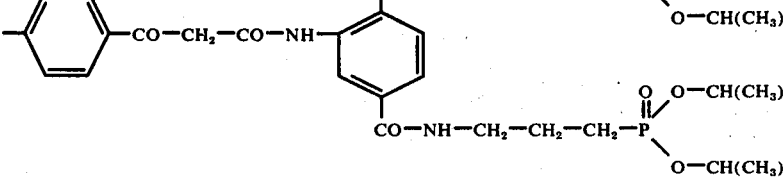 | 442 |
| (132) | 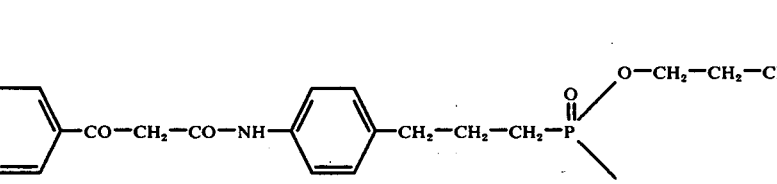 | 438 |
| (133) | 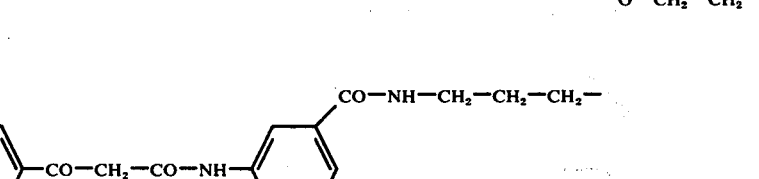 | 436 |
| (134) | 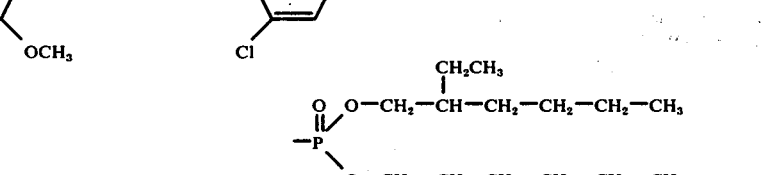 | 447 |
| (135) | 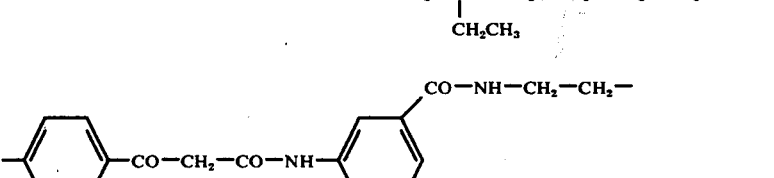 | 445 |

TABLE I-continued

| Formula No. | Structure | Abs. max. * in [nm] |
|---|---|---|
| (136) | 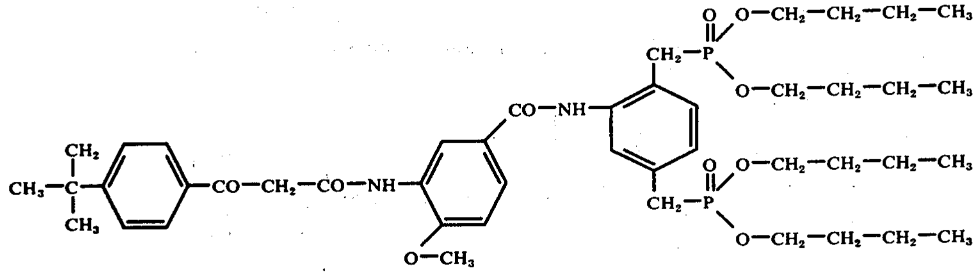 | 440 |
| (137) | 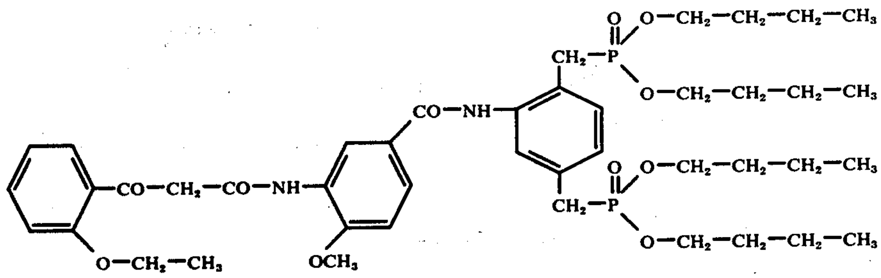 | 425 |
| (138) | 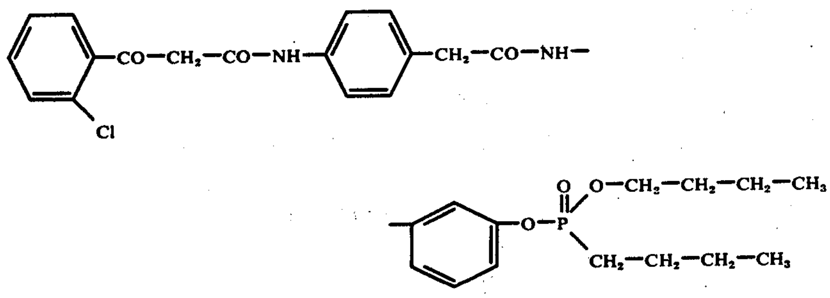 | 442 |
| (139) | 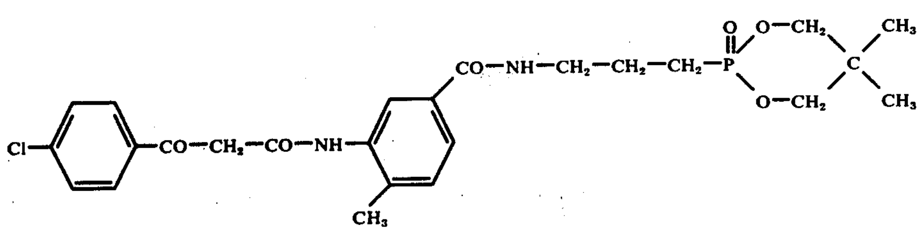 | 441 |
| (140) | 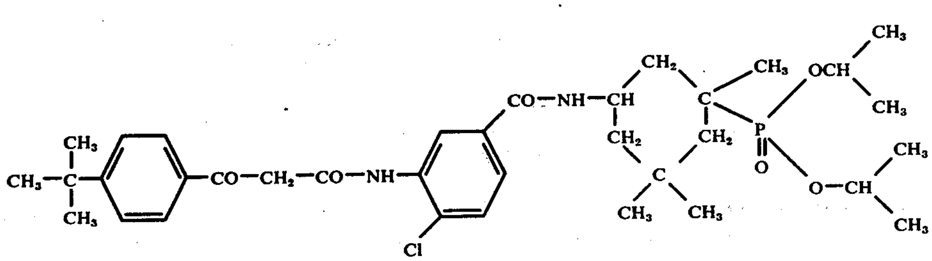 | 439 |
| (141) | 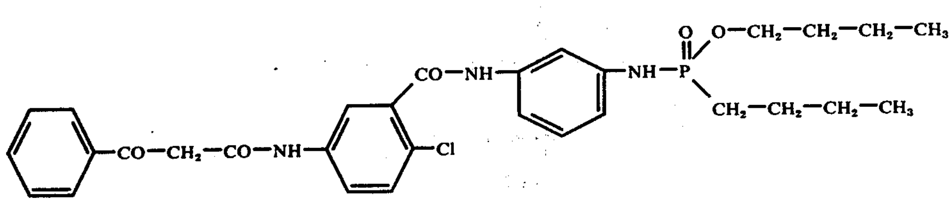 | 438 |

TABLE I-continued

| Formula No. | Structure | Abs. max.* in [nm] |
|---|---|---|
| (142) | [structure with 2-methoxyphenyl-CO-CH₂-CO-NH-phenyl-CO-O-CH(CH₂CH₃)-P(=O)(O-CH₂-CH₂-CH₂-CH₃)₂] | 435 |
| (143) | [structure with 2-chlorophenyl-CO-CH₂-CO-NH-(methylphenyl)-CO-NH-phenyl with two CH₂-P(=O)(O-CH₂-CH₂-CH₂-CH₃)₂ groups] | 440 |
| (144) | [structure with 4-chlorophenyl-CO-CH₂-CO-NH-(phenoxyphenyl)-CO-NH-CH(CH₂-C(CH₃)₂-CH₂)C-P(=O)(O-CH(CH₃)₂)₂] | 441 |
| (145) | [structure with 4-chlorophenyl-CO-CH₂-CO-NH-phenyl-CO-NH-phenyl-P(=O)(O-CH₂-CH₂-CH₂-CH₂-CH₂-CH₃)₂] | 449 |
| (146) | CH₃O-phenyl-CO-CH(Cl)-CO-NH-phenyl-O-P(=O)(O-phenyl)(C(CH₃)₃) | 437 |
| (147) | phenyl-CO-CH(Cl)-CO-NH-phenyl-CH₂-CH₂-CH₂-P(=O)(O-CH₂-CH₂-CH₂-CH₃)₂ | 436 |

*After colour developement of the coupling agents in a photographic silver halide layer according to Use Example I

EXAMPLE 15

1.5 g of m-hydroxybenzoic acid methyl ester, 2.6 g of 3-bromopropane-phosphonic acid diethyl ester prepared in the usual manner from 1,3-dibromopropane and triethyl phosphite and 0.7 g of anhydrous potassium carbonate in 20 ml of ethyl methyl ketone are heated to the boil under reflux for 36 hours. The potassium bromide which has separated out is filtered off and the filtrate is evaporated to dryness, whereupon 2.9 g of ester of the formula

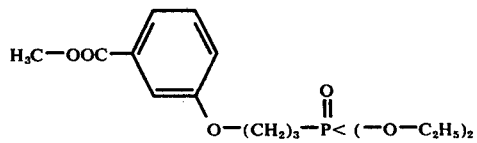

are obtained in the form of a yellowish oil.

Saponification of 30 g of this ester in ethanolic sodium hydroxide solution at 55° C gives 25 g of acid of the formula

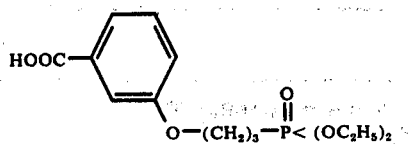

in the form of a yellowish oil.

5 g of the carboxylic acid thus obtained, on reaction with thionyl chloride in the usual manner, give 5 g of the acid chloride of the formula

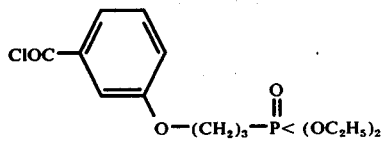

as a yellowish oil.

0.4 g of 1(2',4',6'trichlorophenyl)-3(4''aminobenzamido) 5-pyrazolone obtained in a known manner is dissolved in 5 ml of N-methyl-5-pyrrolidone and this solution is added to 0.4 g of acid chloride of the above formula. The reaction mixture is stirred for 1 hour at room temperature and poured into a mixture of 25 ml of water and 1.2 ml of 30% strength sodium hydroxide solution, the whole is stirred for 15 minutes and filtered, and 40 ml of water and 5 ml of 36% strength hydrochloric acid are added to the filtrate.

The product which has precipitated is filtered off, washed with water until neutral and dried, and 0.6 g of coupling agent of the formula (201) is obtained in the form of a light beige powder of melting point 120° C.

The remaining compounds of Table II are prepared analogously.

TABLE II
| Formula No. | $R_{11}$ | $R_{12}$ | Abs. max in [nm]* (see footnote, Table I) |
|---|---|---|---|
| (201) | 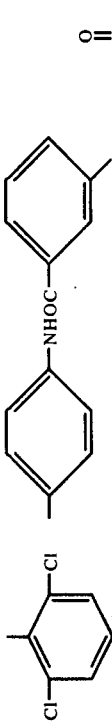 |  | 432 + 542 |
| (202) | 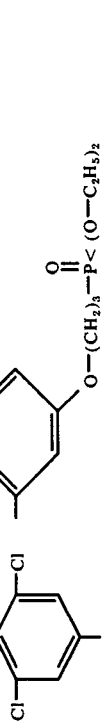 |  | 434 + 535 |
| (203) |  | 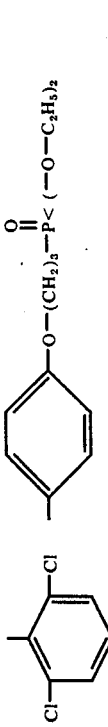 | 434 + 539 |
| (204) |  | | 434 + 534 |

TABLE II-continued
| Formula No. | $R_{11}$ | $R_{12}$ | Abs. max in [nm]*) (see footnote, Table I) |
|---|---|---|---|
| (205) | 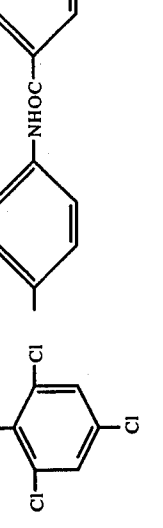 | 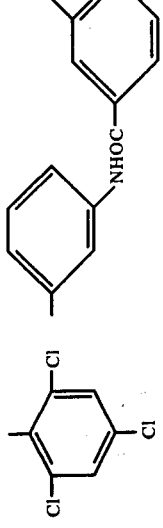 | 434 + 542 |
| (206) |  | 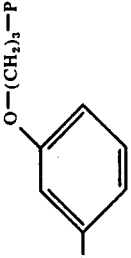 | 434 + 542 |
| (207) | 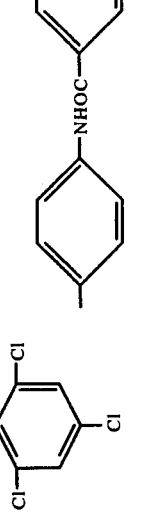 | 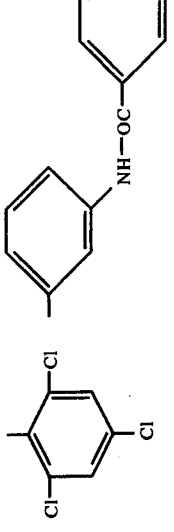 | 434 + 540 |
| (208) |  |  | 434 + 546 |

TABLE II-continued

| Formula No. | $R_{11}$ | $R_{12}$ | Abs. max in [nm]*) (see footnote, Table I) |
|---|---|---|---|
| (209) | 2,5-dichlorophenyl | $-\text{O}-(CH_2)_3-\overset{O}{\underset{\|}{P}}<(-O-C_2H_5)_2$ on 3,5-disubstituted phenyl with NHOC-phenyl | 436 + 540 |
| (210) | 2,5-dichlorophenyl | phenyl-NHOC-phenyl-O-$(CH_2)_3$-P(=O)(-OCH(CH_3)_2)_2 | 434 + 543 |
| (211) | 2,5-dichlorophenyl | phenyl-NHOC-phenyl-O-$(CH_2)_3$-P(=O)(-O-CH_2-CH_2-CH_2-CH_3)_2 | 434 + 543 |
| (212) | 2,5-dichlorophenyl | 3,5-bis[O-$(CH_2)_3$-P(=O)(-O-C_2H_5)_2] with NHOC-phenyl | 434 + 544 |

TABLE II-continued

R₁₂ structure (shown at top): pyrazolone ring with R₁₁–N, C=O, H₃C, N=C–HN–CO–R₁₂

| Formula No. | R₁₁ | R₁₂ | Abs. max in [nm]* (see footnote, Table I) |
|---|---|---|---|
| (213) | 2,4,5-trichlorophenyl | 3-methylphenyl–O–(CH₂)₅–P(=O)(–O–C₂H₅)₂ | 434 + 537 |
| (214) | 2,4,5-trichlorophenyl | 3,5-disubstituted phenyl (CH₃ and O–(CH₂)₅–P(=O)(–O–C₂H₅)₂) | 432 + 540 |
| (215) | 2,4,5-trichlorophenyl | 4-methylphenyl–NHOC–phenyl–O–(CH₂)₃–P(=O){–O–CH₂–CH(C₂H₅)–CH₂–CH₂–CH₂–CH₃}₂ | 434 + 540 |
| (216) | 2,4,5-trichlorophenyl | 3-methylphenyl–NH–OC–phenyl(3,5-di)–[O–(CH₂)₃–P(=O)(–O–C₂H₅)₂]₂ | 432 + 546 |

TABLE II-continued

| Formula No. | R₁₁ | R₁₂ | Abs. max in [nm]* (see footnote, Table I) |
|---|---|---|---|
| (217) | 2,4,5-trichlorophenyl | phenyl-O-(CH₂)₃-P(=O)(-O-CH(CH₃)₂)₂ (meta-substituted) | 435 + 538 |
| (218) | 2,4,5-trichlorophenyl | 4-methylphenyl-NH-CO-(3,5-di{O-(CH₂)₃-P(=O)(-O-CH₂-CH₂-CH₂-CH₃)₂}phenyl) | 436 + 542 |
| (219) | 2,4,5-trichlorophenyl | 3-methylphenyl-NH-CO-phenyl-O-(CH₂)₃-P(=O)(-O-CH₂-CH(C₂H₅)-CH₂-CH₂-CH₂-CH₃)₂ | 436 + 542 |
| (220) | 2,4,5-trichlorophenyl | 3-methylphenyl-NH-CO-phenyl-O-(CH₂)₃-P(=O)(-O-CH₂-CH₂-CH₂-CH₃)₂ | 434 + 544 |

TABLE II-continued

| Formula No. | $R_{11}$ | $R_{12}$ | Abs. max in [nm1*] (see footnote, Table 1) |
|---|---|---|---|
| (221) | 2,5-dichlorophenyl | 3,5-bis[O—(CH$_2$)$_3$—P(=O)(—O—CH$_2$—CH$_2$—CH$_2$—CH$_3$)$_2$]phenyl | 436 + 538 |
| (222) | 2,5-dichlorophenyl | 3,5-bis[NH—CO—...—O—(CH$_2$)$_3$—P(=O)(—O—CH$_2$—CH$_2$—CH$_2$—CH$_3$)$_2$]phenyl | 434 + 544 |
| (223) | phenyl | 3-[NH—CO-...-O—(CH$_2$)$_3$—P(=O)(—O—CH$_2$—CH$_2$—CH$_3$)$_2$]phenyl | 440 + 534 |
| (224) | phenyl | 3-[NH—CO-...-O—(CH$_2$)$_3$—P(=O)(—O—CH$_2$—CH$_2$—CH$_2$—CH$_3$)$_2$]phenyl | 440 + 534 |

TABLE II-continued

| Formula No. | R₁₁ | R₁₂ | Abs. max in [nm]* (see footnote, Table I) |
|---|---|---|---|
| (225) | phenyl | 3-(NH-CO-tolyl)phenyl-O-(CH₂)₅-P(=O){-O-CH₂-CH(C₂H₅)-CH₂-CH₂-CH₂-CH₃}₂ | 440 + 532 |
| (226) | phenyl | 3,5-(NH-CO-tolyl)phenyl-O-(CH₂)₅-P(=O)(-O-CH₂-CH₃)₂ | 439 + 534 |
| (227) | phenyl | 3-(NH-CO-tolyl)phenyl-O-(CH₂)₅-P(=O)(-O-CH₂-CH₃)₂ | 438 + 532 |
| (228) | phenyl | 3,5-(NH-CO-tolyl)phenyl-O-(CH₂)₅-P(=O)(-O-CH₂-CH₃)₂ | 438 + 533 |

TABLE II-continued

Structure:

$R_{11}$ attached to N of a ring: O=C–N(R₁₁)–N=C(–NH–CO–R₁₂)–CH₂ (pyrazolone ring)

| Formula No. | $R_{11}$ | $R_{12}$ | Abs. max in [nm]* (see footnote, Table I) |
|---|---|---|---|
| (229) | phenyl | 3-(CH₃)-C₆H₃(NH-CO-)-O-(CH₂)₃-P(=O)(-O-CH₂-CH₂-CH₂-CH₃)₂ (meta-substituted; the NHCO-aryl group bears an O-(CH₂)₃-P(=O)(-O-CH₂-CH₂-CH₂-CH₃)₂ at 3- and 5- positions on a central phenyl, linked via NH to a tolyl) | 440 + 532 |
| (230) | 2,4,6-trichloro-phenyl (with CH₃) | tolyl-NH-CO- phenyl-O-(CH₂)₅-P(=O)(-O-CH₂-CH₃)₂ | 434 + 544 |
| (231) | 2,4,6-trichloro-phenyl (with CH₃) | 3,5-bis[O-(CH₂)₅-P(=O)(-O-CH₂-CH₃)₂]-phenyl-NHCO- linked to tolyl | 434 + 545 |

TABLE II-continued
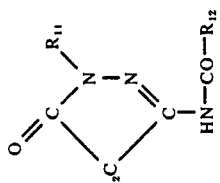
| Formula No. | $R_{11}$ | $R_{12}$ | Abs. max in [nm]*) (see footnote, Table I) |
|---|---|---|---|
| (232) | 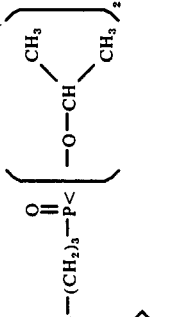 | 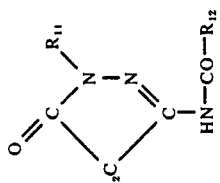 | 434 + 541 |
| (233) | | 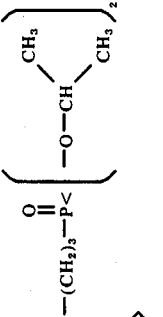 | 441 + 530 |
| (234) | | 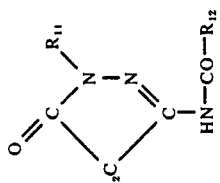 | 434 + 540 |

TABLE II-continued

| Formula No. | R₁₁ | R₁₂ | Abs. max in [nm]* (see footnote, Table I) |
|---|---|---|---|
| (235) | phenyl | 3-(phenyl-NHCO-)phenyl-O-(CH₂)₃-P(=O)(-O-CH₂-CH(C₂H₅)-CH₂-CH₂-CH₂-CH₃)₂ | 440 + 532 |
| (236) | 2,5-dichlorophenyl | 3-(phenyl-NHCO-)phenyl-O-(CH₂)₃-P(=O)(-O-CH₂-CH(C₂H₅)-CH₂-CH₂-CH₂-CH₃)₂ | 436 + 541 |
| (237) | 2,5-dichlorophenyl | 3-methylphenyl-O-(CH₂)₃-P(=O)(-O-CH₂-CH₂-CH₂-CH₃)₂ | 432 + 536 |

TABLE II-continued
| Formula No. | $R_{11}$ | $R_{12}$ | Abs. max in [nm]* (see footnote, Table I) |
|---|---|---|---|
| (238) | 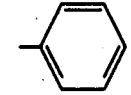 | 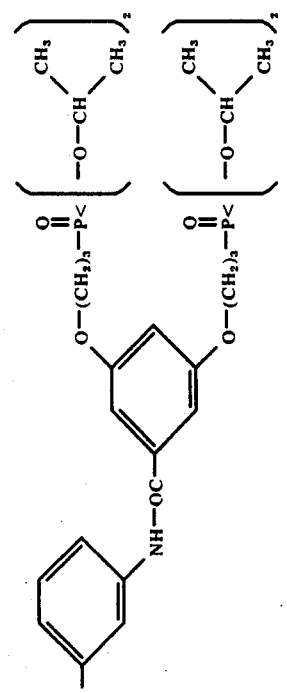 | 440 + 530 |
| (239) | 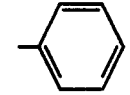 | 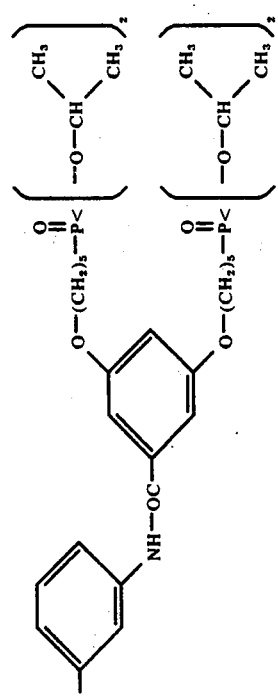 | 440 + 532 |

TABLE II-continued
| Formula No. | R₁₁ | R₁₂ | Abs. max in [nm]*) (see footnote, Table I) |
|---|---|---|---|
| (240) | 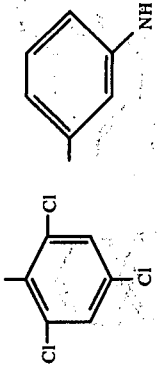 | 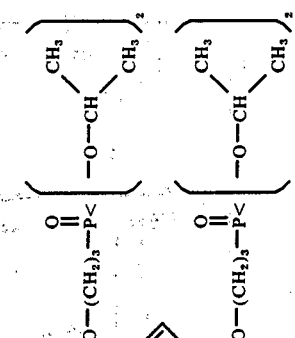 | 434 + 544 |
| (241) | 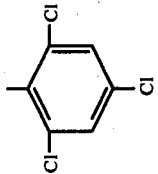 | 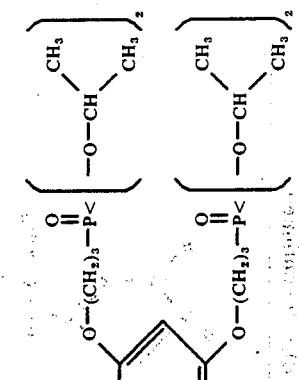 | 434 + 541 |

TABLE II-continued
| Formula No. | $R_{11}$ | $R_{12}$ | Abs. max in [nm]*) (see footnote, Table I) |
|---|---|---|---|
| (242) | 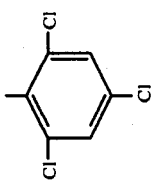 | 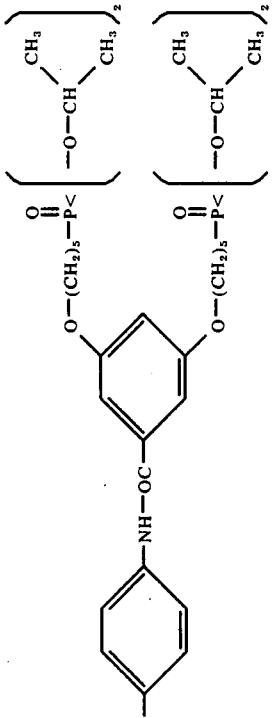 | 436 + 542 |
| (243) | 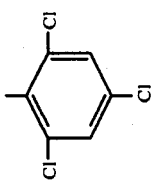 | 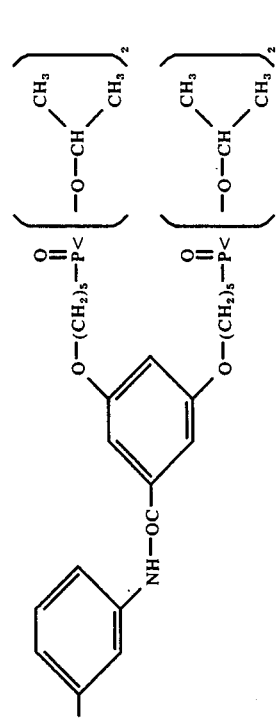 | 434 + 544 |
| (244) | 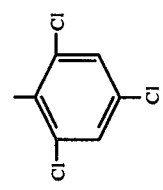 | 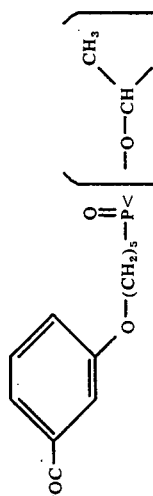 | 434 + 542 |

TABLE II-continued
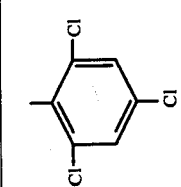
| Formula No. | $R_{11}$ | $R_{12}$ | Abs. max in [nm]*) (see footnote, Table I) |
|---|---|---|---|
| (245) | 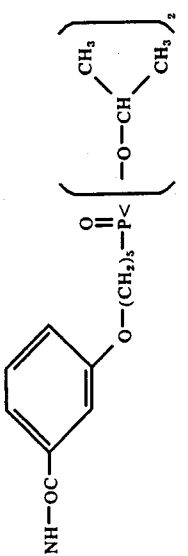 | 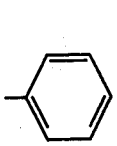 | 434 + 542 |
| (246) | 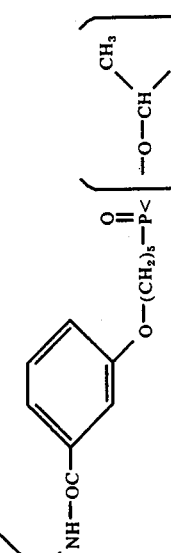 | 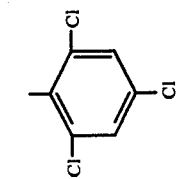 | 440 + 532 |
| (247) | 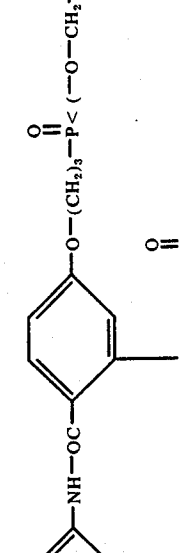 | | 436 + 540 |

TABLE II-continued

| Formula No. | $R_{11}$ | $R_{12}$ | Abs. max in [nm]* (see footnote, Table I) |
|---|---|---|---|
| (248) | 2,5-dichlorophenyl | 3-methylphenyl-NH-CO- attached to benzene ring with -O-(CH$_2$)$_3$-P(=O)(-O-CH$_2$-CH$_2$-CH$_2$-CH$_3$)$_2$ and -O-(CH$_2$)$_3$-P(=O)(-O-CH$_2$-CH$_2$-CH$_2$-CH$_3$)$_2$ | 436 + 541 |
| (249) | phenyl | 3-methylphenyl-NH-CO- attached to benzene ring with -O-(CH$_2$)$_3$-P(=O)(-O-CH$_2$-CH$_2$-CH$_2$-CH$_3$)$_2$ and -O-(CH$_2$)$_3$-P(=O)(-O-CH$_2$-CH$_2$-CH$_2$-CH$_3$)$_2$ | 442 + 532 |
| (250) | 2,5-dichlorophenyl | 4-methylphenyl-NH-CO- attached to benzene ring with -O-(CH$_2$)$_3$-P(=O){-O-CH$_2$-CH(C$_2$H$_5$)-CH$_2$-CH$_2$-CH$_2$-CH$_3$}$_2$ and -O-(CH$_2$)$_3$-P(=O){-O-CH$_2$-CH(C$_2$H$_5$)-CH$_2$-CH$_2$-CH$_2$-CH$_3$}$_2$ | 434 + 537 |

TABLE II-continued

| Formula No. | R₁₁ | R₁₂ | Abs. max in [nm]* (see footnote, Table I) |
|---|---|---|---|
| (251) | 2,5-dichlorophenyl | 4-[NH-CO-phenyl], 2-O-(CH₂)₃-P(=O)(-O-CH₂-CH(C₂H₅)-CH₂-CH₂-CH₂-CH₃)₂, with second -O-(CH₂)₃-P(=O)(-O-CH₂-CH(C₂H₅)-CH₂-CH₂-CH₂-CH₃)₂ group | 436 + 540 |
| (252) | phenyl | 4-[NH-CO-phenyl], 2-O-(CH₂)₃-P(=O)(-O-CH₂-CH(C₂H₅)-CH₂-CH₂-CH₂-CH₃)₂, with second -O-(CH₂)₃-P(=O)(-O-CH₂-CH(C₂H₅)-CH₂-CH₂-CH₂-CH₃)₂ group | 440 + 532 |
| (253) | 4-cyanophenyl | 3,5-bis[O-(CH₂)₃-P(=O)(-O-CH₂-CH₂-CH₂-CH₃)₂]phenyl | 440 + 540 |

TABLE II-continued

| Formula No. | $R_{11}$ | $R_{12}$ | Abs. max in [nm]* (see footnote, Table I) |
|---|---|---|---|
| (254) | 2,4,5,6-tetrachloro-3-methyl-methoxyphenyl | 3,5-bis[O—(CH$_2$)$_3$—P(=O)(—O—CH$_2$—CH$_2$—CH$_2$—CH$_3$)$_2$]phenyl | 438 + 540 |
| (255) | 3-chlorophenyl | 3-[NH—OC—phenyl—O—(CH$_2$)$_3$—P(=O)(—O—CH$_2$—CH$_2$—CH$_2$—CH$_3$)$_2$] (bis substituted) | 438 + 536 |
| (256) | 3-chlorophenyl | 3-[NH—OC—phenyl—O—(CH$_2$)$_3$—P(=O){—O—CH$_2$—CH(C$_2$H$_5$)—CH$_2$—CH$_2$—CH$_2$—CH$_3$}$_2$] | 438 + 534 |

TABLE II-continued

| Formula No. | $R_{11}$ | $R_{12}$ | Abs. max in [nm]* (see footnote, Table I) |
|---|---|---|---|
| (257) | benzothiazol-2-yl | 3,5-bis[O—(CH$_2$)$_3$—P(=O)(—O—CH$_2$—CH$_2$—CH$_2$—CH$_3$)$_2$]phenyl-NH-CO- | 430 + 537 |
| (258) | benzothiazol-2-yl | 3,5-bis[O—(CH$_2$)$_3$—P(=O)(—O—CH$_2$—CH$_2$—CH$_2$—CH$_3$)$_2$]-anilide (m-tolyl-NH-CO-) | 550 + 580 |
| (259) | benzothiazol-2-yl | m-{O—(CH$_2$)$_3$—P(=O)[—O—CH$_2$—CH(C$_2$H$_5$)—CH$_2$—CH$_2$—CH$_2$—CH$_3$]$_2$}-anilide | 548 + 583 |

TABLE II-continued
| Formula No. | $R_{11}$ | $R_{12}$ | Abs. max in [nm]*) (see footnote, Table I) |
|---|---|---|---|
| (260) | | | 440 + 535 |
| (261) | | | 440 + 535 |
| (262) | | | 440 + 536 |

TABLE II-continued

[Structure showing pyrazolone core with R11 on N and HN—CO—R12 substituent]

| Formula No. | $R_{11}$ | $R_{12}$ | Abs. max in [nm]* (see footnote, Table I) |
|---|---|---|---|
| (263) | 2,6-dimethyl-4-chlorophenyl | 3,5-bis[O—(CH$_2$)$_3$—P(=O)(O—CH$_2$—CH(C$_2$H$_5$)—CH$_2$—CH$_2$—CH$_3$)$_2$]phenyl-NH—CO— | 440 + 534 |
| (264) | 2-methyl-4-methoxy-6-chlorophenyl | 3-[O—(CH$_2$)$_3$—P(=O)(O—CH$_2$—CH(C$_2$H$_5$)—CH$_2$—CH$_2$—CH$_3$)$_2$]phenyl-NH—CO— | 440 + 536 |
| (265) | 2-methoxy-3-methyl-5-chlorophenyl (dichloro) | 3,5-bis[O—(CH$_2$)$_3$—P(=O)(O—CH$_2$—CH$_2$—CH$_2$—CH$_3$)$_2$]phenyl-NH—CO— | 436 + 537 |

TABLE II-continued

| Formula No. | $R_{11}$ | $R_{12}$ | Abs. max in [nm]* (see footnote, Table I) |
|---|---|---|---|
| (266) | 3,5-dichloro-4-methyl-phenyl with OCH₃ | 3-[NH-CO-phenyl-O-(CH₂)₃-P(=O)(O-CH₂-CH₂-CH₂-CH₃)₂]; with second O-(CH₂)₃-P(=O)(O-CH₂-CH₂-CH₂-CH₃)₂ branch at 5-position | 436 + 540 |
| (267) | 3,5-dichloro-4-methyl-phenyl with OCH₃ | {3-[NH-CO-phenyl-O-(CH₂)₃-P(=O)(O-CH₂-CH(C₂H₅)-CH₂-CH₂-CH₂-CH₃)]}₂ | 436 + 536 |
| (268) | 3,5-dichloro-2-methoxy-phenyl | {3-[NH-CO-phenyl-O-(CH₂)₃-P(=O)(O-CH₂-CH(C₂H₅)-CH₂-CH₂-CH₂-CH₃)]}₂ | 438 + 540 |
| (269) | 3,5-dichloro-2-methyl-phenyl | {3-[NH-CO-phenyl-O-(CH₂)₃-P(=O)(O-CH₂-CH(C₂H₅)-CH₂-CH₂-CH₂-CH₃)]}₂ | 438 + 540 |

TABLE II-continued
| Formula No. | $R_{11}$ | $R_{12}$ | Abs. max in [nm]* (see footnote, Table I) |
|---|---|---|---|
| (270) | 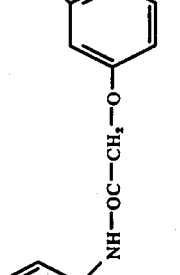 | 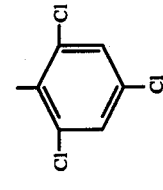 | 438 + 544 |
| (271) | 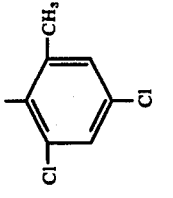 | 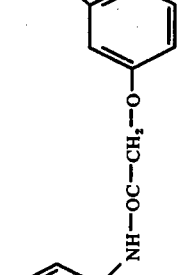 | 440 + 532 |
| (272) | 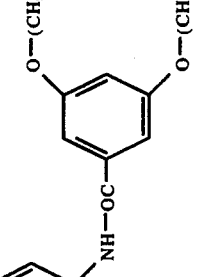 | 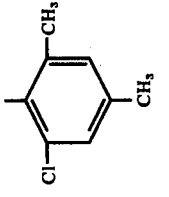 | 438 + 540 |

TABLE II-continued

| Formula No. | $R_{11}$ | $R_{12}$ | Abs. max in [nm]* (see footnote, Table I) |
|---|---|---|---|
| (273) | 2,5-dichlorophenyl | -NH-C₆H₄-NH-CO-C₆H₃(O-(CH₂)₃-P(=O)(O-CH₂-CH₂-CH₂-CH₃)₂)₂ | 430 + 547 |
| (274) | 2,5-dichlorophenyl | -NH-C₆H₄-NH-CO-C₆H₄-O-(CH₂)₃-P(=O)(O-CH₂-CH(C₂H₅)-CH₂-CH₂-CH₂-CH₃)₂ | 430 + 546 |
| (275) | 4-(CH₃SO₂)-C₆H₄- | -C₆H₄-NH-CO-C₆H₄-O-(CH₂)₃-P(=O)(O-CH₂-CH₂-CH₂-CH₃)₂ | 440 + 538 |
| (276) | 4-((C₂H₅)₂NSO₂)-C₆H₄- | -C₆H₄-NH-CO-C₆H₃(O-(CH₂)₃-P(=O)(O-CH₂-CH₂-CH₂-CH₃)₂)₂ | 440 + 542 |

EXAMPLE 16

Bromination of the compound of the formula (245) according to US-PS 3,006,759 gives the compound of the formula

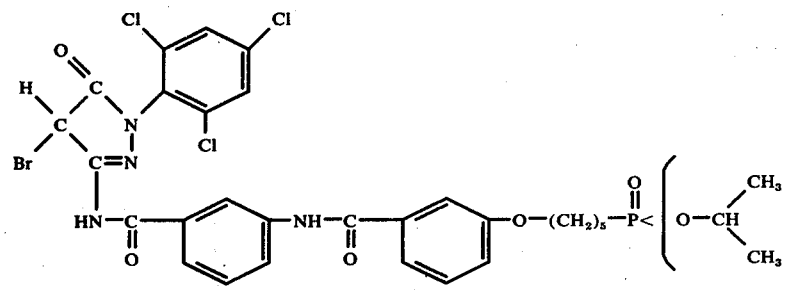

Absorption maximum 434 + 542 nm.

EXAMPLE 17

14.2 g of sodium m-nitrophenolate and 22.8 g of 3-bromopropylphosphonic acid diethyl ester in 200 ml of methyl ethyl ketone are stirred for 6 hours at 110° C. The mixture is cooled to room temperature, the sodium bromide which has separated out is filtered off, the solvent is distilled off and the residue is fractionated in a high vacuum.

21.0 g of nitro compound of the formula

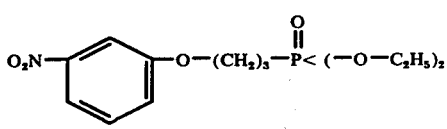

are obtained as a yellow oil of boiling point (0.3 mm Hg) 180 – 185° C.

Catalytic reduction of 43.0 g of the nitro compound at room temperature under normal pressure gives 36.5 g of amino compound of the formula

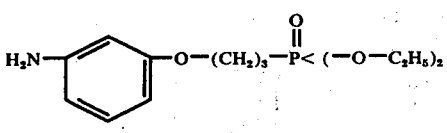

as a light yellow oil.

4.0 of 1-ethoxy-1-amino-acrylic acid ethyl ester hydrochloride are dissolved in 23 ml of methanol and this solution is added to 5.8 g of amine of the above formula. The mixture is stirred for 24 hours at room temperature and evaporated to dryness, the residue is extracted with 50 ml of benzene and the extract is concentrated. The residue consists of 8.5 g of red-brown oil of the formula

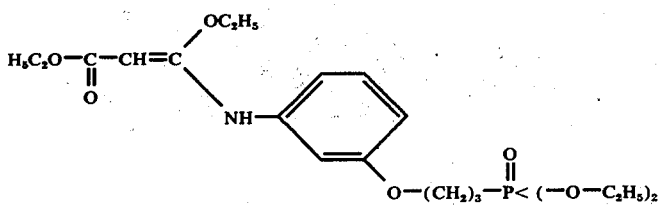

4.4 g of this compound and 1.1 g of penylhydrazine in 10 ml of ethanol are stirred for 18 hours at room temperature. The mixture is filtered and the residue is concentrated and caused to crystallise by trituration with diethyl ether. Recrystallisation from benzene and from acetone gives 0.5 g of pure coupling agent of the formula (401) (Table III) as a light yellow powder of melting point 148°–150° C.

The compounds of the formulae (402) and (410) to (413) are prepared analogously.

EXAMPLE 18

6.8 g of 3-methoxy-3-(2',4',6'-trichlorophenylhydrazino)-acrylic acid ethyl ester and 5.7 g of compound of the formula

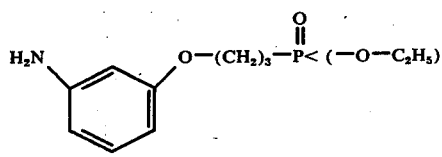

in 5 ml of glacial acetic acid are stirred for 3 hours at 100° C under nitrogen. 50 ml of ethanol are added, the mixture is cooled to 0° C and the product which has crystallised out is filtered off.

After recrystallisation from ethanol, 1.7 g of coupling agent of the formula (403) are obtained as a yellow powder of melting point 162°–164° C.

The compounds of the formulae (404) to (409) are prepared analogously.

EXAMPLE 19

The compounds of the formulae (414) to (424) and (427) to (430) are prepared analogously to Example 15. The compounds (408) and (409) are prepared analogously to Example 17.

EXAMPLE 20

1-(3Nitro-2,4,6-trimethylphenyl)-3-(4-chloroanilino)-5-pyrazolone.

26.9 g (0.14 mol) of trimethoxypropionic acid ethyl ester (prepared according to DT-OS 2,042,920) are dissolved in 100 ml of absolute methanol, 7 ml of glacial acetic acid are added and the mixture is heated to the boil. 23.4 g (0.12 mol) of 3-nitro-2,4,6-trimethylphenylhydrazine (prepared according to DT-OS 2,156,913) are introduced in portions into the mixture over the course of 10 minutes. The mixture is stirred for a further 10 minutes at the boil and is allowed to cool whilst stirring. The orange crystals which have precipitated are filtered off, washed with a little methanol and dried (18 hours in vacuo at 50° C). 14.4 g of β-methoxy-β-(3-nitro-2,4,6-trimethylphenylhydrazino)-acrylic acid ethyl ester of melting point 82°–83° C are obtained.

16.3 g (0.05 mol) of this compound are well mixed with 6.95 g (0.054 mol) of p-chloroaniline and the mixture is stirred with 10.1 ml of glacial acetic ° The mixture is warmed to 50°C for 4 hours and 50 ml of absolute methanol are then added. The whole is allowed to cool whilst stirring and the cyrstals are filtered off and rinsed with a little methanol. After drying in vacuo at 70° C, 11.9 g of the pyrazolone, of melting point 263°–265° C, are obtained. 1-(3-Amino-2,4,6-trimethylphenyl)-3-(4-chloroanilino)-5-pyrazolone.

7.5 g (0.02 mol) of the above nitropyrazolone are dissolved in 70 ml of DMF and 15 ml of glacial acetic acid and 6 ml of $H_2O$ are added. The mixture is warmed to 40° C under a $N_2$ atmosphere and 20 g of Fe powder are introduced. The reaction is allowed to take place for 8 hours at 40° C, 40 ml of methanol are added, and the mixture is filtered. The filtrate is poured into 700 ml of $H_2O$ and the product which has precipitated is filtered off. The filter residue is dissolved in 60 ml of hot methanol and allowed to crystallise. After filtering off the crystals, and drying them at 70° C in vacuo, 5.7 g of the above aminopyrazolone, of melting point 236°–237° C, are obtained.

Coupling agent of the formula No. 425, Table III 0.72 g (0.002 mol) of the above aminopyrazolone are dissolved in 10 ml of glacial acetic acid and the solution is mixed with 210 mg of anhydrous sodium acetate. A solution of 0.73 g (0.0022 mol) of the acid chloride of the formula

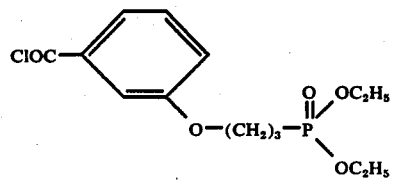

(prepared according to Example 15) in 2.5 ml of glacial acetic acid is allowed to run in at 45°–50° C. The reaction is allowed to take place for 2 hours at this temperature, the reaction mixture is poured into 100 ml of ice water and the product is filtered off and washed thoroughly with $H_2O$. The crude product is taken up in chloroform and precipitated with petroleum ether. After addition of a little $H_2O$, the product solidifies. It is filtered off and dried in vacuo at 50° C. Yield: 200 mg. Melting point: 132°–138° C.

EXAMPLE 21

Coupling agent of the formula No. 426, Table III

This coupling agent is prepared analogously to Example 20. However, instead of the acid chloride used in Example 20, the acid chloride of the formula

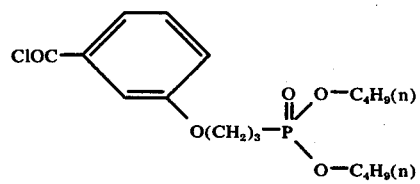

prepared analogously to Example 15 is employed.
A product of melting point 117°–127° C is obtained.

TABLE III $$\underset{(400)}{\underset{R_{14}}{\overset{R_{13}}{\underset{\|}{\overset{\|}{\text{structure}}}}}}$$

| Formula No. | $R_{13}$ | $R_{14}$ | Abs.max.*) in [nm] |
|---|---|---|---|
| (401) | 4-methylphenyl | 3-methylphenyl-O-(CH$_2$)$_3$-P(=O)(-O-C$_2$H$_5$)$_2$ | 429 + 524 |
| (402) | 2-chlorophenyl | 3-methylphenyl-O-(CH$_2$)$_3$-P(=O)(-O-C$_2$H$_5$)$_2$ | 430 + 534 |
| (403) | 2,5-dichlorophenyl | 3-methylphenyl-O-(CH$_2$)$_3$-P(=O)(-O-C$_2$H$_5$)$_2$ | 424 + 526 |
| (404) | 2,5-dichlorophenyl | 4-methylphenyl-O-(CH$_2$)$_3$-P(=O)(-O-C$_2$H$_5$)$_2$ | 425 + 530 |

TABLE III-continued (400) structure with $R_{13}$, $R_{14}$ substituents on pyrazolone ring

| Formula No. | $R_{13}$ | $R_{14}$ | Abs.max.*) in [nm] |
|---|---|---|---|
| (405) | phenyl | $-O-(CH_2)_3-\overset{O}{P}(-O-C_2H_5)_2$ attached to p-tolyl | 428 + 526 |
| (406) | 3-chlorophenyl | $-O-(CH_2)_3-\overset{O}{P}(-O-C_2H_5)_2$ attached to p-tolyl | 426 + 530 |
| (407) | phenyl | $-(CH_2)_3-\overset{O}{P}(-O-C_2H_5)_2$ attached to p-tolyl | 429 + 527 |
| (408) | 2,4,5-trichlorophenyl | $-(CH_2)_3-\overset{O}{P}(-O-C_2H_5)_2$ attached to p-tolyl | 426 + 530 |

TABLE III-continued

| Formula No. | R₁₃ | R₁₄ | Abs.max.* in [nm] |
|---|---|---|---|
| (409) | 2,5-dichlorophenyl | 3-methylphenyl-O—(CH₂)₃—P(=O)(—O—CH₂—CH₂—CH₂—CH₃)₂ | 426 + 330 |
| (410) | 2-chlorophenyl | 4-methylphenyl-(CH₂)₃—P(=O)(—O—C₂H₅)₂ | 438 + 532 |
| (411) | 2-chlorophenyl | 3-methylphenyl-O—(CH₂)₃—P(=O)(—O—CH₂—CH₂—CH₂—CH₃)₂ | 428 + 532 |
| (412) | phenyl | 3-methylphenyl-O—(CH₂)₃—P(=O)(—O—CH₂—CH₂—CH₂—CH₃)₂ | 430 + 528 |

TABLE III-continued (400)

Structure: pyrazolone with N-R$_{13}$, =N–, C(=O), H$_3$C, and C–HN–R$_{14}$

| Formula No. | R$_{13}$ | R$_{14}$ | Abs.max.*) in [nm] |
|---|---|---|---|
| (413) | 4-Cl-C$_6$H$_4$– (3-methylphenyl derivative with Cl) | –phenyl–O–(CH$_2$)$_3$–P(=O)<(–O–CH$_2$–CH(C$_2$H$_5$)–CH$_2$–CH$_2$–CH$_2$–CH$_3$)$_2$ (with 3-methylphenyl, bracketed ×2) | 428 + 533 |
| (414) | C$_6$H$_5$– | 3-methylphenyl–O–(CH$_2$)$_3$–P(=O)<(–O–C$_2$H$_5$)$_2$ ; with 3-methylphenyl–NH–OC– | 430 + 530 |
| (415) | 2,4,5-trichlorophenyl | 3-methylphenyl–O–(CH$_2$)$_3$–P(=O)<(–O–C$_2$H$_5$)$_2$ ; with 3-methylphenyl–NH–OC– | 426 + 532 |
| (416) | C$_6$H$_5$– | 4-methylphenyl–NH–OC–(phenyl)–O–(CH$_2$)$_3$–P(=O)<(–O–C$_2$H$_5$)$_2$ | 426 + 528 |

TABLE III-continued (400)

[Structure: pyrazolone core with N–R13, N, HN–R14, C=O, H2C, C]

| Formula No. | R13 | R14 | Abs.max.*) in [nm] |
|---|---|---|---|
| (417) | 4-methylphenyl | 3-[O-(CH2)3-P(=O)(-O-CH2-CH2-CH2-CH3)2]phenyl-NH-CO- attached to 4-methylphenyl | 428 + 528 |
| (418) | 3-methylphenyl | 3-[O-(CH2)2-P(=O)(-O-CH2-CH2-CH2-CH3)2]phenyl-NH-CO- attached to 3-methylphenyl | 430 + 530 |
| (419) | 2,5-dichlorophenyl | 3-[O-(CH2)3-P(=O)(-O-CH2-CH2-CH2-CH3)2]phenyl-NH-CO- attached to 3-methylphenyl | 427 + 532 |
| (420) | 4-methylphenyl | 3-[O-(CH2)3-P(=O)(-O-CH2-CH(C2H5)-CH2-CH2-CH2-CH3)2]phenyl-NH-CO- attached to 4-methylphenyl | 428 + 529 |

TABLE III-continued

| Formula No. | $R_{13}$ | $R_{14}$ | Abs.max.*) in [nm] |
|---|---|---|---|
| (421) | phenyl | $\{O-(CH_2)_3-\underset{\underset{O}{\parallel}}{P}<\underset{O-CH_2-CH(C_2H_5)-CH_2-CH_2-CH_3}{}\}_2$ with 3-(N-(3-methylphenyl)carbamoyl)phenyl linkage | 430 + 528 |
| (422) | 2,5-dichlorophenyl | $\{O-(CH_2)_3-\underset{\underset{O}{\parallel}}{P}<\underset{O-CH_2-CH(C_2H_5)-CH_2-CH_2-CH_3}{}\}_2$ with 3-(N-(3-methylphenyl)carbamoyl)phenyl linkage | 426 + 530 |
| (423) | phenyl | 3,5-bis[O-(CH$_2$)$_3$-P(=O)(O-CH$_2$-CH$_2$-CH$_2$-CH$_3$)$_2$]phenyl with N-(3-methylphenyl)carbamoyl | 430 + 530 |

TABLE III-continued

Structure (400):

$R_{13}$—N, N=C—HN—$R_{14}$, with C=O and H₂C in the ring

| Formula No. | $R_{13}$ | $R_{14}$ | Abs.max.*) in [nm] |
|---|---|---|---|
| (424) | 2,4,5-trichlorophenyl | 3-methylphenyl-NHCO-, with 3,5-bis[O-(CH₂)₃-P(=O)(-O-CH₂-CH₂-CH₂-CH₃)₂] substituents | 427 + 532 |
| (425) | 2,4,6-trimethylphenyl-NHCO-, 3-O(CH₂)₃-P(=O)(-O-C₂H₅)₂ | 4-chlorophenyl | 430 + 530 |
| (426) | 2,4,6-trimethylphenyl-NHCO-, 3-O(CH₂)₃-P(=O)(-O-CH₂-CH₂-CH₂-CH₃)₂ | 4-chlorophenyl | 430 + 528 |

TABLE III-continued (400) [pyrazolone structure with R13, R14]

| Formula No. | R13 | R14 | Abs.max.*) in [nm] |
|---|---|---|---|
| (427) | 4-(N,N-diethylsulfamoyl)phenyl | 3-[(3-methylphenyl)aminocarbonyl]phenoxy-(CH$_2$)$_3$-P(=O)(O-CH$_2$-CH$_2$-CH$_2$-CH$_3$)$_2$ | 431 + 538 |
| (428) | 2,4,6-trichlorophenyl | 3,5-bis{[(4-chloro-3-methylphenyl)aminocarbonyl]}phenoxy-(CH$_2$)$_3$-P(=O)(O-CH$_2$-CH$_2$-CH$_2$-CH$_3$)$_2$ | 430 + 537 |
| (429) | 4-(methylsulfonyl)phenyl | 3-[(3-methylphenyl)aminocarbonyl]phenoxy-(CH$_2$)$_3$-P(=O)(O-CH$_2$-CH$_2$-CH$_2$-CH$_3$)$_2$ | 430 + 538 |

TABLE III-continued

| Formula No. | $R_{13}$ | $R_{14}$ | Abs.max.*) in [nm] |
|---|---|---|---|
| (430) | 4-methylphenyl-SO$_2$CH$_3$ | 3,5-bis[O-(CH$_2$)$_3$-P(=O)(O-CH$_2$-CH$_2$-CH$_2$-CH$_3$)$_2$]phenyl-NHCO-(3-methylphenyl) | 430 + 540 |

EXAMPLE 22

2.6 g of 1-hydroxy-2-naphtoic acid phenyl ester and 2.9 g of 3-(m-aminophenyl)-propoxy-phosphonic acid diethyl ester are warmed to 130° – 140° C over the course of 4 hours. The phenol split off is distilled off in vacuo and the crude product is purified by column chromatography on silica. 1.5 g of pure coupling agent of the formula (601) of Table IV are obtained in the form of a white powder of melting point 104° – 107° C.

The compound of the formula (602) is prepared analogously. Melting point 79° – 81° C.

USE EXAMPLES

EXAMPLE I 0.3 mmol of coupling agent of the formula (215) is dissolved in 2.0 ml of tricresyl phosphate/methylene chloride (3:7). The methylene chloride is evaporated off, 6.0 ml of an 8% strength aqueous solution of sodium isopropylnaphthalene-sulphonate, 20.0 ml of 6% strength gelatine solution and 3.4 ml of water are added and the mixture is adjusted to pH 6.5 and emulsified for 5 minutes by means of an ultrasonic apparatus with an output of 100 watt.

TABLE IV

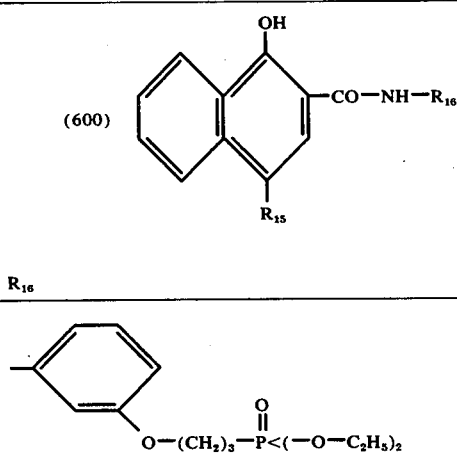

| Formula No. | $R_{15}$ | $R_{16}$ | Abs.max.*) in [nm] |
|---|---|---|---|
| (601) | H |  —O—(CH$_2$)$_3$—P(=O)(—O—C$_2$H$_5$)$_2$ | 704 |
| (602) | H | —O—(CH$_2$)$_3$—P(=O)(—O—CH$_2$—CH$_2$—CH$_2$—CH$_3$)$_2$ | 706 |

EXAMPLE 23

3.1 g of 3,5-di[3'-di-n-butoxy-phospho)-propoxy]-benzoic acid chloride and 1.0 g of 2-amino-4,6-dichloro-5-methyl-phenol (prepared according to DOS 2,216,804) in 20 ml of N-methyl-pyrrolidone are stirred for 3 hours at room temperature. The reaction mixture is poured into 100 ml of water and the emulsion is then extracted with 150 ml of ether. The organic phase is washed until neutral, dried and concentrated. The crude product is purified by column chromatography on silica. 1.0 g of light brown oil of the formula (701)

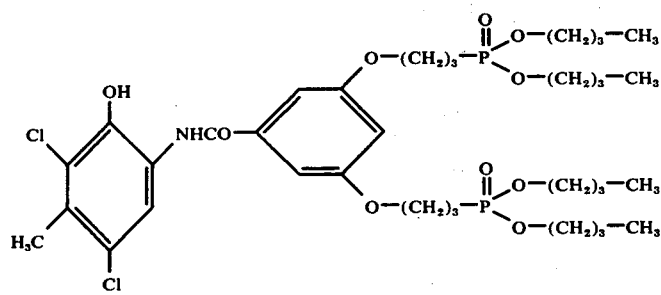

is obtained. The cyan dyestuff prepared therefrom according to Use Example I has an absorption maximum of 662 nm.

5.0 ml of coupling agent emulsion freshly treated with ultrasonics, 3.3 ml of silver bromide emulsion of pH 6.5, containing 1.4% of silver and 6.0% of gelatine, 2.0ml of 1% strength aqueous solution of the hardener of the formula

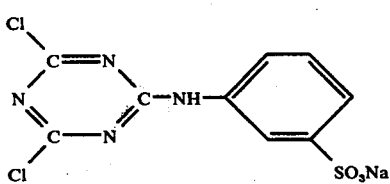

(701)

and 1.7 ml of water are mixed with one another and cast at 40° C on a substrated glass plate of size 13 × 18 cm. After solidifying at 10° C, the plate is dried in a drying cabinet with circulating air at 32° C.

A strip cut to 4.0 cm × 6.5 cm is exposed to 500 Lux/cm² under a step wedge for 2 seconds and is subsequently treated at 24° C as follows:

|  | Minutes |
|---|---|
| 1. Colour developing | 5 |
| 2. Soaking | 5 |
| 3. First fixing | 2 |
| 4. Soaking | 2 |
| 5. Silver bleaching | 2 |
| 6. Soaking | 2 |
| 7. Second fixing | 2 |
| 8. Soaking | 2 |
| 9. Drying | 10 |

The processing solutions have the following composition:

| I. Colour developing solution (pH=10.7) | |
|---|---|
| 4-Amino-3-methyl-N-ethyl-N-β-(methyl-sulphonamido)ethyl-aniline . 1½ H₂SO₄ . H₂O | 10 mmols |
| Anhydrous sodium sulphite | 2.0 g |
| Potassium bromide | 0.5 g |
| Potassium carbonate | 40.0 g |
| Benzyl alcohol | 10.0 g |
| Water | 1,000 g |
| II. Fixing solution (pH=4.5) | |
| Sodium thiosulphate . 6 H₂O | 80.0 g |
| Anhydrous sodium sulphite | 5.0 g |
| Sodium borate (borax) | 6.0 g |
| Potassium alum | 7.0 g |
| Acetic acid | 4.0 g |
| Water | 1,000 g |
| III. Silver bleach bath (pH=7.2) | |
| Potassium ferricyanide | 100.0 g |
| Boric acid | 10.0 g |
| Sodium borate (borax) | 5.0 g |
| Water | 1,000 g |

A clear, sharp magenta wedge with an absorption maximum at 540 nm and a subsidiary maximum at 434 nm is obtained.

Analogous results are obtained on using the remaining coupling agents listed in Tables I to IV.

EXAMPLE II

The strip obtained, and exposed, according to Example I is developed for 6 minutes at 24° C by means of the developer solution specified below and is rinsed with water at the same temperature.

It is then uniformly exposed to white light and colour-developed as stated in Example I. The strip thus treated gives a clear magenta wedge corresponding to a colour reversal material.

| IV. Black-and-white developer solution (pH=10.8) | |
|---|---|
| 4-Hydroxy-N-methylaniline . H₂SO₄ | 1.0 g |
| Hydroquinone | 3.0 g |
| Anhydrous sodium sulphite | 50.0 g |
| Sodium carbonate . H₂O | 25.0 g |
| Potassium thiocyanate | 3.6 g |
| Potassium bromide | 2.6 g |
| Water | 1,000 g |

Analogous results are obtained on using the remaining coupling agents listed in Tables I to IV or on using the coupling agent of the formula (701).

EXAMPLE III

The casting solution obtained according to Example I using an emulsion which is sensitive to green and the coupling agent of the formula (215) is cast on an opaque white acetate film provided with an adhesive layer. On top of this is cast an emulsion sensitive to red, which has been prepared analogously and contains the coupling agent of the formula (701), and finally an emulsion prepared analogously which contains the coupling agent of the formula (105).

The material is exposed through a colour-negative film and developed in accordance with the instructions given in Example I, whereby a clear colour copy is obtained.

EXAMPLE IV

A solution of 25 mg of the coupling agent of the formula (222) in 1 ml of methylene chloride is emulsified by means of ultrasonics in a mixture consisting of 1.6 ml of 6% strength gelatine solution, 2.0 ml of distilled water and 1.0 ml of an 8% strength aqueous solution of sodium diisobutylnaphthalene sulphonate.

After adjusting the pH value to 6.5, 1.0 ml of a 1% strength aqueous solution of the hardener from Example I and 1.6 ml of a silver bromide emulsion containing 1.4% of silver are added and the mixture thus obtained is spread by means of a glass rod on a substrated glass plate of size 13 × 18 cm. After drying at room temperature, the material is exposed, and developed, as described in Example I. A colour wedge with a maximum density of 1.00 is obtained.

EXAMPLE V 25 mg of the coupling agent of the formula (218) and 50 mg of a copolymer consisting of 50 parts of styrene and 50 parts of ethyl acrylate are dissolved in 1.2 ml of methylene chloride and this solution is dispersed, and cast with an emulsion, as described in Example IV. After drying, the material is exposed, and developed, as described in Example I. A colour wedge of maximum density 0.78 is obtained.

What we claim is:

1. Color-photographic recording material with at least one light-sensitive silver halide emulsion layer which contains at least one color coupler having an active methylene group or a phenolic hydroxyl group and containing at least one radical of a phosphonic acid diester, phosphonic acid diamide or phosphonic acid ester amide.

2. Photographic material as claimed in claim 1 which contains a colour coupler of the formula

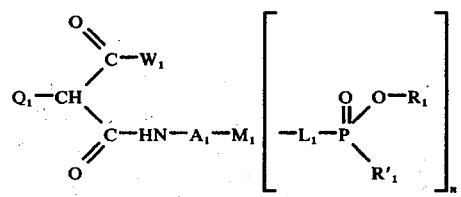

wherein
$W_1$ denotes an alkyl radical or benzene radical,
$Q_1$ denotes a radical which can be split off during colour coupling,
$A_1$ denotes a benzene radical,
$M_1$ denotes a direct bond, an oxygen atom or one of the atom groupings alkyl

—N—

(of which the alkyl group contains at most 4 carbon atoms), —CO—HN—, NH—OC—, —CO—O, —CO—HN—benzene radical and —NH—OC—benzene radical, L$_1$ denotes an oxygen atom, an alkylene group, a cyclohexane radical, a benzene radical or an aralkylene radical, but only one of the symbols M$_1$ and L$_1$ can represent an oxygen atom, R$_1$ denotes an alkyl group with 2 to 18 carbon atoms, R'$_1$ denotes an alkyl group with 2 to 8 carbon atoms or an alkoxy group with 2 to 18 carbon atoms or R$_1$ and R'$_1$ together denote an -O-alkylene- group and n denotes one of the numbers 1 and 2.

3. Photographic material as claimed in claim 1 which contains a colour coupler of the formula

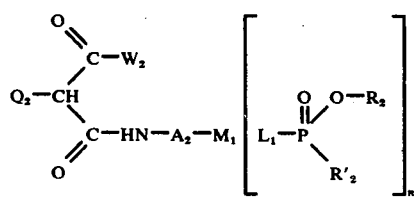

wherein

M$_1$, L$_1$ and n have the indicated meaning,

W$_2$ denotes a tertiary butyl radical, a benzene radical which is not substituted further or a benzene radical which is substituted further by at least one of the substituents alkyl with at most 4 carbon atoms, methoxy, ethoxy, chlorine or benzoylamino, Q$_2$ denotes one of the radicals of the formulae —H, —Cl.

4. Photographic material as claimed in claim 1 which contains a colour coupler of the formula

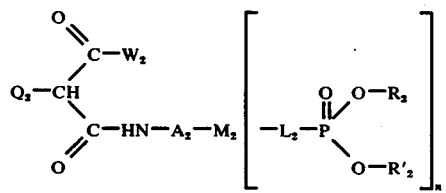

wherein

W$_2$, Q$_2$, A$_2$, R$_2$, R'$_2$ and n have the indicated meaning,

M$_2$ denotes a direct bond, an oxygen atom or one of the atom groupings —CO—HN—, —NH—OC—, —CO—HN—benzene radical or —NH—OC—benzene radical, and L$_2$ denotes an oxygen atom, an alkylene group with 1 to 3 carbon atoms, a benzene radical or an aralkylene radical, with the proviso that M$_2$ does not present oxygen, —CO—NH— or —HN—CO— if L$_2$ represents an oxygen atom, and n can only be 2 if M$_2$ is a —CO—HN—benzene radical or —NH—OC—benzene radical.

5. Photographic material according to claim 4 which contains a colour coupler of the formula

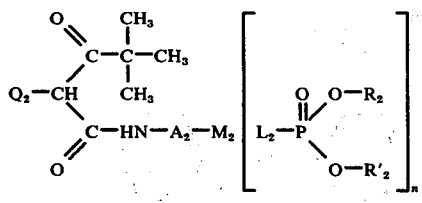

wherein

Q$_2$, A$_2$, M$_2$, L$_2$, R$_2$, R'$_2$ and n have the indicated meaning.

6. Photographic material according to claim 4 which contains a colour coupler of the formula

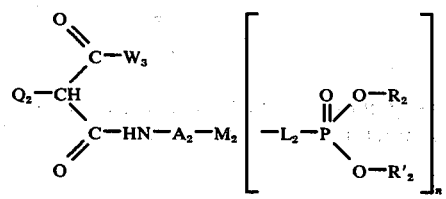

wherein

Q$_2$, A$_2$, M$_2$, L$_2$, R$_2$, R'$_2$ and n have the indicated meaning and

W$_3$ denotes a benzene radical which is not substituted further or a benzene radical which is substituted further by at least one of the substituents alkyl with at most 4 carbon atoms, methoxy, ethoxy, chlorine or benzoylamino.

7. Photographic material as claimed in claim 1 which contains a colour coupler which corresponds to one of the formulae

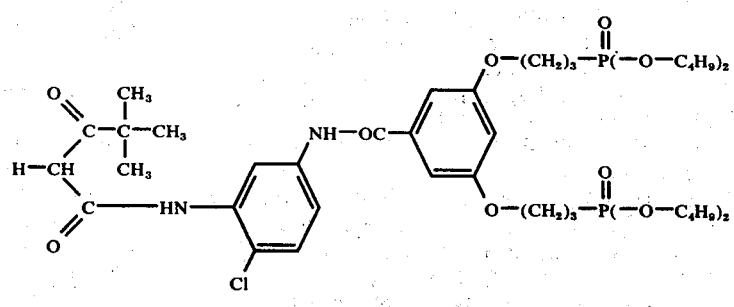

-continued

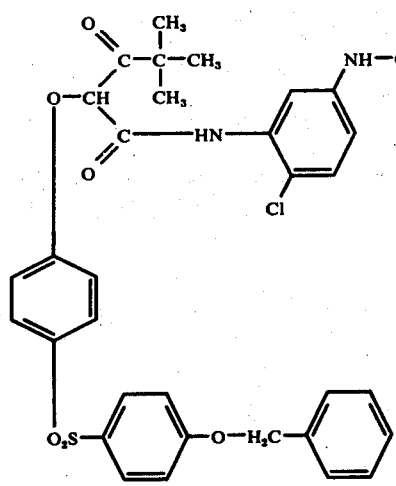

and

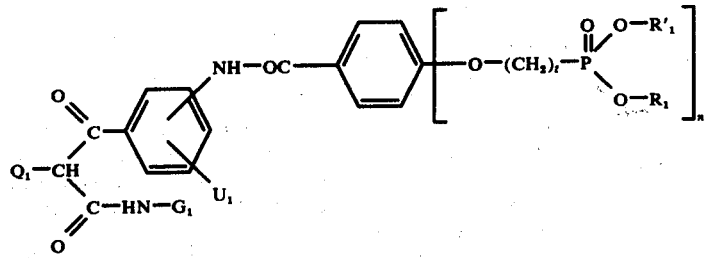

8. Photographic material according to claim 1 which contains a colour coupler of the formula

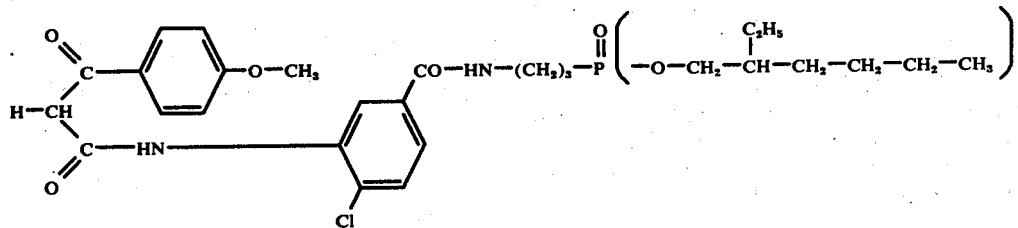

wherein

G₁ denotes a benzene radical,
Q₁ denotes a radical which can be split off during colour coupling,
U₁ denotes a hydrogen atom, a chlorine atom, an alkali group with at most 4 carbon atoms or an alkoxy group with at most three carbon atoms,
R₁ denotes an alkyl group with 2 to 18 carbon atoms,
n denotes one of the numbers 1 and 2 and t denotes one of the numbers 3 and 5.

9. Photographic material as claimed in claim 8 which contains a colour coupler of the formula

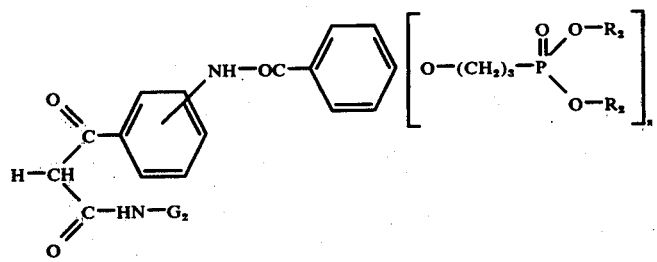

wherein
G₂ denotes a benzene radical which is not substituted further or is substituted further by at least one of the substituents chlorine, methyl, methoxy or phenoxy and
R₂ denotes an alkyl group with 2 to 8 carbon atoms and
n has the indicated meaning.

10. Photographic material as claimed in claim 9 which contains the colour coupler of the formula

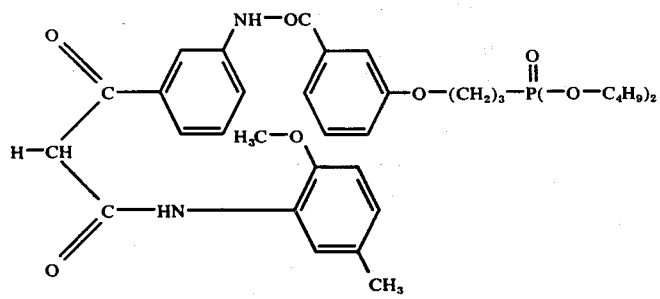

11. Photographic material according to claim 1 which contains a colour coupler of the formula

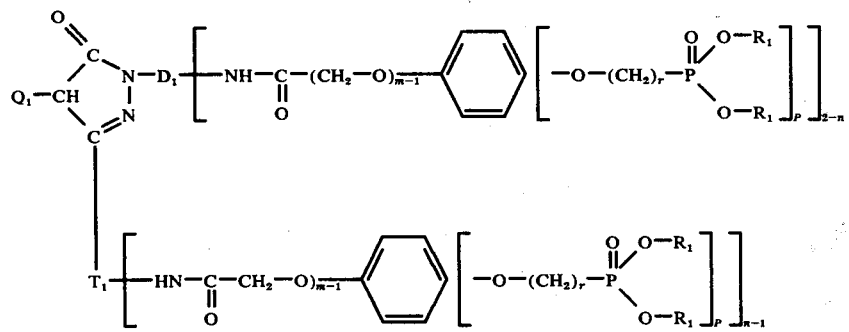

wherein
Q₁ denotes a radical which can be split off during colour coupling,
D₁ denotes a benzene radical which is not substituted further or a benzene radical which is substituted further by at least one of the substituents halogen, nitrile, lower alkyl (which can itself carry further substituents), lower alkoxy, lower alkylsulphonyl or acylamino with 1 to 28 carbon atoms,
T₁ denotes an acylamino group, a phenylureido group, a phenylamino group which is not substituted further or is substituted further by at least one of the substituents halogen, lower alkyl, lower alkoxy or acylamino with 1 to 28 carbon atoms or (if $n = 2$) a direct bond,
R₁ denotes an alkyl group with 2 to 18 carbon atoms,
m and n each denote one of the numbers 1 and 2,
p denotes one of the numbers 1, 2 and 3 and r denotes an integer of value at most 18.

12. Photographic material as claimed in claim 11 which contains a colour coupler of the formula

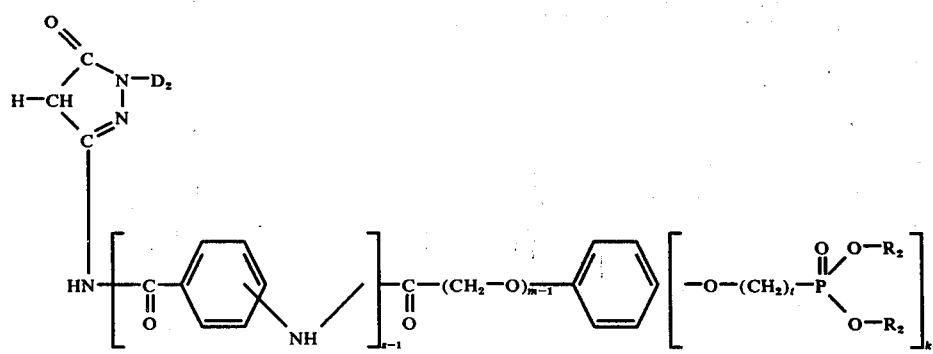

wherein
D₂ denotes a benzene radical which is optionally substituted further by one or more chlorine atoms, methyl groups or methoxy groups and/or by a nitrile group,
R₂ denotes an alkyl group with 2 to 8 carbon atoms,
k, m and s each denote one of the numbers 1 and 2 and
t denotes one of the numbers 3 and 5.

13. Photographic material as claimed in claim 11 which contains a colour coupler of the formula

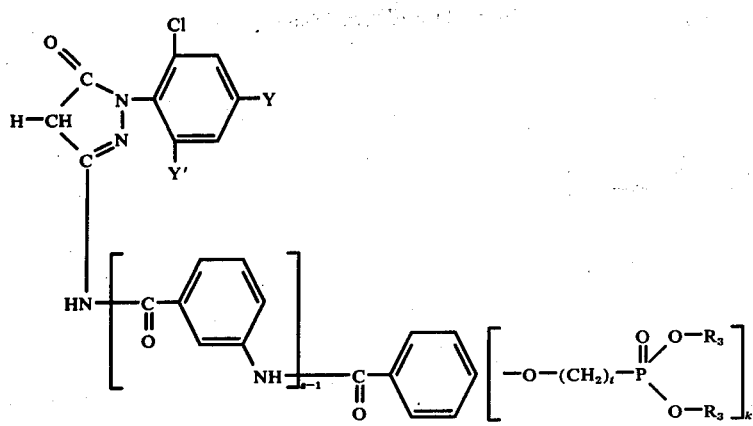

wherein
R₃ denotes a n-butyl or 2-ethylhexyl group,
Y denotes a chlorine atom, a methyl group or methoxy group,
Y' denotes a chlorine atom or a methyl group,
k and s each denote one of the numbers 1 and 2 and t denotes one of the numbers 3 and 5.

14. Photographic material according to claim 11 which contains a colour coupler of the formula

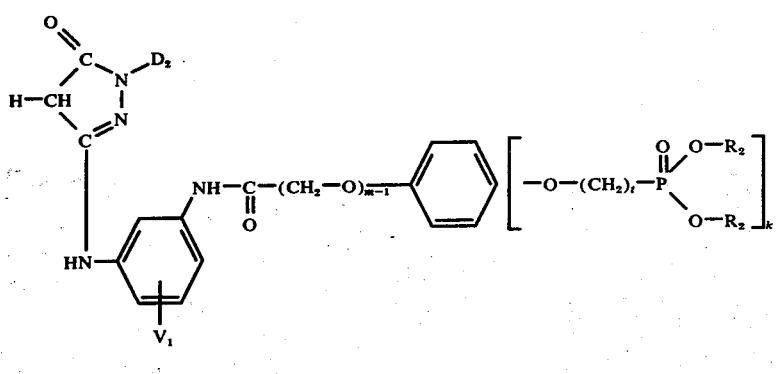

wherein
D₂, R₂, m and t have the indicated meaning and V₁ denotes a hydrogen atom or a chlorine atom.

15. Photographic material according to claim 14 which contains a colour coupler of the formula

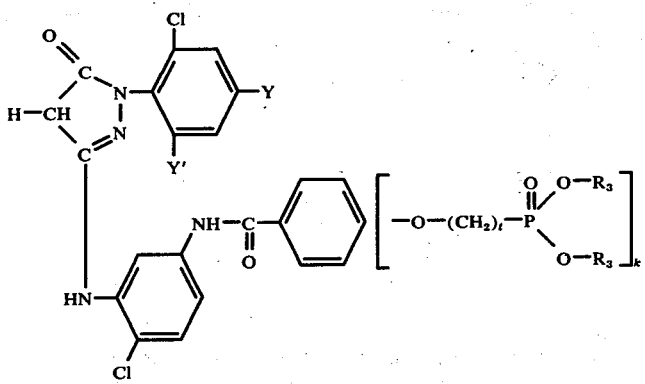

wherein
Y, Y', R₃ k and t have the indicated meaning.

16. Photographic material according to claim 1 which contains a colour coupler of the formula

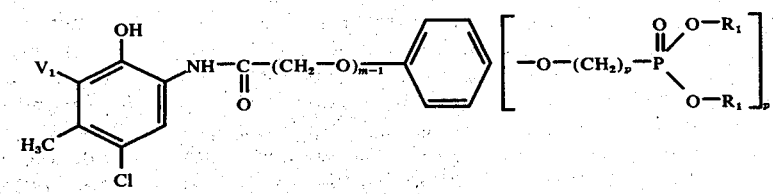

wherein
R₁, R₂, V₁, m, p and r have the indicated meaning.

17. Photographic material according to claim 16 which contains a colour coupler of the formula

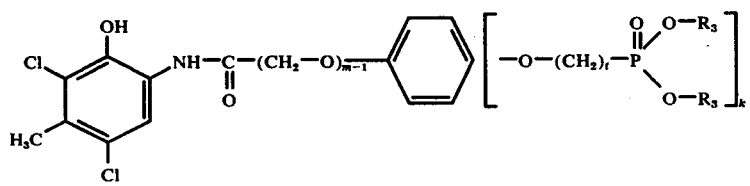

wherein
R₃, k, m and t have the indicated meaning.

18. Photographic material according to claim 17 which contains a colour coupler of the formula

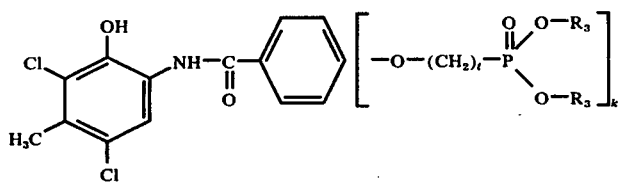

wherein
R₃, k and t have the indicated meaning.

19. Photographic material according to claim 18 which contains a colour coupler of the formula

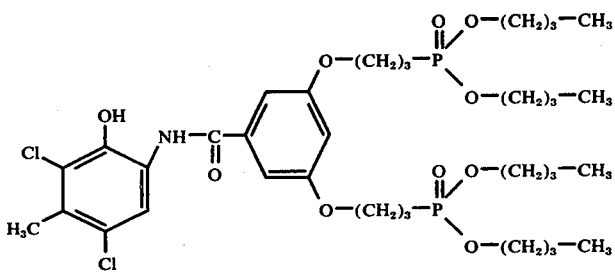

20. Photographic material according to claim 1 which contains a colour coupler of the formula

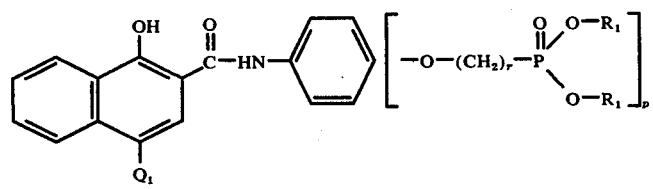

wherein
Q₁, R₁, p and r have the indicated meaning.

21. Photographic material according to claim 20 which contains a colour coupler of the formula

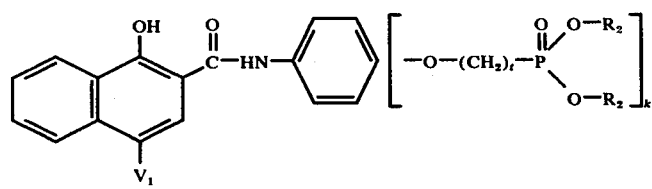

wherein V₁, R₂ and k have the indicated meaning.

22. Photographic material according to claim 21 which contains a colour coupler of the formula

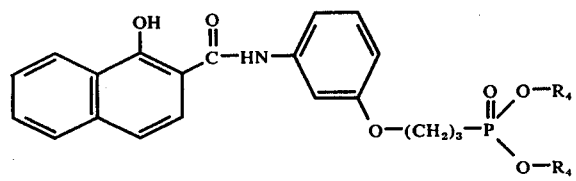
* * * * *

UNITED STATES PATENT OFFICE
CERTIFICATE OF CORRECTION

PATENT NO. : 4,026,709
DATED : May 31, 1977
INVENTOR(S) : Bernhard Piller et al.

It is certified that error appears in the above-identified patent and that said Letters Patent are hereby corrected as shown below:

First page - the following was omitted:

-- FOREIGN APPLICATION PRIORITY DATA

Mar. 9, 1973    Switzerland...... 3516/73    --

Signed and Sealed this twenty-third Day of August 1977

[SEAL]

Attest:

RUTH C. MASON
Attesting Officer

C. MARSHALL DANN
Commissioner of Patents and Trademark